(12) United States Patent
Ruminski et al.

(10) Patent No.: US 10,035,778 B2
(45) Date of Patent: Jul. 31, 2018

(54) META-AZACYCLIC AMINO BENZOIC ACID DERIVATIVES AS PAN INTEGRIN ANTAGONISTS

(71) Applicant: Saint Louis University, St. Louis, MO (US)

(72) Inventors: Peter G. Ruminski, Wildwood, MO (US); David W. Griggs, Ballwin, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 15/812,986

(22) Filed: Nov. 14, 2017

(65) Prior Publication Data
US 2018/0072684 A1 Mar. 15, 2018

Related U.S. Application Data

(63) Continuation of application No. PCT/US2016/069511, filed on Dec. 30, 2016.

(60) Provisional application No. 62/273,246, filed on Dec. 30, 2015.

(51) Int. Cl.
C07D 239/14 (2006.01)
C07D 401/12 (2006.01)

(52) U.S. Cl.
CPC ......... *C07D 239/14* (2013.01); *C07D 401/12* (2013.01)

(58) Field of Classification Search
CPC .................................................. C07D 239/14
See application file for complete search history.

(56) References Cited

U.S. PATENT DOCUMENTS

| | | | |
|---|---|---|---|
| 5,602,155 | A | 2/1997 | Ruminski |
| 5,639,765 | A | 6/1997 | Ruminski |
| 5,681,820 | A | 10/1997 | Ruminski |
| 5,773,646 | A | 6/1998 | Chandrakumar et al. |
| 5,798,370 | A | 8/1998 | Ruminski |
| 5,840,961 | A | 11/1998 | Behling et al. |
| 5,852,210 | A | 12/1998 | Chen et al. |
| 6,013,651 | A | 1/2000 | Rogers et al. |
| 6,028,223 | A | 2/2000 | Ruminski et al. |
| 6,100,423 | A | 8/2000 | Collins et al. |
| 6,172,256 | B1 | 1/2001 | Malecha et al. |
| 6,372,719 | B1 | 4/2002 | Cunningham et al. |
| 6,414,180 | B1 | 7/2002 | Colson et al. |
| 6,689,787 | B1 | 2/2004 | McKearn et al. |
| 6,933,304 | B2 | 8/2005 | Nagarajan et al. |
| 7,119,098 | B2 | 10/2006 | Nagarajan et al. |
| 8,716,226 | B2 | 5/2014 | Ruminski et al. |
| 9,085,606 | B2 | 7/2015 | Ruminski et al. |
| 2004/0082557 | A1 | 4/2004 | Wajszczuk et al. |
| 2005/0020505 | A1* | 1/2005 | Rogers ............. C07D 223/12 514/1.9 |
| 2007/0117849 | A1 | 5/2007 | Goodman et al. |
| 2014/0051715 | A1 | 2/2014 | Ruminski et al. |

FOREIGN PATENT DOCUMENTS

| | | |
|---|---|---|
| DE | 102009000854 A1 | 8/2010 |
| EP | 1667668 | 7/2008 |
| WO | WO 1996/023771 | 8/1996 |
| WO | WO 1997/008145 | 3/1997 |
| WO | WO 1997/036859 | 10/1997 |
| WO | WO 1997/036860 | 10/1997 |
| WO | WO 1997/036862 | 10/1997 |
| WO | WO 1999/044994 | 9/1999 |
| WO | WO 1999/044996 | 9/1999 |
| WO | WO 1999/052896 | 10/1999 |
| WO | WO 2000/038665 | 7/2000 |
| WO | WO 2000/038715 | 7/2000 |

(Continued)

OTHER PUBLICATIONS

Abdollahi et al., "Inhibition of α(v)β3 integrin survival signaling enhances antiangiogenic and antitumor effects of radiotherapy," Clin. Cancer Res., 11:6270-6279, 2005.
Adachi et al., "Significance of integrin α5 gene expression as a prognostic factor in node-negative non-small cell lung cancer," Clin. Cancer Res., 6(1):96-101, 2000.
Asano et al., "Increased expression of integrin α(v)β3 contributes to the establishment of autocrine TGF-β signaling in scleroderma fibroblasts," J. Immunol., 175(11):7708-7718, 2005.
Avraamides et al., "Integrins in angiogenesis and lymphangiogenesis," Nat. Rev. Cancer, 8(8):604-617, 2008.
Awasthi et al., "Practical enantioselective synthesis of β-substituted-β-amino esters," J. Org. Chem., 70:5387-5397, 2005.
Babadzhanova et al., "Convenient syntheses of 1,1,1,3,3,3-hexafluoro-2-organyl-propan-2-ols and the corresponding trimethylsilyl ethers," Tetrahedron, 61(7):1813-1819, 2005.

(Continued)

*Primary Examiner* — Paul V Ward
(74) *Attorney, Agent, or Firm* — Knobbe Martens Olson & Bear LLP

(57) ABSTRACT

The present disclosure provides pharmaceutical agents of the formula:

(I)

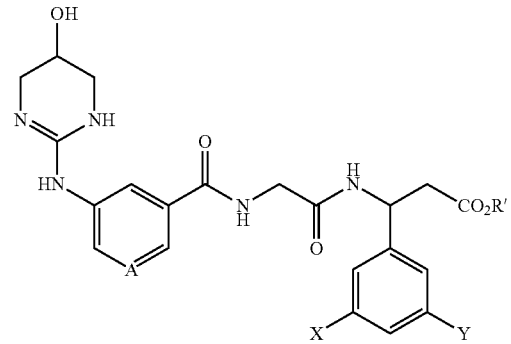

wherein the variables are defined herein. Also provided are pharmaceutical compositions, kits and articles of manufacture comprising such pharmaceutical agents. Methods of using the pharmaceutical agents for the treatment of a variety of diseases and disorders are also provided.

20 Claims, 1 Drawing Sheet

(56) References Cited

FOREIGN PATENT DOCUMENTS

| WO | WO 2000/038719 | | 7/2000 | |
|---|---|---|---|---|
| WO | WO 2000/038786 | | 7/2000 | |
| WO | WO 2000/051686 | | 9/2000 | |
| WO | WO 2002/020020 | | 3/2002 | |
| WO | WO 2002/072106 | | 9/2002 | |
| WO | WO 2003/032961 | | 4/2003 | |
| WO | WO 2004/060376 | | 7/2004 | |
| WO | WO 2008/018827 | | 2/2008 | |
| WO | WO 2009/061448 A9 | | 5/2009 | |
| WO | WO 2010/010184 | | 1/2010 | |
| WO | WO 2010/048499 | | 4/2010 | |
| WO | WO 2010/104933 | | 9/2010 | |
| WO | WO 2011/025927 | | 3/2011 | |
| WO | WO 2012/027322 | | 3/2012 | |
| WO | WO 2013/033430 | | 3/2013 | |
| WO | WO 2014/015054 | | 1/2014 | |
| WO | WO2014015054 | * | 1/2014 | ........... C07D 403/12 |
| WO | WO 2016/172710 | | 10/2016 | |

OTHER PUBLICATIONS

Bax et al., "Cell adhesion to fibrillin-1 molecules and microfibrils is mediated by $\alpha_5\beta_1$ and $\alpha_v\beta_3$ integrins," J. Biol. Chem., 278(36):34605-34616, 2003.
Becker et al., "An expedient synthesis of 3-amino-5-hydroxybenzoic acid and its n-alkyl analogues," Tetrahedron, 39:4189-4192, 1983.
Bedke et al., "Anti-inflammatory effects of αV integrin antagonism in acute kidney allograft rejection," Am. J. Pathology, 171(4):1127-1139, 2007.
Bhaskar et al., "A function blocking anti-mouse integrin α5β1 antibody inhibits angiogenesis and impedes tumor growth in vivo," J. Transl. Med., 5:61, 2007.
Blase et al., "The capacity of human malignant B-lymphocytes to disseminate in SCID mice is correlated with functional expression of the fibronectin receptor $\alpha_5\beta_1$ (CD49e/CD29)," Int. J. Cancer, 60(6):860-866, 1995.
Carron et al., "A peptidomimetic antagonist of the integrin $\alpha_v\beta_3$ inhibits Leydig cell tumor growth and the development of hypercalcemia of malignancy," Cancer Res., 58:1930-1935, 1998.
Carron et al., "Peptidomimetic antagonists of αvβ3 inhibit bone resorption by inhibiting osteoclast bone resorptive activity, not osteoclast adhesion to bone," J. Endocrinol., 165:587-598, 2000.
Chai et al., "αv and β1 integrins regulate dynamic compression-induced proteoglycan synthesis in 3D gel culture by distinct complementary pathways," Osteoarthritis and Cartilage, 18:249-256, 2009.
Clark et al., "Pilot Plant Preparation of an $\alpha_v\alpha_3$ Integrin Antagonist. Part 1. Process Research and Development of a (S)-β-Amino Acid Ester Intermediate: Synthesis via a Scalable, Diastereoselective Imino-Reformatsky Reaction," Organic Process Research & Development, 8:51-61, 2004.
Clark et al., "Pilot-Plant Preparation of an $\alpha_v\beta_3$ Integrin Antagonist. Part 2. Synthesis of N-[2-(5-Hydroxy-4,6-tetrahydropyrimidine)]-3-amino-5-hydroxybenzoic Acid," Organic Process Research & Development, 8:571-575, 2004.
Clark et al., "Pilot-Plant Preparation of an $\alpha_v\beta_3$ Integrin Antagonist. Part 3. Process Research and Development of a Diisopropylcarbodiimide and Catalytic 1-Hydrobenzotriazole Peptide Coupling," Organic Process Research & Development, 13(6):1088-1093, 2009.
Collo, "Endothelial cell integrin α5β1 expression is modulated by cytokines and during migration in vitro," J. Cell Sci., 112(Pt 4):569-578, 1999.
Cue et al., "A nonpeptide integrin antagonist can inhibit epithelial cell ingestion of Streptococcus pyogenes by blocking formation of integrin α5β1-fibronectin-M1 protein complexes," Proc Natl Acad Sci USA, 97(6):2858-2863, 2000.

Danen et al., "Emergence of α5β1 fibronectin- and αvβ3 vitronectin-receptor expression in melanocytic tumour progression," Histopathology, 24(3):249-256, 1994.
Database Registry, "Rare Chemicals Catalogue", CAS Accession No. 773126-23-1, Published Feb. 5, 2013 in 4 pages.
Database Registry, "NetChem Product List"; CAS Accession No. 682803-43-6, Published Jun. 13, 2013 in 5 pages.
Database Registry, "Asiba Pharmatech Product List", CAS Accession No. 1270085-65-8, Published Jul. 30, 2013 in 2 pages.
Duggan et al., "Ligands to the integrin receptor $\alpha_v\beta_3$," Expert Opinion on Therapeutic Patents, 10(9):1367-1383, 2000.
Edward, "Integrins and other adhesion molecules involved in melanocytic tumor progression." Curr. Opin. Oneal., 7(2):185-191, 1995.
Engleman et al., "A Peptidomimetic Antagonist of the $\alpha_v\beta_3$ Integrin Inhibits Bone Resorption In Vitro and Prevents Osteoporosis In Vivo," J. Clin. Invest. 99:2284-2292, 1997.
Faulconbridge et al., "Preparation of enantiomerically enriched aromatic β-amino acids via enzymatic resolution," Tetrahedron Lett., 41:2679-2681, 2000.
Feng, et al., "Effects of Synthesized Peptide S247 on the Activation of P38MAPK During Ventilator-induced Lung Injury," Zhonghua Jizhen Yixue Zazhi, 15(7):603-607, 2006.
Ferrari et al., "VEGF, a prosurvival factor, acts in concert with TGF-β1 to induce endothelial cell apoptosis," Proc. Natl. Acad. Sci. USA, 103(46):17260-17265, 2006.
Gamlath, et al., "Synthesis, tissue distribution, and recovery of 14C labeled αVβ3 inhibitors" in Synthesis and Applications of Isotopically Labelled Compounds, vol. 8 (2004); Dean et al. [Eds.] John Wiley & Sons, Ltd., 6 pages.
Gao et al., "A novel integrin $\alpha_5\beta_1$ binding domain in module 4 of connective tissue growth factor (CCN2/CTGF) promotes adhesion and migration of activated pancreatic stellate cells." Gut, 55:856-862, 2006.
Gisch et al., "Enzymatically Activated cycloSal-d4T-monophosphates: The Third Generation of cycloSal-Pronucleotides," J. Med. Chem., 50:1658-1667, 2007.
Gisch et al., "Studies on Enzyme-Cleavable Dialkoxymethyl-cycloSaligenyl- 2',3'-dideoxy-2',3'-didehydrothymidine Monophosphates," J. Med. Chem., 51:6752-6760, 2008.
Goodman et al., "Nanomolar small molecule inhibitors for αvβ6, αvβ5, and αvβ3 integrins," J. Med. Chem., 45(5):1045-1051, 2002.
Griggs et al., "Characteristics of cation binding to the I domains of LFA-1 and MAC-1: The LFA-1 I Domain contains a $Ca^{2+}$-binding site," J. Biol. Chem., 273:22113-22119, 1998.
Griggs et al., "Promoter elements determining weak expression of the GAL4 regulatory gene of Saccharomyces cerevisiae," Mol. Cell. Biol., 13(8):4999-5009, 1993.
Griggs et al., "Regulated expression of the GAL4 activator gene in yeast provides a sensitive genetic switch for glucose repression," Proc. Natl. Acad. Sci., 88:8597-8601, 1991.
Gui, et al., "Role of Integrin αVβ6 in Ventilator-Induced Lung Injury in Rats," Zhonghua Mazuixue Zazhi, 28(2):163-166, 2008.
Harms et al., "A small molecule antagonist of the $\alpha_v\beta_3$ integrin suppresses MDA-MB-435 skeletal metastasis," Clin. Exp. Metastasis, 21:119-128, 2004.
Heckman et al., "Probing integrin selectivity: rational design of highly active and selective ligands for the α5β1 and αvβ3 integrin receptor," Angew Chem Int Ed Engl., 46(19):3571-3574, 2007.
Heckman et al., "Rational design of highly active and selective ligands for the α5β1 integrin receptor," ChemBioChem., 9(9):1397-1407, 2008.
Henderson et al., "Selective αv integrin deletion identifies a core, targetable molecular pathway that regulates fibrosis across solid organs," Nature Medicine, 19(12):1617-1624 and Suppl. Information in 3 pages, 2013.
Herlt et al., "Synthesis of unlabeled and carboxyl-labelled 3-amino-5-hydroxybenzoic acid," Austr. J. Chem., 34(6):1319-1324, 1981.
Hippenmeyer et al., "Adenovirus inhibition by peptidomimetic integrin antagonists," Antiviral Res., 55:169-178, 2002.
Horan et al., "Partial inhibition of integrin αvβ6 prevents pulmonary fibrosis without exacerbating inflammation," Am. J. Respir. Crit. Care Med., 177(1):56-65, 2008.

(56) References Cited

OTHER PUBLICATIONS

Huang et al., "Direct Trifluoromethylation of Nitriles Promoted by Tetrabutylammonium Bifluoride," Synlett,, 15:2518-2520, 2009.
Jørgensen, et al., "Efficient Synthesis of α-Aryl Esters by Room-Temperature Palladium-Catalyzed Coupling of Aryl Halides with Ester Enolates," J. Am. Chem. Soc., 124(42):12557-12565, 2002.
Kapp et al., "Integrin modulators: a patent review," Expert Opinion on Therapeutic Patents, 23(10): 1273-1295, 2013.
Kim et al., "Regulation of angiogenesis in vivo by ligation of integrin α5β1 with the central cell-binding domain of fibronectin," Am. J. Pathol., 156(4):1345-1362, 2000.
Kurahashi et al., "One-Electron Oxidation of Electronically Diverse Manganese(III) and Nickel(II) Salen Complexes: Transition from Localized to Delocalized Mixed-Valence Ligand Radicals," J. Am. Chem. Soc., 133(21):8307-8316, 2011.
Landis et al., "Kinetic Resolution of α-Amino Esters by Acylation Using Immobilized Penicillin Amidohydrolase," Organic Process Research & Development, 6:539-546, 2002.
Li et al., "Integrin α5β1 mediates attachment, migration, and proliferation in human retinal pigment epithelium: relevance for proliferative retinal disease." Invest. Ophthalmol. Vis. Sci., 50(12):5988-5996, 2009.
Livant et al., "The PHSRN sequence induces extracellular matrix invasion and accelerates wound healing in obese diabetic mice." J. Clin. Invest. 105(11):1537-1545, 2000.
Lobert et al., "Ubiquitination of α5β1 integrin controls fibroblast migration through lysosomal degradation of fibronectin-integrin complexes," Dev. Cell, 19(1):148-159, 2010.
Malfait et al., "Proprotein convertase activation of aggrecanases in cartilage in situ," Arch. Biochem. Biophys., 478(1):43-51, 2008.
Melton et al., "Expression of $α_vβ8$ integrin on dendritic cells regulates Th17 cell development and experimental autoimmune encephalomyelitis in mice." J. Clin. Invest., 120(12):4436-4444, 2010.
Millard et al., "Integrin targeted therapeutics." Theranostics, 1:154-88, 2011.
Mu et al., "The integrin αvβ8 mediates epithelial homeostasis through MT1-MMP-dependent activation of TGF-β1," Cell Biol., 157(3):493-507, 2002.
Munger et al., "Interactions between growth factors and integrins: latent forms of transforming growth factor-β are ligands for the integrin αvβ1," Mol. Biol. Cell, 9:2627-2638, 1998.
Munger et al., The Integrin αvβ6 Binds and Activates Latent TGFβ1: A Mechanism for Regulating Pulmonary Inflammation and Fibrosis, Cell 96(3):319-328, 1999.
Nagarajan et al., "Discovery of diphenylmethanepropionic and dihydrostilbeneacetic acids as antagonists of the integrin αvβ3," Chem. Biol. Drug Des., 67:177-181, 2006.
Nagarajan et al., "R-isomers of Arg-Gly-Asp (RGD) mimics as potent αvβ3 inhibitors," Bioorganic & Medicinal Chemistry, 15(11):3783-3800, 2007.
Nandrot et al., "Novel role for $a_vβ_5$-integrin in retinal adhesion and its diurnal peak," Am J Physiol Cell Physiol, 290(4):C1256-C1262, 2006.
Nishimura, "Integrin-mediated transforming growth factor-β activation, a potential therapeutic target in fibrogenic disorders." Am. J. Pathol., 175(4):1362-1370, 2009.
Nomura et al., "Stereoselective Ring-Opening Polymerization of a Racemic Lactide by Using Achiral Salen- and Homosalen-Aluminum Complexes," Chemistry—A Europ. J., 13(16):4433-4451, 2007.
Nordstrom, et al., "Analysis of Solution Nonideality of pseudomorphic drug system through comprehensive thermodynamic framework for the design of a crystallization process," J. Pharmaceutical Sciences, 93(4):995-1004, 2004.

Perdih, "Small molecule antagonists of integrin receptors," Curr. Med. Chem., 17(22):2371-2392, 2010.
Popov et al., "Integrin αvβ6 is a marker of the progression of biliary and portal liver fibrosis and a novel target for antifibrotic therapies," J. Hepatol., 48(3):453-464, 2008.
Reinmuth, et al., "$α_{vβ3}$ Integrin Antagonist S247 Decreased Colon Cancer Metastasis and Angiogenesis and Improved Survival in Mice," Cancer Research, 63(9):2079-2087, 2003.
Rico, "Synthesis of novel β-amino acid precursors: β-aminohydrocoumarins as unusual aspartic acid mimetics used in fibrinogen receptor antagonists," Tetrahedron Lett. 35(36):6599-6602, 1994.
Schmidt et al., "Characterization of spontaneous metastasis in an aggressive breast carcinoma model using flow cytometry," Clin. Exp. Metastasis, 17:537-544, 1999.
Scotton et al., "Increased local expression of coagulation factor X contributes to the fibrotic response in human and murine lung injury," J. Clin. Invest. 119(9):2550-2563, 2009.
Shannon et al., "Anti-metastatic properties of RGD-peptidomimetic agents S137 and S247," Clin. Exp. Metastasis, 21:129-138, 2004.
Song et al., "Aggrecan degradation in human articular cartilage explants is mediated by both ADAMTS-4 and ADAMTS-5," Arthritis Rheum., 56:575-585, 2007.
Stragies et al., "Design and synthesis of a new class of selective integrin α5β1 antagonists," J. Med. Chem., 50(16):3786-3794, 2007.
Suehiro et al., "Fibrinogen binds to integrin $α_5β_1$ via the Carboxyl-Terminal RGD Site of the Aα-Chain," J. Biochem., 128(4):705-710, 2000.
Tanaka et al., "Synthesis of aromatic compounds containing a 1,1-dialkyl-2-trifluoromethyl group, a bioisostere of the tert-alkyl moiety," Bioorg. Med. Chem. Lett., 17(22):6079-6085, 2007.
Vellon et al., "$α_vβ_3$ integrin regulates heregulin (HRG)-induced cell proliferation and survival in breast cancer," Oncogene, 24(23):3759-3773, 2005.
Wan, et al., "Synthesis of Potent and Orally Efficacious 11β-Hydroxysteroid Dehydrogenase Type 1 Inhibitor HSD-016," J. Org. Chem., 76(17):7048-7055, 2011.
Wipff et al., "Myofibroblast contraction activates latent TGF-β1 from the extracellular matrix." J. Cell Biol., 179(6):1311-1323, 2007.
Wong et al., "αv Integrins mediate adhesion and migration of breast carcinoma cell lines," Clin. Exp. Metastasis, 16:50-61, 1998.
Wu et al., "Mild Palladium-Catalyzed Selective Monoarylation of Nitriles," J. Am. Chem. Soc., 127(45):15824-15832, 2005.
Wu et al., "Expression of integrin $α_vβ_6$ in rats with ventilator-induced lung injury and the attenuating effect of synthesized peptide S247," Medical Science Monitor, 14(2):BR41-BR48, 2008.
Yang et al., "Embryonic mesodermal defects in $α_5$ integrin-deficient mice," Development, 119(4):1093-1105, 1993.
Yoshimura et al., "TGF-β function in immune suppression," Curr. Top. Microbiol Immunol., 350:127-147, 2011.
Zack et al., "ADAM-8 isolated from human osteoarthritic chondrocytes is capable of cleaving fibronectin at Ala[271]," Arthritis Rheum., 60:2704-2713, 2009.
Zahn et al., "Assessment of the integrin α5β1 antagonist JSM6427 in proliferative vitreoretinopathy using in vitro assays and a rabbit model of retinal detachment," Invest. Ophthalmol. Vis. Sci., 51(2)1028-1035, 2010.
Zahn et al., "Preclinical evaluation of the novel small-molecule integrin α5β1 inhibitor JSM6427 in monkey and rabbit models of choroidal neovascularization," Arch Ophthalmol., 127(10):1329-1335, 2009.
International Search Report issued in International Application No. PCT/US2016/069511, dated Mar. 22, 2017.

* cited by examiner

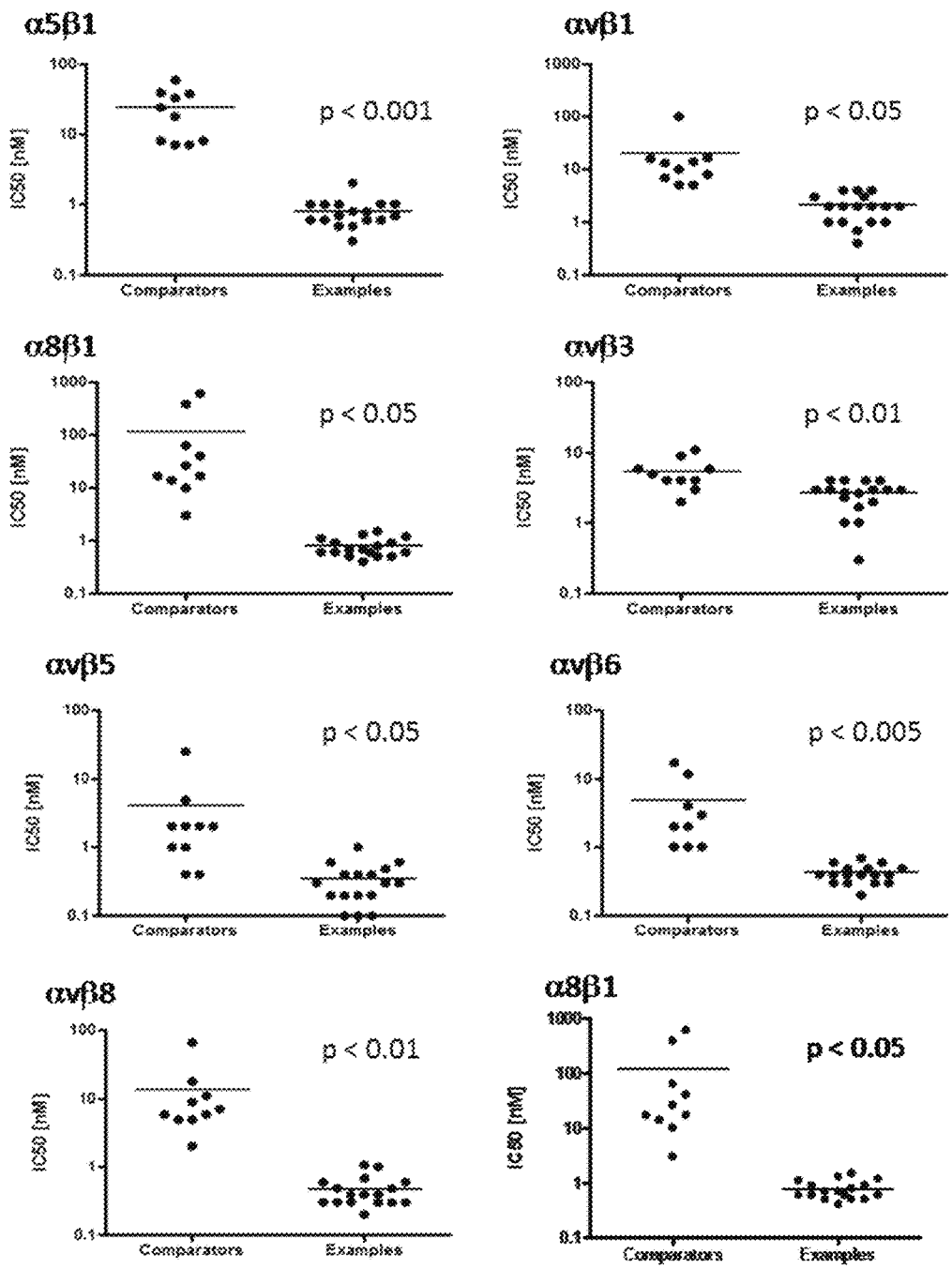

META-AZACYCLIC AMINO BENZOIC ACID DERIVATIVES AS PAN INTEGRIN ANTAGONISTS

CROSS-REFERENCE TO RELATED APPLICATIONS

Any and all priority claims identified in the Application Data Sheet, or any correction thereto, are hereby incorporated by reference under 37 CFR 1.57.

BACKGROUND

I. Field of the Invention

The present disclosure relates to the fields of pharmaceuticals, medicine and cell biology. More specifically, it relates to pharmaceutical agents (compounds) which are useful as integrin receptor antagonists, with biological activity as antagonists of one or more integrins that mediate the pathologic processes of angiogenesis and fibrosis. As such, these compounds may be used are useful in pharmaceutical compositions and in methods for treating diseases and disorders, including conditions mediated by one or more of such integrins.

II. Description of Related Art

Integrins are a family of integral cytoplasmic membrane proteins that mediate cell interactions with other cells and with the extracellular matrix. Approximately one third of the members of the integrin family directly bind to a specific amino acid motif, arginine-glycine-aspartate (RGD), that is contained within the sequence of their cognate protein ligands. It has been established in the art that peptides containing the RGD sequence, and synthetic small molecule compounds that mimic the RGD sequence, are capable of binding to these integrin receptors with varying degrees of specificity, and thereby inhibit the binding to normal physiologic ligands (Millard, 2011; Sun et al., 2014). The biological effects of treatment with such agents is dependent on intrinsic molecular properties, reflected in the structure, that determine to what degree a particular integrin, or combination of integrins, is inhibited in a body tissue over a period of time.

Many human diseases are characterized by either or both of two common contributing pathological mechanisms: angiogenesis and fibrosis. Different subsets of the RGD-binding integrins have predominant roles in driving these dual processes, so that simultaneous antagonism of angiogenesis and fibrosis requires agents capable of binding potently to several target integrins. This contrasts with agents designed specifically for binding to a single integrin which may be less effective in some applications due to their more restricted mechanism of action.

Integrins which have been shown to have a role in promoting angiogenesis include $\alpha v\beta 3$, $\alpha v\beta 5$, and $\alpha 5\beta 1$. $\alpha v\beta 3$ and $\alpha v\beta 5$ were initially described as mediators of bFGF- and VEGF-induced angiogenesis, respectively, in corneal or chorioallantoic models. Subsequent data from studies using mice lacking these integrins also support an important functional role for $\alpha 5\beta 1$. The integrin $\alpha 5\beta 1$ (also known as VLA-5) is often referred to as the 'classic fibronectin receptor' reflecting its well characterized interaction with this extracellular matrix protein. Cells expressing $\alpha 5\beta 1$ bind to fibronectin in a region that incorporates the ninth and tenth type III fibronectin repeats, the latter of which contains the RGD motif critical for integrin binding. In addition to fibronectin, $\alpha 5\beta 1$ has been reported to interact with other RGD-containing extracellular matrix proteins including fibrinogen, denatured collagen, and fibrillin-1 (Bax et al., 2003; Perdih, 2010; Suehiro et al., 2000). These ligands are components of the provisional matrix that is laid down by cells as part of the wound healing response in tissues. Key components of this response are angiogenesis (new blood vessel formation) and fibrosis (scar formation) which are beneficial for healing of acute injuries, but can be deleterious in many disease contexts.

Antagonists of RGD-binding integrins should be useful for treatment of human diseases having angiogenesis or fibrosis as a principal part of their pathology. In particular, the important role of $\alpha 5\beta 1$ in angiogenesis is supported by numerous studies. For example, mice lacking this integrin exhibit embryonic lethality at day 10-11 with a phenotype that includes defects in both the embryonic and extraembryonic vasculature (Yang et al., 1993). Angiogenic cytokines such as bFGF, IL-8, TGFβ, and TNFα upregulate $\alpha 5\beta 1$ expression on endothelial cells in vitro and in vivo, and immunohistochemistry shows coordinated increases in both $\alpha 5\beta 1$ and fibronectin staining in blood vessels from various types of human tumor biopsies and xenograft tumors in animals (Collo, 1999; Kim et al., 2000). Monoclonal antibodies that specifically inhibit $\alpha 5\beta 1$, and compounds that have been described as $\alpha 5\beta 1$ inhibitors, significantly reduce angiogenesis in a number of experimental models (Kim et al., 2000; Bhaskar et al., 2007; Livant et al., 2000; Zahn et al., 2009).

Because $\alpha 5\beta 1$ expression is not confined to the endothelium, it has other functional roles in addition to angiogenesis. It is expressed to varying degrees in many cell types including fibroblasts, hematopoietic and immune cells, smooth muscle cells, epithelial cells, and tumor cells. Expression on tumor cells has been implicated in the progression of tumor growth and metastasis (Adachi et al., 2000; Blasé et al., 1995; Danen et al., 1994; Edward, 1995). In human fibroblasts, $\alpha 5\beta 1$ promotes motility and survival (Lobert et al., 2010). In pancreatic stellate cells, it interacts with connective tissue growth factor to stimulate adhesion, migration, and fibrogenesis (Gao and Brigstock, 2006). It has been shown that pharmacologic antagonism of $\alpha 5\beta 1$ inhibits the attachment migration, and proliferation of human retinal epithelial cells in vitro, and reduces retinal cell proliferation and scarring when administered intravitreally to rabbits with retinal detachment (Li et al., 2009; Zahn et al., 2010).

Besides $\alpha 5\beta 1$, another RGD-binding integrin of the beta-1 family that is upregulated after organ injury is $\alpha 8\beta 1$. Studies have shown that this integrin is co-expressed with markers of tissue myofibroblasts, the principal cellular mediators of fibrosis (Levine et al., 2000; Bouzeghrane et al., 2004). Ectopic expression of $\alpha 8\beta 1$ conferred to cells increased spreading and adhesion on latent TGFβ, a major pro-fibrotic cytokine, in a manner that was RGD-dependent (Lu et al., 2002).

RGD-binding integrins of the alpha v family have been implicated in promoting the biological activation of the latent pro-fibrotic cytokine TGFβ. This is mediated by binding to the latency associated peptide (LAP), particularly by $\alpha v\beta 6$ and $\alpha v\beta 8$, but also by $\alpha v\beta 1$, $\alpha v\beta 3$, and $\alpha v\beta 5$. Furthermore, the alpha v integrins mediate attachment, migration, proliferation and other functions in diverse cell types associated with the wound repair process. This functional redundancy, differential cellular expression, and the known fibrosis phenotypes of integrin knockout mice, all suggest that a highly potent antagonist of this entire subset may be particularly useful for therapeutic development. To achieve TGFβ activation, these integrins are all critically dependent upon the amino acid sequence arg-gly-asp (RGD) contained in LAP. Indeed, mice containing a mutation in the RGD sequence of LAP are incapable of TGFβ activation and recapitulate the phenotype of TGFβ-null mice. Genetic ablation of the expression of alpha v integrins specifically from myofibroblasts in mice conferred protection against the development of fibrosis in several models of organ injury, and this efficacy was similarly provided by continuous infusion treatment with a small molecule integrin antagonist of RGD-binding integrins known as CWHM-12 (Henderson et al., 2013). Such studies support the concept that simultaneous inhibition of multiple integrins may have particular utility to prevent or treat a range of fibrotic conditions.

The multi-integrin receptor antagonist compounds previously described in the art generally lack either demonstrated broad spectrum potency against all of the RGD integrins described above, or the pharmacokinetic properties suitable for sustained activity with oral dosing, or both. Long plasma half-life at therapeutically significant concentrations following oral administration is a highly desirable property for development of drug formulations for clinical treatments, allowing convenient administration usually without need for medical supervision.

SUMMARY

The present disclosure provides novel integrin receptor antagonists, pharmaceutical compositions thereof, methods of manufacture thereof, and methods for their use.

In some aspects, the present disclosure provides compounds of the formula:

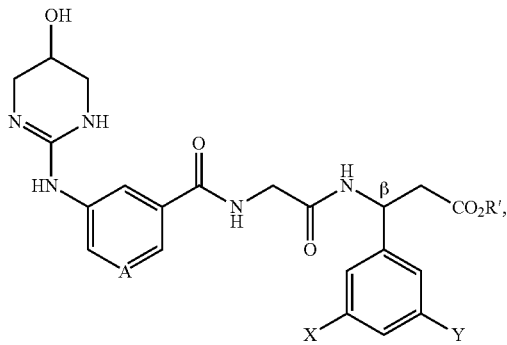

(I)

wherein:
A is C—H, C—OH, or N;
R' is hydrogen, alkyl$_{(C\leq 8)}$, substituted alkyl$_{(C\leq 8)}$, or a substituent convertible in vivo to hydrogen; and
X and Y are each independently cyano, halo, fluoroalkoxy$_{(C1-2)}$, alkyl$_{(C1-2)}$, or fluoroalkyl$_{(C1-2)}$, with the proviso that X and Y are not both cyano or alkyl$_{(C1-2)}$;
or a pharmaceutically acceptable salt or tautomer of the above formula.

In some embodiments, the compound is further defined as:

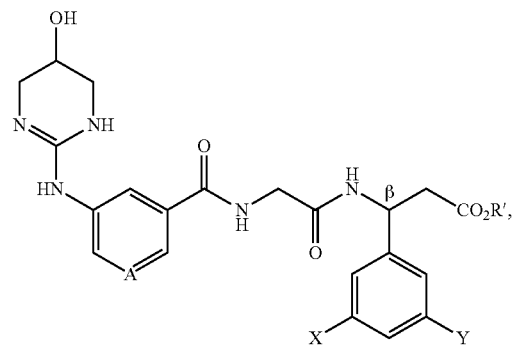

(I)

wherein:
A is C—OH or N;
R' is hydrogen, alkyl$_{(C\leq 8)}$, substituted alkyl$_{(C\leq 8)}$, or a substituent convertible in vivo to hydrogen; and
X and Y are each independently cyano, halo, fluoroalkoxy$_{(C1-2)}$, alkyl$_{(C1-2)}$, or fluoroalkyl$_{(C1-2)}$, with the proviso that X and Y are not both cyano or alkyl$_{(C1-2)}$;
or a pharmaceutically acceptable salt or tautomer of the above formula.

In some embodiments, A is N. In other embodiments, A is C—OH. In some embodiments, R' is hydrogen.

In some embodiments, X is halo such as —F, —Cl, or —Br. In some embodiments, X is —F. In other embodiments, X is —Cl. In other embodiments, X is —Br. In other embodiments, X is fluoroalkoxy$_{(C1-2)}$ such as —OCF$_3$. In other embodiments, X is fluoroalkyl$_{(C1-2)}$. In some embodiments, X is —CHF$_2$. In other embodiments, X is —CF$_3$. In other embodiments, X is alkyl$_{(C1-2)}$ such as —CH$_3$.

In some embodiments, Y is halo such as —F, —Cl, or —Br. In some embodiments, Y is —F. In other embodiments, Y is —Cl. In other embodiments, Y is —Br. In other embodiments, Y is fluoroalkoxy$_{(C1-2)}$ such as —OCF$_3$. In other embodiments, Y is fluoroalkyl$_{(C1-2)}$. In some embodiments, Y is —CHF$_2$. In other embodiments, Y is —CF$_3$. In other embodiments, Y is alkyl$_{(C1-2)}$ such as —CH$_3$.

In some embodiments, X and Y are each independently selected from the groups consisting of —F, —Cl, —Br, —OCF$_3$, —CH$_3$, —CHF$_2$, and —CF$_3$, with the proviso that X and Y are not both —CH$_3$.

In some embodiments, the carbon atom labeled β is in the S configuration. In some embodiments, the compounds are further defined as:

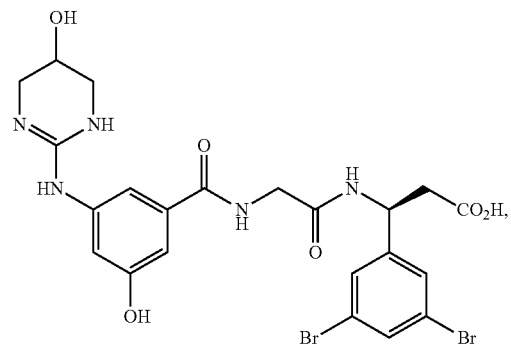

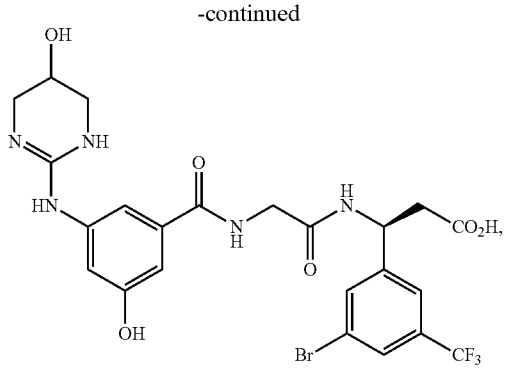
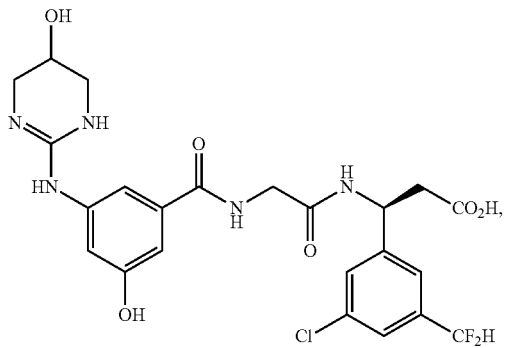
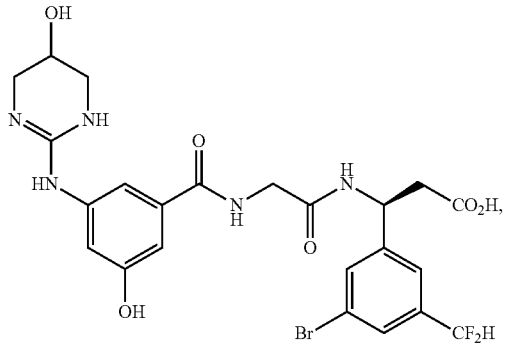
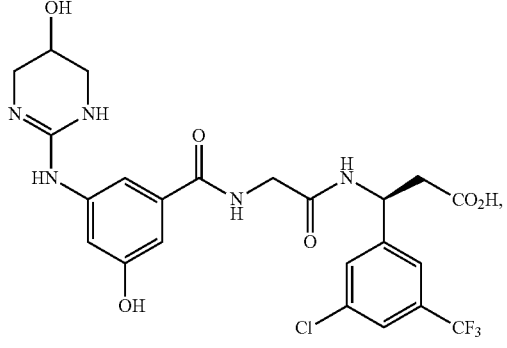
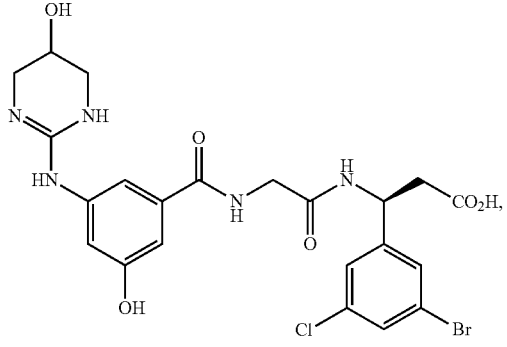
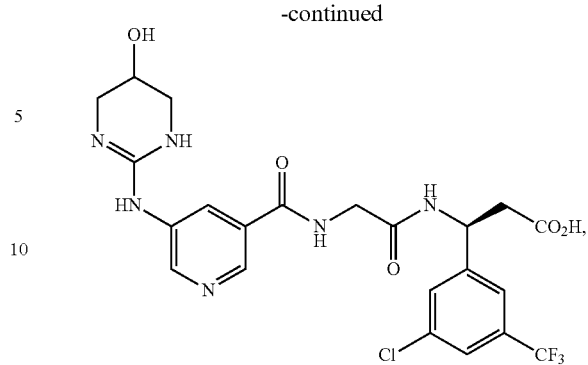
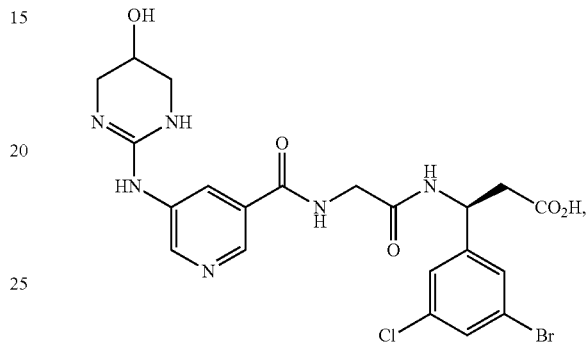
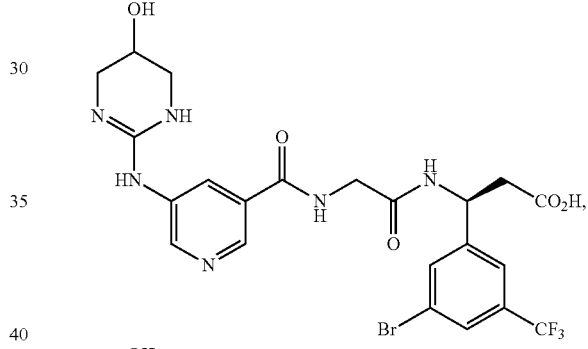
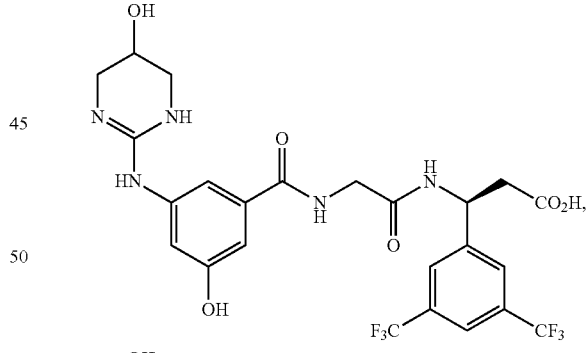
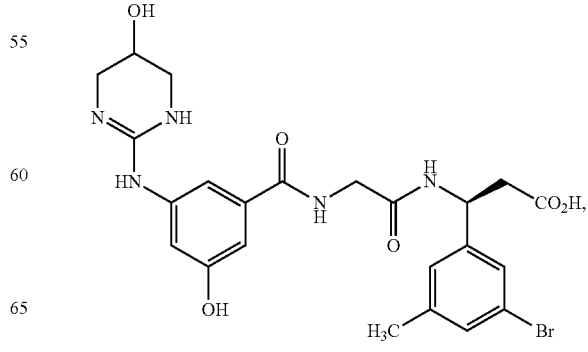

-continued

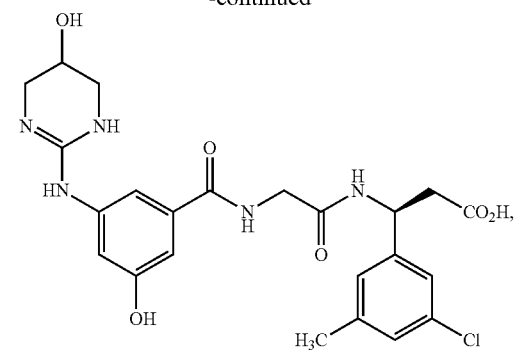
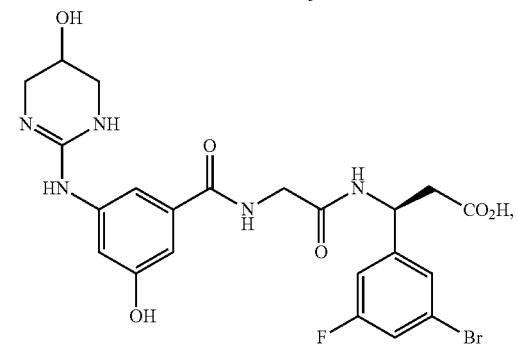
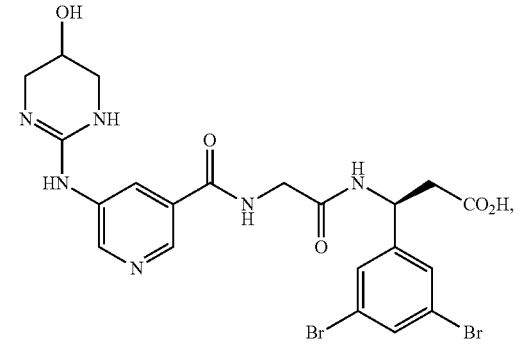
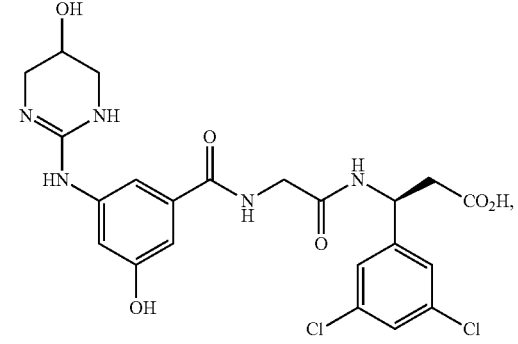
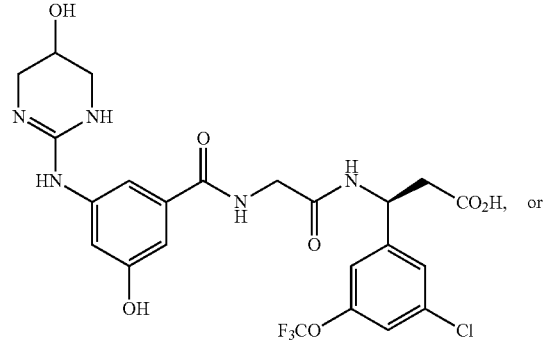

-continued

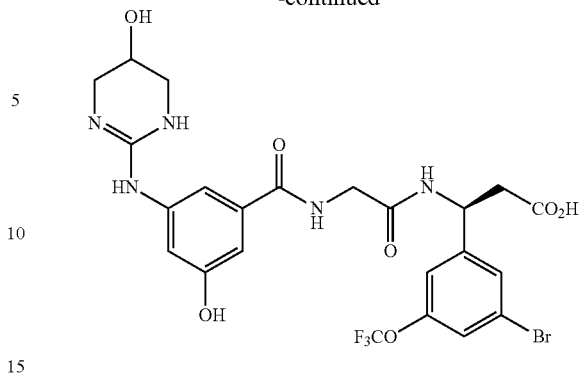

or a pharmaceutically acceptable salt or tautomer of any of the above formulas.

In some embodiments, the compounds are effective for inhibiting three or more RGD integrins selected from the group consisting of α5β1, αvβ1, α8β1, αvβ3, αvβ5, αvβ6, and αvβ8, wherein the effectiveness of the compound corresponds to an $IC_{50}$ value of less than 10 nM for each of the three or more RGD integrins as measured using a solid phase receptor assay (SPRA) for function of the respective integrin.

In some embodiments, the compounds possess pharmacokinetic properties that allow therapeutically significant plasma concentrations to be achieved and/or sustained in a patient for two or more hours after oral administration. In some embodiments, the compounds have a sustained plasma half-life of at least two hours as measured in a rat using an i.v. bolus comprising 1 mg of compound per kg of rat.

In yet another aspect, the present disclosure provides pharmaceutical compositions comprising:
 a) a compound described herein; and
 b) an excipient.

In still yet another aspect, the present disclosure provides methods of treating and/or preventing a disease or a disorder in a patient in need thereof, comprising administering to the patient a compound or composition described herein in an amount sufficient to treat and/or prevent the disease or disorder.

In some embodiments, the disease or disorder is associated with angiogenesis. In other embodiments, the disease or disorder is associated with fibrosis. In some embodiments, the disease or disorder is associated with fibrosis and/or angiogenesis.

In some embodiments, the disease or disorder is pulmonary, liver, renal, cardiac, and pancreatic fibrosis, scleroderma, scarring, retinopathy of prematurity, familial exudative vitreoretinopathy, proliferative vitreoretinopathies, macular degeneration, diabetic retinopathy, cancer, osteoporosis, autoimmune diseases, humoral hypercalcemia of malignancy, Paget's disease, periodontal disease, psoriasis, arthritis, restenosis, and infection. In some embodiments, the disease or disorder is pulmonary fibrosis. In other embodiments, the disease or disorder is liver fibrosis. In other embodiments, the disease or disorder is cardiac fibrosis. In other embodiments, the disease or disorder is renal fibrosis. In other embodiments, the disease or disorder is pancreatic fibrosis.

In other embodiments, the disease or disorder is scleroderma. In other embodiments, the disease or disorder is scarring. In some embodiments, the scarring is dermal scarring. In other embodiments, the scarring is retinal scarring. In other embodiments, the scarring is corneal scarring.

In other embodiments, the disease or disorder is retinopathy of prematurity. In other embodiments, the disease or disorder is familial exudative vitreoretinopathy. In other embodiments, the disease or disorder is proliferative vitreoretinopathies. In other embodiments, the disease or disorder is macular degeneration. In other embodiments, the disease or disorder is diabetic retinopathy.

In other embodiments, the disease or disorder is cancer. In some embodiments, the cancer includes solid tumor growth or neoplasia. In some embodiments, the cancer includes tumor metathesis. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is a carcinoma, sarcoma, lymphoma, leukemia, melanoma, mesothelioma, multiple myeloma, or seminoma.

In other embodiments, the disease or disorder is osteoporosis. In other embodiments, the disease or disorder is an autoimmune disease. In some embodiments, the autoimmune disorder is multiple sclerosis. In other embodiments, the disease or disorder is humoral hypercalcemia of malignancy. In other embodiments, the disease or disorder is Paget's disease. In other embodiments, the disease or disorder is periodontal disease. In other embodiments, the disease or disorder is psoriasis. In other embodiments, the disease or disorder is arthritis. In some embodiments, the arthritis is rheumatoid arthritis. In other embodiments, the disease or disorder is restenosis. In other embodiments, the disease or disorder is an infection.

In some embodiments, the patient is a human, monkey, cow, horse, sheep, goat, dog, cat, mouse, rat, guinea pig, or transgenic species thereof. In some embodiments, the patient is a monkey, cow, horse, sheep, goat, dog, cat, mouse, rat, or guinea pig. In some embodiments, the patient is a human.

In some aspects, the present disclosure contemplates the fact that the bond between the phenyl ring and the amino acid backbone on the β-amino acid is freely rotating. As such, in some aspects, it is contemplated that the structure may rotate such that the X group is on the oriented towards the backbone and the Y is oriented away form the backbone as well as the manner drawn in most commonly in the specification showing the X group on the oriented towards the backbone and the Y oriented away from the backbone as shown in the structures below. The structure:

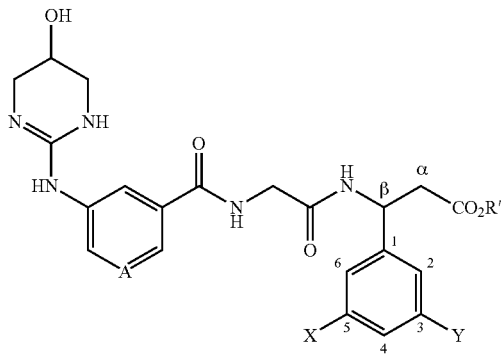

is equivalent to the structure:

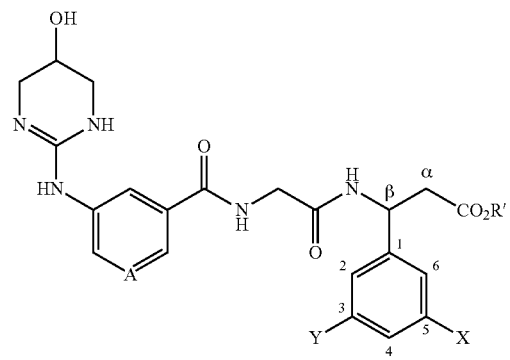

given the free rotation of the bond joining the carbon label β in the backbone and the carbon labeled 1 in the aromatic ring.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGURE—Dot plots comparing potency of comparison compounds (comparators) and Examples shown in Tables 1A & B for each integrin. Horizontal lines indicate group means. Statistical analysis was performed using a two-tailed standard T test for comparison of group means.

DESCRIPTION OF ILLUSTRATIVE EMBODIMENTS

Disclosed herein are new compounds and compositions with integrin receptor antagonists properties, methods for their manufacture, and methods for their use, including for the treatment and/or prevention of disease.

I. Compounds and Synthetic Methods

The compounds provided by the present disclosure may be made using the methods outlined below and further described in the Examples section. Comparison compounds shown in Table 1 and listed in Tables 3-5 were synthesized as disclosed in the literature. Additionally, these comparison compounds may also be readily synthesized by utilizing the methods and procedures described herein by those skilled in the art. General synthetic sequences for preparing the compounds useful in the present disclosure are outlined in Schemes I-VIII. Both an explanation of, and the actual procedures for, the various aspects of the present disclosure are described where appropriate. The following Schemes and Examples are intended to be merely illustrative of the present disclosure, and not limiting thereof in either scope or spirit. Those with skill in the art will readily understand that known variations of the conditions and processes described in the Schemes and Examples can be used to synthesize the compounds of the present disclosure. Starting materials and equipment employed were either commercially available prepared by methods previously reported and readily duplicated by those skilled in the art.

reduction of the corresponding nitro benzoic (or pyridine) acid, which can be obtained commercially or synthesized by nitration of the appropriate benzoic (or pyridine) acid, followed by reduction to the desired amino benzoic (or pyridine) acid, or by other reported methodologies that are known to those skilled in the art. This thiourea intermediate is converted to the S-methyl derivative by reaction with methyl iodide in ethanol at reflux. The appropriate 1,3-diamino-2-hydroxy propane is reacted with this resulting

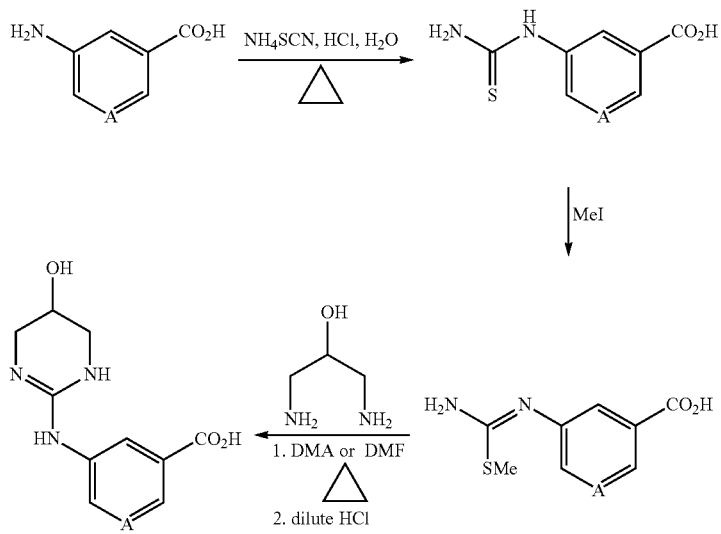

Scheme I illustrates general methodology which may be used for preparing the cyclic guanidine substituted left hand side aromatic acid portion of Formula I of the present disclosure which can then be coupled to a Gly-β-amino acid ester, or to Gly ester first, followed by (after ester hydrolysis) coupling to the appropriate β-amino acid ester. Briefly, in Scheme I, the appropriate amino benzoic (or pyridine) acid is reacted with ammonium thiocyanate in hot dilute hydrochloric to give the resulting 3-thiourea benzoic (or pyridine) acid after normal work-up. The starting amino benzoic (or pyridine) acids are either commercially available or can be converted to such amino benzoic (or pyridine) acids via intermediate in hot DMA (or DMF). Upon cooling, a precipitate forms and the zwitterionic product is isolated by filtration. The HCl salt may be obtained by lyophilizing from dilute hydrochloric acid. Alternatively, the product may be isolated from the original reaction mixture by removing volatiles and concentrating. The resulting product is taken up in water and pH adjusted to about 5-7 where zwitterionic product precipitates and is isolated by filtration. The HCl salt may be obtained as previously stated or by simply dissolving in dilute hydrochloric acid and concentrating to a solid and drying.

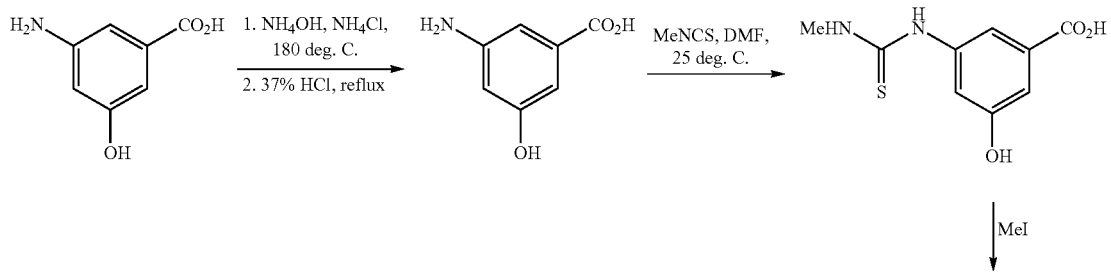

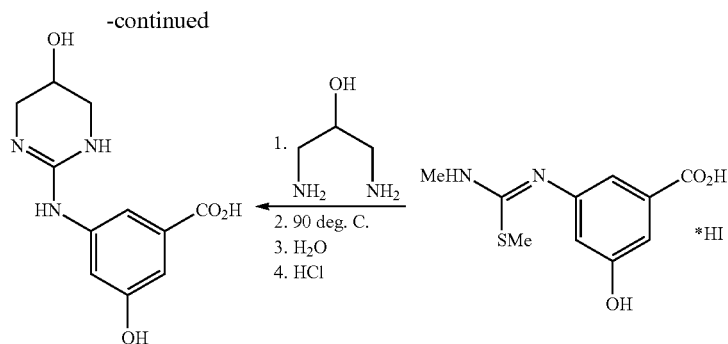

Scheme II illustrates methodology which may be used for preparing the tetrahydropyrimidinobenzoic acid portion of Formula I of the present disclosure which can then be coupled to a Gly-β-amino acid ester, or to Gly ester first, followed by (after ester hydrolysis) coupling to the appropriate β-amino acid ester. Briefly, in Scheme II, 3,5-dihydroxybenzoic acid is converted to 3-amino-5-hydroxy-benzoic acid using the procedure described in *Austr. J. Chem.* 1981 or Becker et al., 1983. The product is reacted with methyl isothiocyanate in DMF at room temperature (*Organic Process Research & Development*, 2004) to give 3-N'-methyl thiourea-5-hydroxybenzoic acid after normal work-up. This thiourea intermediate is converted to the S-methyl derivative by reaction with methyl iodide neat at below 40° C. 1,3-diamino-2-hydroxypropane is reacted with this resulting intermediate in hot DMA (or DMF). Upon cooling, a precipitate forms and the zwitterionic product is isolated by filtration. The HCl salt may be obtained by lyophilizing from dilute hydrochloric acid. Alternatively, the product may be isolated from the original reaction mixture by removing volatiles and concentrating. The resulting product is taken up in water and pH adjusted to about 5-7 where zwitterionic product precipitates and is isolated by filtration. The HCl salt may be obtained as previously stated or by simply dissolving in dilute hydrochloric acid and concentrating to a solid and drying.

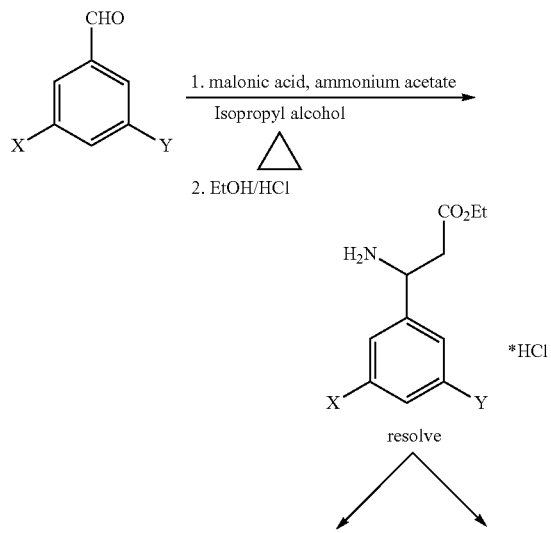

Scheme III illustrates a general methodology which may be used for the synthesis of the beta amino acid ester portion of Formula I of the present disclosure, starting from an appropriate benzaldehyde. This beta amino acid ester can then be coupled to Boc-Glycine followed by (after removal of the Boc protecting group) coupling to the appropriate aromatic acid described in Schemes I and II, or to the aromatic acid that has been coupled to Glycine. Briefly in Scheme III, to the appropriate benzaldehyde in isopropanol is added ammonium acetate followed by malonic acid. The reaction mixture is stirred at reflux, the resulting precipitate filtered and washed with hot isopropanol and dried to yield the desired racemic beta amino acid. The ethyl ester is synthesized by heating this acid in excess ethanol in the presence of excess HCl gas. These racemic beta amino acid esters can be resolved into the (R) and the (S) enantiomers via chiral chromatographic separation, or via enzymatic resolution as described in Faulconbridge et al., 2000 or Landis et al., 2002, which are incorporated herein by reference. In some embodiments, the (S) enantiomer is the preferred enantiomer of the β-amino acid group.

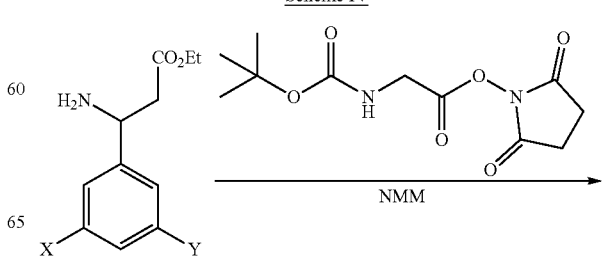

15

-continued

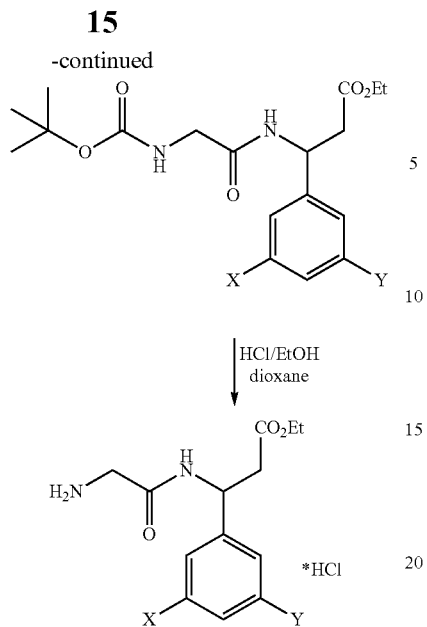

Scheme IV illustrates a general methodology which may be used for preparing the ethyl-N-Gly-beta amino acid portion of Formula I of the present disclosure, which can be coupled to the aromatic acid portion of Formula I described in Schemes I and II. This method describes coupling a beta amino acid ester to Glycine. Briefly, the desired beta amino acid ester (described in Scheme III above) is treated with activated Boc Glycine. Removal of the Boc protective group (by treatment with ethanol/HCl, for example) affords the Glycine amide of the corresponding beta amino acid ester (the (S) enantiomer is afforded by utilizing the (S)-beta amino acid ester, described in the above scheme).

Scheme V

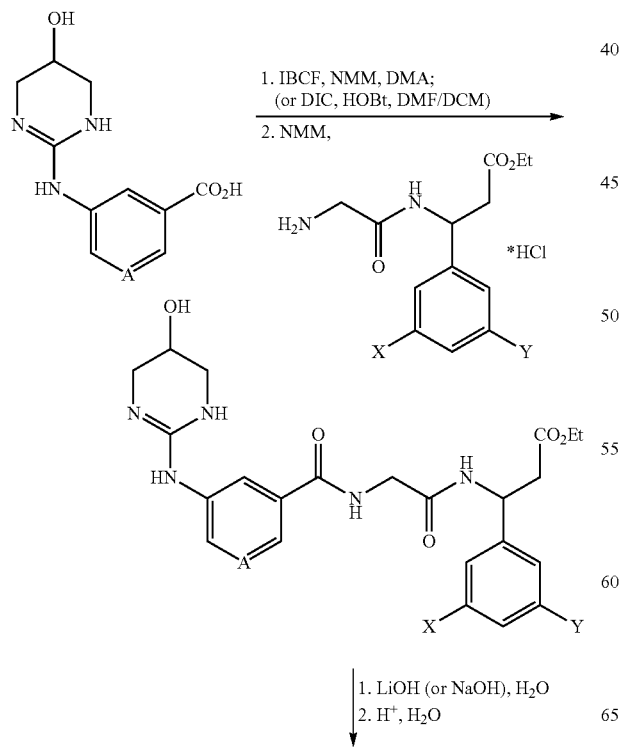

16

-continued

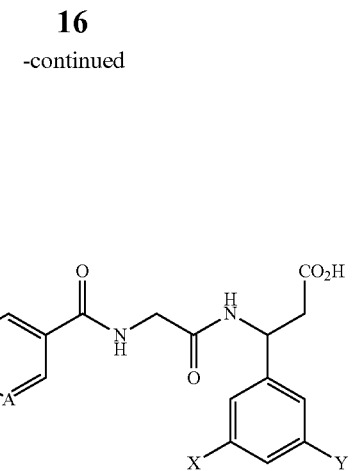

Scheme V illustrates a general methodology which may be used for preparing various compounds of the present disclosure. Briefly, the cyclic guanidine substituted left hand side aromatic acid portion of Formula I (described in Schemes I and II) is activated for coupling using known methods. Thus, after dissolving in a suitable solvent such as DMA an equivalent of NMM is added. The reaction mixture is cooled to ice-bath temperatures and IBCF added. To the mixed anhydride intermediate is added the Gly-β-amino acid ester (described in Scheme IV) and NMM. Upon completion of the reaction the product is purified by preparative HPLC and the ester hydrolyzed to the acid by treating with a base, such as LiOH in a suitable solvent (dioxane/water or acetonitrile/water). Alternatively, a suitable acid, such as TFA can be used. The product is isolated by preparative HPLC or by isolating the zwitterion at pH 5-7 and converting to the desired salt by standard procedures. (The (S) enantiomer is afforded by utilizing the (S) beta amino acid ester, described in the above schemes).

Scheme VI

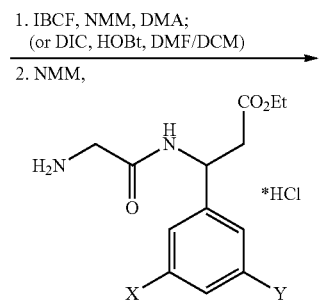

-continued

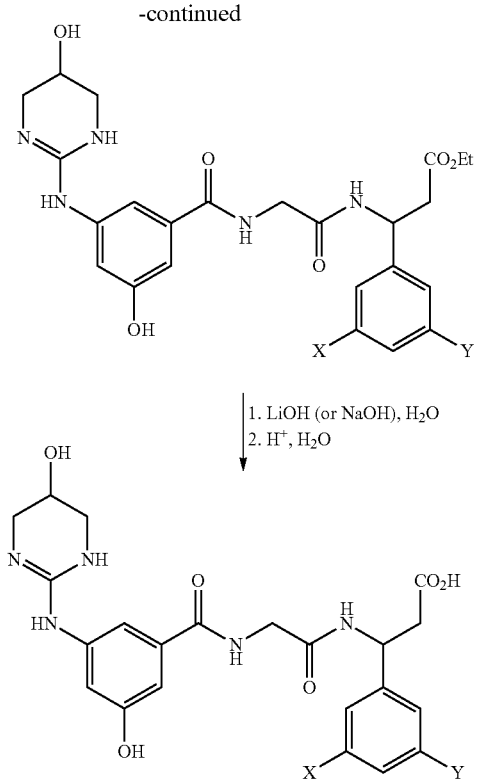

Scheme VI illustrates a general methodology that may be used for preparing various compounds of the present disclosure. Briefly, 3-Hydroxy-5-[(1,4,5,6-tetrahydro-5-hydroxy-2-pyrimidinyl)amino]benzoic acid (described in Scheme II) is activated for coupling using known methods. Thus, after dissolving in a suitable solvent such as DMA an equivalent of NMM is added. The reaction mixture is cooled to ice-bath temperatures and IBCF added. To the mixed anhydride intermediate is added the Gly-β-amino acid ester (described in Scheme IV) and NMM. Upon completion of the reaction the product is purified by preparative HPLC and the ester hydrolyzed to the acid by treating with a base, such as LiOH in a suitable solvent (dioxane/water or acetonitrile/water). Alternatively, a suitable acid, such as TFA can be used. The product is isolated by preparative HPLC or by isolating the zwitterion at pH 5-7 and converting to the desired salt by standard procedures. (The (S) enantiomer is afforded by utilizing the (S)-beta amino acid ester, described in the above schemes).

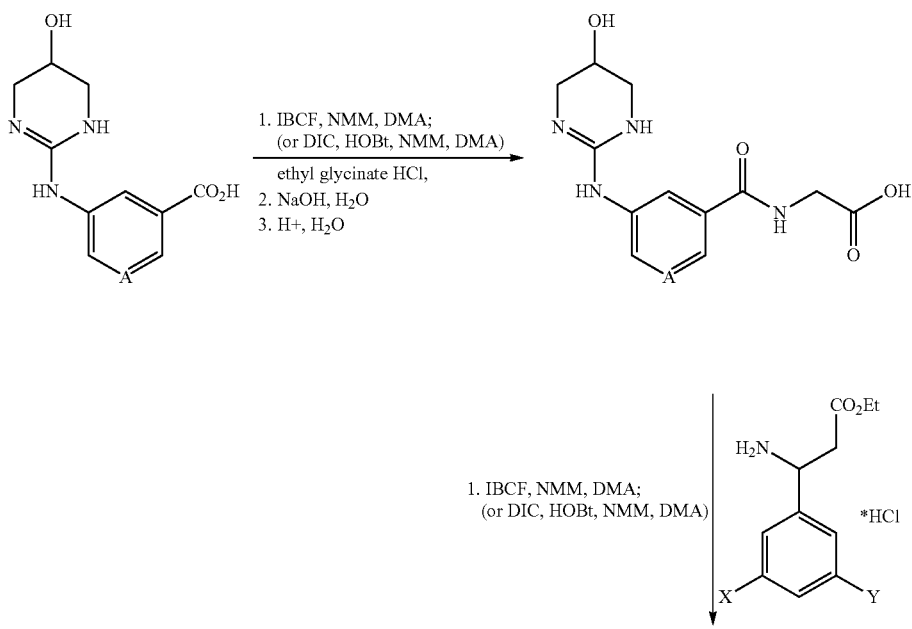

Scheme VII

-continued

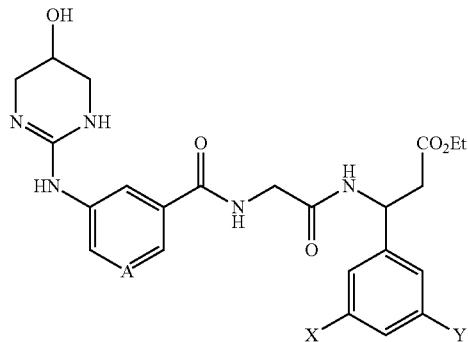

1. LiOH (or NaOH), H₂O
2. H⁺, H₂O

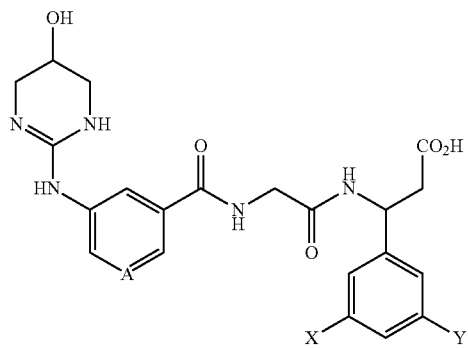

Scheme VII illustrates a general methodology that may be used for preparing various compounds of the present disclosure. Briefly, the cyclic guanidine substituted left hand side aromatic acid portion of Formula I (described for example in Schemes I and II) is activated for coupling using known methods. Thus, after dissolving in a suitable solvent such as DMA an equivalent of NMM is added. The reaction mixture is cooled to ice-bath temperatures and IBCF added. To the mixed anhydride intermediate is added ethyl glycinate HCl and NMM. Upon completion of the reaction the product is purified by preparative HPLC and the ester hydrolyzed to the acid by treating with a base, such as NaOH in a suitable solvent (water, dioxane/water or acetonitrile/water), followed by acidification. This Gly adduct is then activated for coupling using known methods. Thus, after dissolving in a suitable solvent such as DMA an equivalent of NMM is added. The reaction mixture is cooled to ice-bath temperatures and IBCF added. To the mixed anhydride intermediate is added the appropriate beta amino acid ester salt (described in Scheme III above) and NMM. Upon completion of the reaction the product is purified by preparative HPLC and the ester hydrolyzed to the acid by treating with a base, such as LiOH in a suitable solvent (dioxane/water or acetonitrile/water). Alternatively, a suitable acid, such as TFA can be used. The product is isolated by preparative HPLC or by isolating the zwitterion at pH 5-7 and converting to the desired salt by standard procedures (the (S) enantiomer is afforded by utilizing the (S)-beta amino acid ester, described in the above schemes).

Scheme VIII

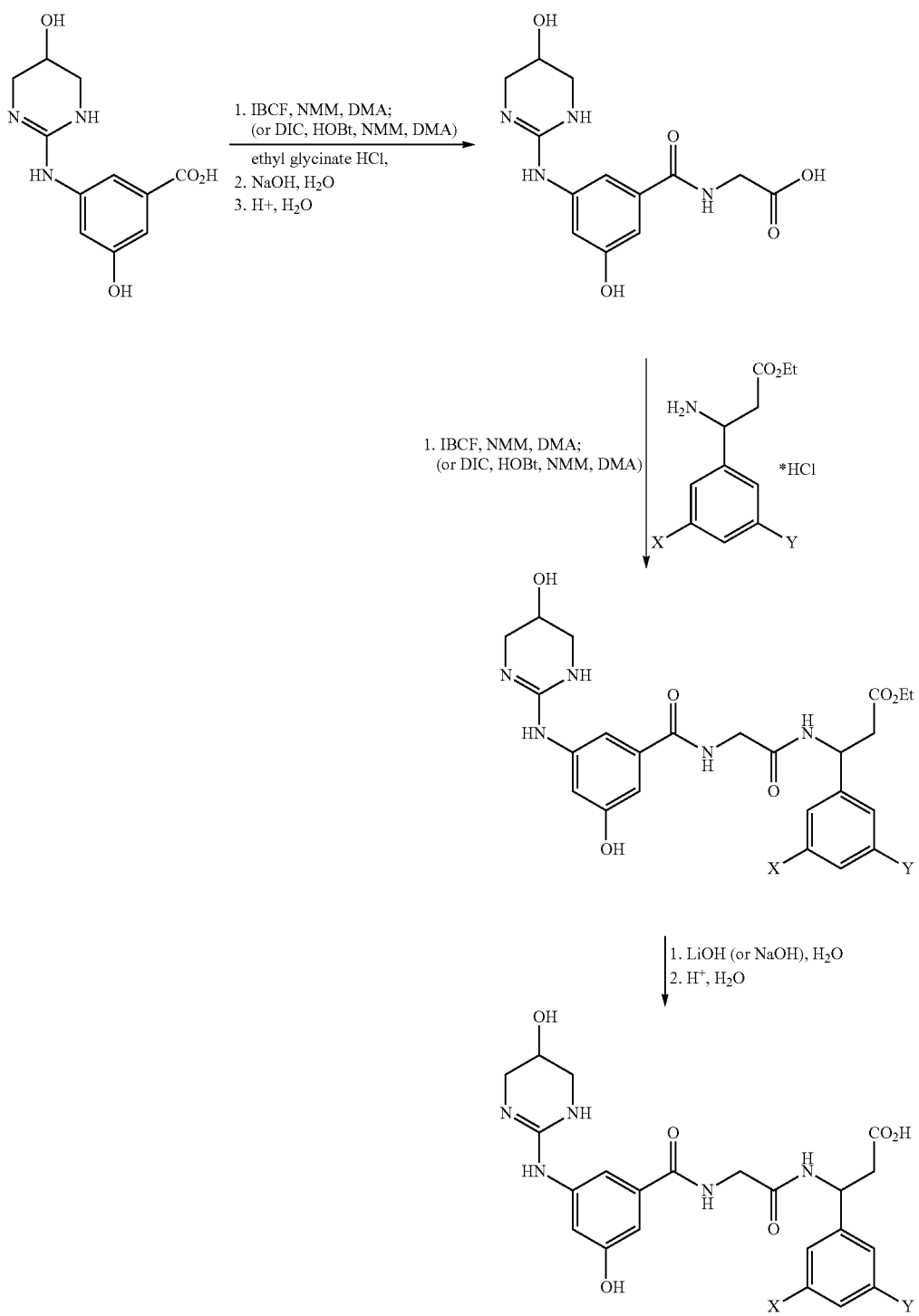

Scheme VIII illustrates a general methodology which may be useful for preparing various compounds of described herein. Briefly, 3-Hydroxy-5-[(1,4,5,6-tetrahydro-5-hydroxy-2-pyrimidinyl)amino]benzoic acid (described in Scheme II) is activated for coupling using known methods. Thus, after dissolving in a suitable solvent such as DMA, an equivalent of NMM is added. The reaction mixture is cooled to ice-bath temperatures and IBCF added. To the mixed anhydride intermediate is added ethyl glycinate HCl and NMM. Upon completion of the reaction the product is purified by preparative HPLC and the ester hydrolyzed to the acid by treating with a base, such as NaOH in a suitable solvent (water, dioxane/water or acetonitrile/water), followed by acidification. This Gly adduct is then activated for coupling using known methods. Thus, after dissolving in a suitable solvent such as DMA an equivalent of NMM is added. The reaction mixture is cooled to ice-bath temperatures and IBCF added. To the mixed anhydride intermediate is added the appropriate beta amino acid ester salt (described in Scheme III above) and NMM. Upon completion of the reaction the product is purified by prep hplc and the ester hydrolyzed to the acid by treating with a base, such as LiOH in a suitable solvent (dioxane/water or acetonitrile/water). Alternatively, a suitable acid, such as TFA can be used. The product is isolated by preparative HPLC or by isolating the zwitterion at pH 5-7 and converting to the desired salt by standard procedures (the (S) enantiomer is afforded by utilizing the (S)-beta amino acid ester, described in the above schemes).

In some embodiments, the compounds of the present disclosure are those described in Table 1A (below), the Examples, and the claims.

TABLE 1A

Example Compounds of the Present Disclosure

| Example Number | Compound Structure |
|---|---|
| 1 | 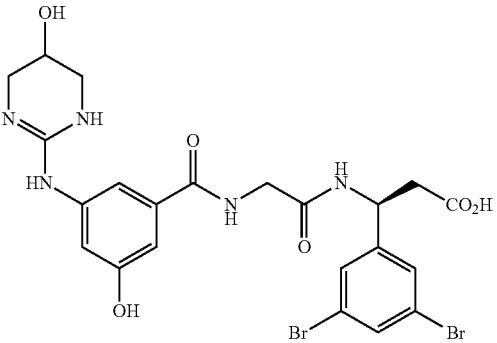 |
| 2 | 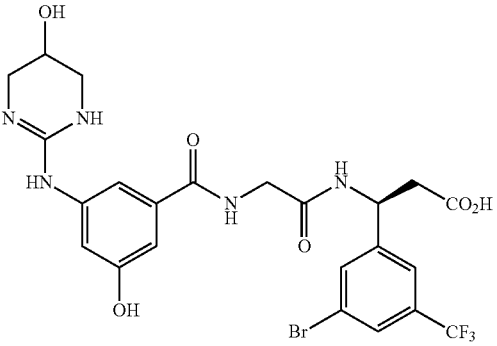 |
| 3 | 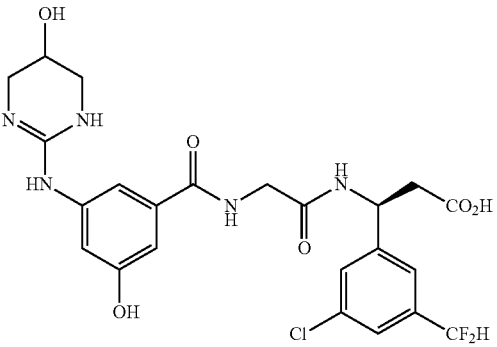 |
| 4 | 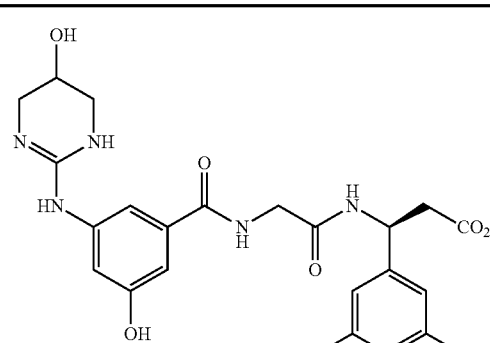 |
| 5 | 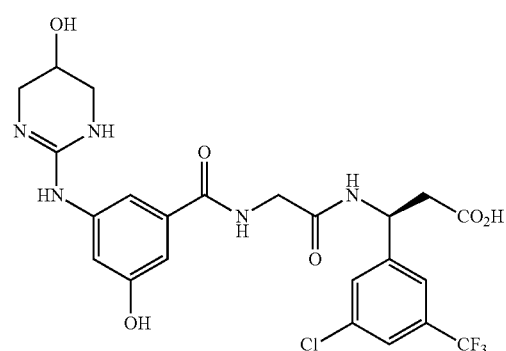 |
| 6 | 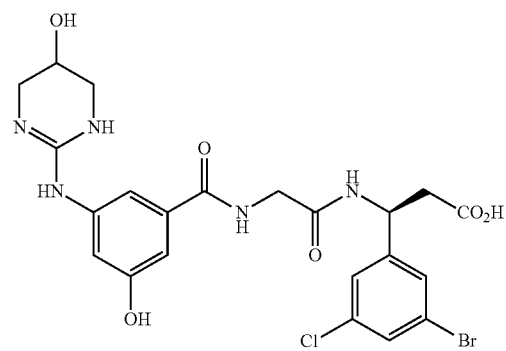 |
| 7 | 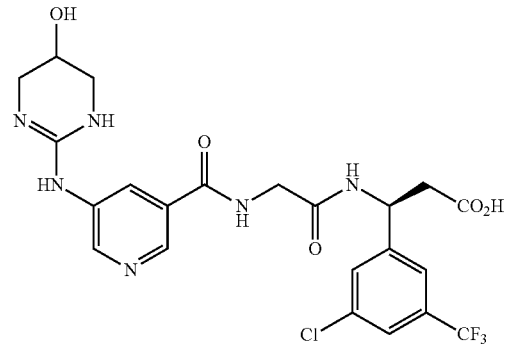 |

TABLE 1A-continued
Example Compounds of the Present Disclosure
| Example Number | Compound Structure |
|---|---|
| 8 | 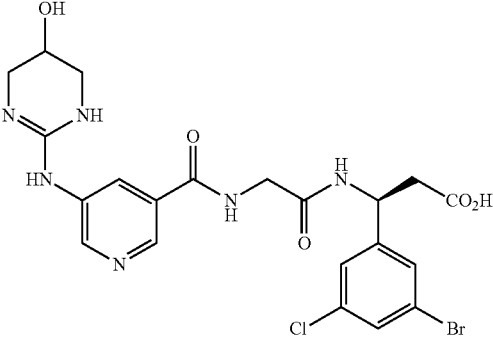 [SMILES: O=C(O)C[C@H](NC(=O)CNC(=O)c1cncc(NC2=NCC(O)CN2)c1)c1cc(Cl)cc(Br)c1] |
| 9 | 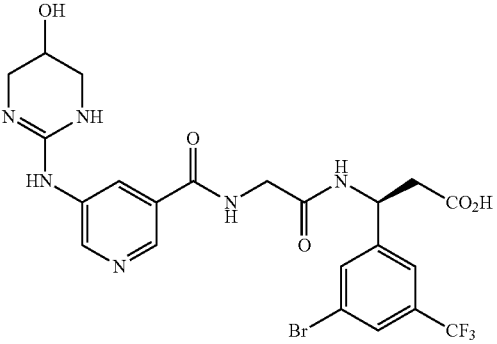 [SMILES: O=C(O)C[C@H](NC(=O)CNC(=O)c1cncc(NC2=NCC(O)CN2)c1)c1cc(Br)cc(C(F)(F)F)c1] |
| 10 | 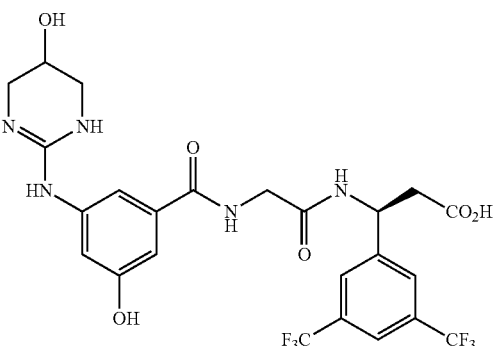 |
| 11 | 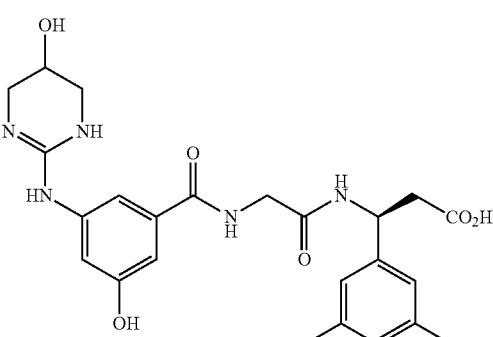 |
| 12 | 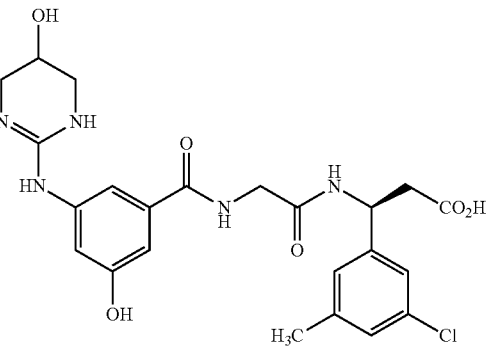 |
| 13 | 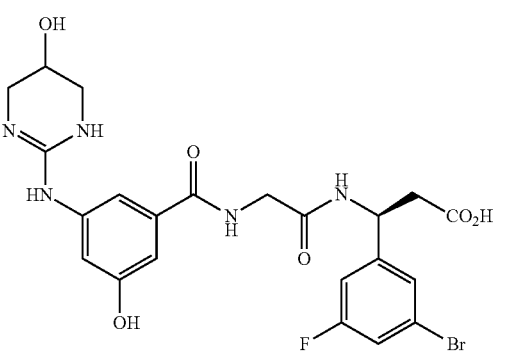 [SMILES: O=C(O)C[C@H](NC(=O)CNC(=O)c1cc(O)cc(NC2=NCC(O)CN2)c1)c1cc(F)cc(Br)c1] |
| 14 | 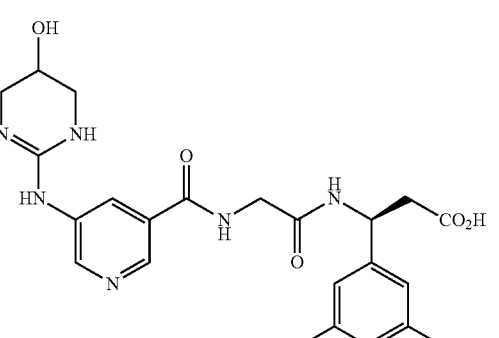 |
| 15 | 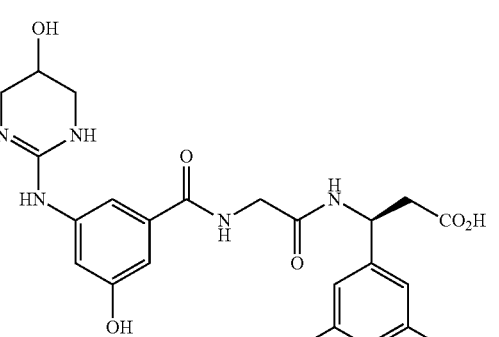 |

TABLE 1A-continued
Example Compounds of the Present Disclosure
| Example Number | Compound Structure |
|---|---|
| 16 | 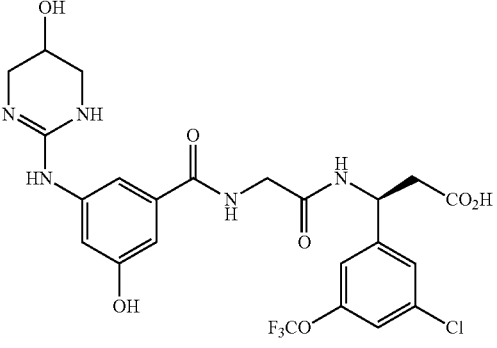 [SMILES: O=C(O)C[C@H](NC(=O)CNC(=O)c1cc(O)cc(NC2=NCC(O)CN2)c1)c1cc(Br)cc(OC(F)(F)F)c1] |
| 17 | 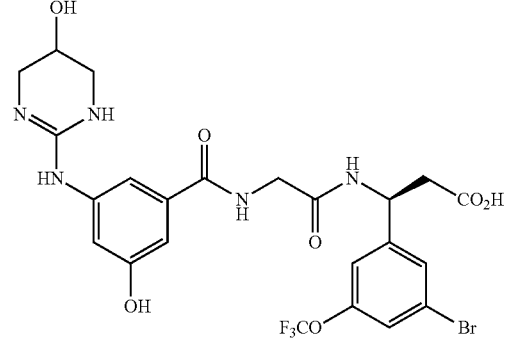 |
TABLE B
Comparison Compounds
| Comparison Number | Compound Structure |
|---|---|
| C1 | 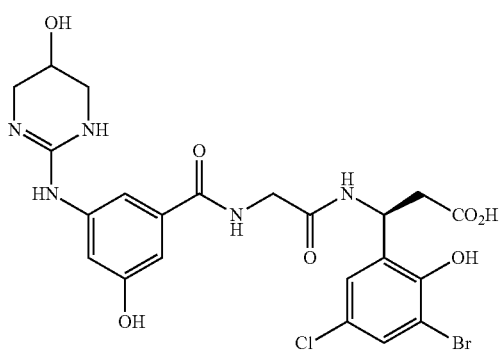 [SMILES: O=C(O)C[C@H](NC(=O)CNC(=O)c1cc(O)cc(NC2=NCC(O)CN2)c1)c1cc(Cl)cc(Br)c1O] |
| C2 | 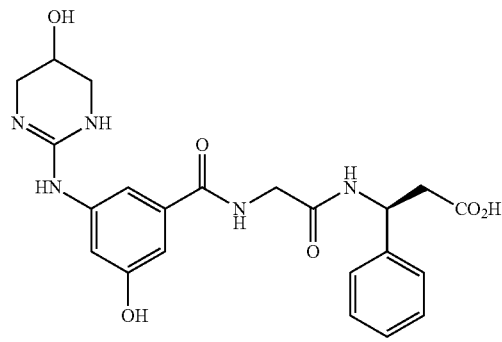 [SMILES: O=C(O)C[C@H](NC(=O)CNC(=O)c1cc(O)cc(NC2=NCC(O)CN2)c1)c1ccccc1] |

TABLE B-continued

Comparison Compounds

| Comparison Number | Compound Structure |
|---|---|
| C3 | (structure) |
| C4 | (structure) |
| C5 | (structure) |
| C6 | (structure) |
| C7 | (structure) |

TABLE B-continued

Comparison Compounds

| Comparison Number | Compound Structure |
| --- | --- |
| C8 | 3-guanidino-benzoyl-Gly-NH-CH(CO₂H)-CH₂-(2-hydroxy-5-methylphenyl) |
| C9 | 3-guanidino-benzoyl-Gly-NH-CH(CO₂H)-CH₂-(3-trifluoromethyl-5-fluorophenyl) |
| C10 | 3-(5-hydroxy-tetrahydropyrimidin-2-ylamino)-5-hydroxybenzoyl-Gly-NH-CH(CO₂H)-CH₂-(4-chloro-2-hydroxy-3-methylphenyl), (S) |
| C11 | 3-(4,5-dihydro-1H-imidazol-2-ylamino)benzoyl-Gly-NH-CH(CO₂H)-CH₂-(4-chloro-2-hydroxy-3-methylphenyl), (S) |
| C12 | 3-(5-hydroxy-tetrahydropyrimidin-2-ylamino)-5-hydroxybenzoyl-Gly-NH-CH(CO₂H)-CH₂-(3-bromo-5-tert-butylphenyl), (S) |

TABLE B-continued
Comparison Compounds
| Comparison Number | Compound Structure |
|---|---|
| C13 | 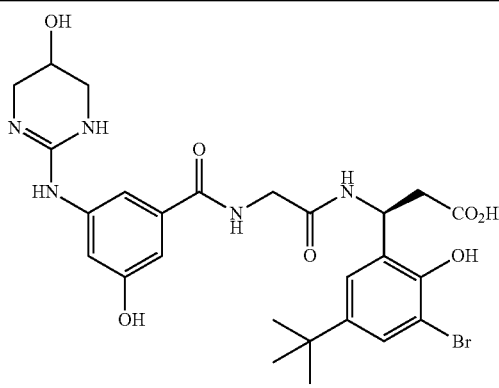 |
| C14 | 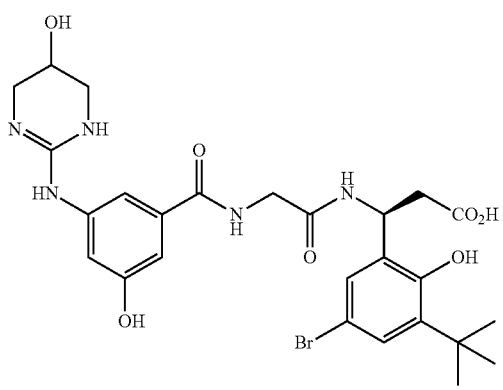 [SMILES: CC(C)(C)c1cc(Br)cc([C@H](CC(=O)O)NC(=O)CNC(=O)c2cc(O)cc(NC3=NCC(O)CN3)c2)c1O] |
| C15 | 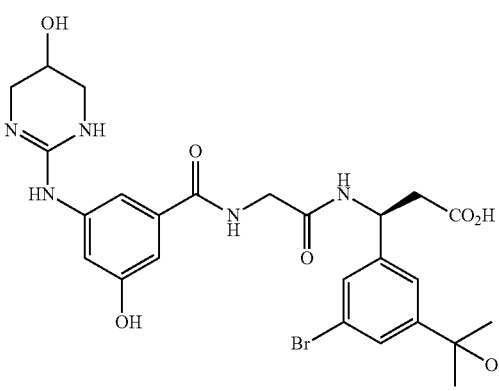 |
| C16 | 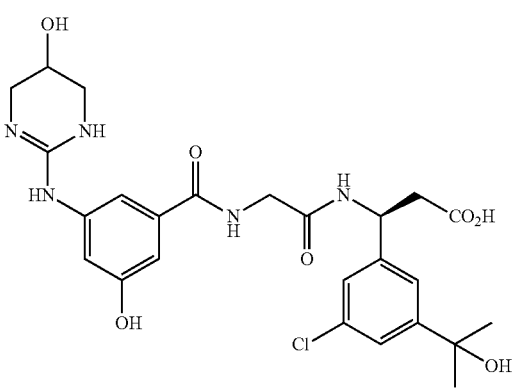 [SMILES: CC(C)(O)c1cc(Cl)cc([C@H](CC(=O)O)NC(=O)CNC(=O)c2cc(O)cc(NC3=NCC(O)CN3)c2)c1] |

TABLE B-continued

| Comparison Compounds | |
|---|---|
| Comparison Number | Compound Structure |

C17

C18

C19

C20

TABLE B-continued
Comparison Compounds
| Comparison Number | Compound Structure |
|---|---|
| C21 | 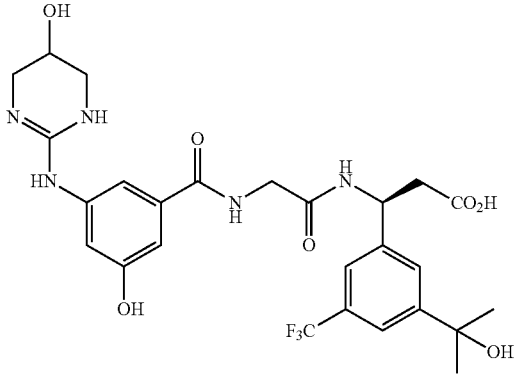 [SMILES: CC(C)(O)c1cc([C@H](CC(=O)O)NC(=O)CNC(=O)c2cc(O)cc(NC3=NCC(O)CN3)c2)cc(C(F)(F)F)c1] |
| C22 | 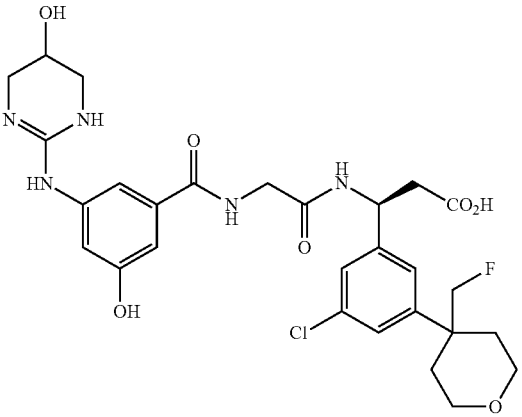 [SMILES: O=C(O)C[C@H](NC(=O)CNC(=O)c1cc(O)cc(NC2=NCC(O)CN2)c1)c1cc(Cl)cc(C2(CF)CCOCC2)c1] |
| C23 | 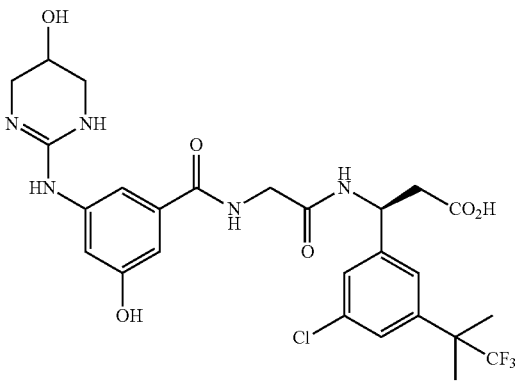 [SMILES: CC(C)(c1cc(Cl)cc([C@H](CC(=O)O)NC(=O)CNC(=O)c2cc(O)cc(NC3=NCC(O)CN3)c2)c1)C(F)(F)F] |
| C24 | 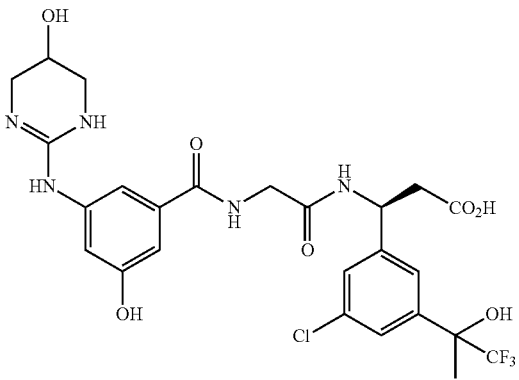 [SMILES: CC(O)(c1cc(Cl)cc([C@H](CC(=O)O)NC(=O)CNC(=O)c2cc(O)cc(NC3=NCC(O)CN3)c2)c1)C(F)(F)F] |

TABLE B-continued
Comparison Compounds
| Comparison Number | Compound Structure |
|---|---|
| C25 | 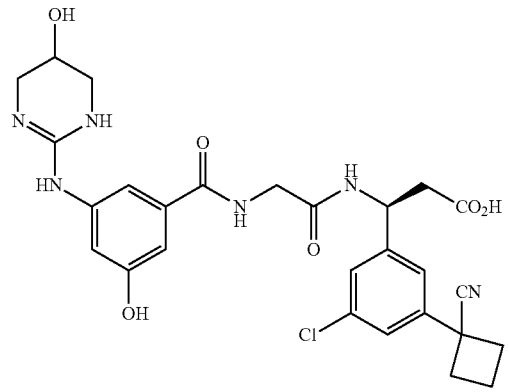 [SMILES: N#CC1(c2cc(Cl)cc([C@H](CC(=O)O)NC(=O)CNC(=O)c3cc(O)cc(NC4=NCC(O)CN4)c3)c2)CCC1] |
| C26 | 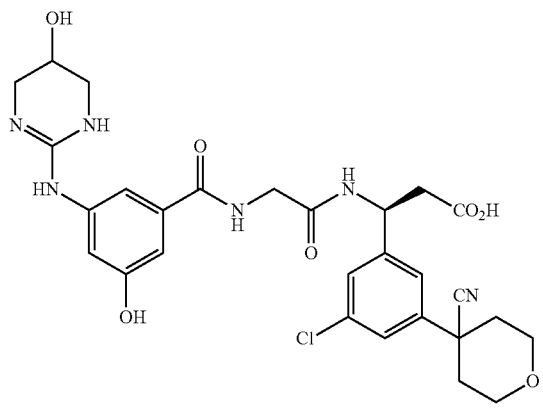 [SMILES: N#CC1(c2cc(Cl)cc([C@H](CC(=O)O)NC(=O)CNC(=O)c3cc(O)cc(NC4=NCC(O)CN4)c3)c2)CCOCC1] |
| C27 | 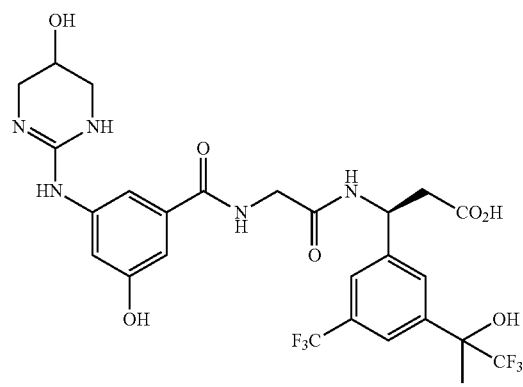 [SMILES: CC(O)(c1cc([C@H](CC(=O)O)NC(=O)CNC(=O)c2cc(O)cc(NC3=NCC(O)CN3)c2)cc(C(F)(F)F)c1)C(F)(F)F] |

TABLE B-continued

Comparison Compounds

| Comparison Number | Compound Structure |
|---|---|
| C28 | *(structure)* |
| C29 | *(structure)* |
| C30 | *(structure)* |

All these methods described above can be further modified and optimized using the principles and techniques taught in U.S. Pat. Nos. 6,013,651 and 6,028,223, which are incorporated herein by reference, as well as the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds employed in methods of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. In some embodiments, the β-amino acid portion of formula I is in the (S) configuration. In some embodiments, the (S) enantiomer is the preferred enantiomer of the β-amino acid group. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration, as defined by the IUPAC 1974 Recommendations. For example, mixtures of stereoisomers may be separated using the techniques taught in the Examples section below, as well as modifications thereof. Tautomeric forms are also included as well as pharmaceutically acceptable salts of such isomers and tautomers.

Atoms making up the compounds of the present disclosure are intended to include all isotopic forms of such atoms. Compounds of the present disclosure include those with one or more atoms that have been isotopically modified or enriched, in particular those with pharmaceutically acceptable isotopes or those useful for pharmaceutically research. Isotopes, as used herein, include those atoms having the same atomic number but different mass numbers. By way of general example and without limitation, isotopes of hydrogen include deuterium and tritium, and isotopes of carbon include $^{13}$C and $^{14}$C. Similarly, it is contemplated that one or more carbon atom(s) of a compound of the present disclosure may be replaced by a silicon atom(s). Furthermore, it is contemplated that one or more oxygen atom(s) of a compound of the present disclosure may be replaced by a sulfur or selenium atom(s).

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present disclosure include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$, Boc), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$, Boc), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

II. Biological Activity

In some embodiments, the compounds of the present disclosure may be used to antagonize multiple RGD-binding integrins. In some of these embodiments, the compounds may be used to treat or prevent diseases in which more than one integrin promotes aberrant angiogenesis. For example, the compounds may be especially useful when a second disease process, which is either co-dependent or independent of angiogenesis, is mediated by RGD integrins that can be simultaneously affected with the anti-angiogenic antagonist. Tumors are known to be dependent on the formation of new blood vessels to sustain growth beyond a few millimeters in diameter. Aberrant angiogenesis in the retina is a characteristic of many blinding disorders such as wet age-related macular degeneration, vitreoretinopathies, retinopathy of prematurity, and diabetic retinopathy. Angiogenesis has been associated with progression of pulmonary and liver fibrosis, and with growth of the synovial pannus in rheumatoid arthritis.

The integrins αvβ3 and αvβ5 have been implicated in promoting angiogenesis (Avraamides et al., 2008), so that their antagonism in addition to other integrins may be predicted to provide superior blockade of this process. Integrin αvβ3 is also known to play a role in tumor cell metastasis, and in the elevated bone resorption associated with osteoporosis and some cancers. The antagonists of the disclosure possess varying activity against at least five integrins that have been reported to bind the latent cytokine TGFβ complex in vitro: αvβ1, αvβ3, αvβ5, αvβ6, and αvβ8. See (Asano et al., 2005; Mu et al., 2002; Munger et al., 1999; Wipff et al., 2007; and Munger et al., 1998), which are incorporated herein by reference. TGFβ is frequently co-expressed with the angiogenic cytokine VEGF and induces its synthesis (Ferrari et al., 2006). Aside from having vascular regulatory activity, TGFβ is a powerful inducer of fibrosis in many tissues such as lung, liver, kidney, and skin (Nishimura, 2009). Virtually all TGFβ is secreted from cells in a complex which contains the latency associated peptide (LAP). The integrins αvβ3, αvβ5, and αvβ6, interact with the RGD motif contained within LAP, producing a conformational change in the complex which allows TGFβ to bind cellular receptors that activate pro-fibrotic pathways. Integrin αvβ8 also activates TGFβ in an RGD-dependent manner, but utilizes a protease-dependent mechanism distinct from the other integrins.

Latent TGFβ is ubiquitously present in tissues, and is activated by integrins in a spatially and temporally restricted manner. Therefore, upregulation of the epithelial integrin αvβ6 in the lungs or liver may promote localized collagen deposition and scarring, as has been observed in patients with idiopathic pulmonary fibrosis (Horan et al., 2008) or hepatic fibrosis (Popov et al., 2008). Similarly, αvβ5, and to a lesser extent αvβ3, are present on mesenchymal cells and are able to activate mesenchymal TGFβ (Wipff et al., 2007; Scotton et al., 2009). Integrin αvβ8 is expressed on subsets of epithelial, neural, immune, and mesenchymal cell types. In the skin, the TGFβ activation that accompanies the wound healing process mediates matrix deposition and promotes the formation of scars. Compounds of the present disclosure, by virtue of their ability to simultaneously inhibit several TGFβ-activating integrins, have the potential for greater efficacy in treatment of fibrosis than previously described compounds having more restricted inhibitory profiles. Furthermore, the compounds provided herein, including, for example, those which have good α5β1 potency, may be used to treat and/or prevent diseases characterized by both aberrant angiogenic and fibrotic pathologies.

TGFβ is an important inducer of the formation of FoxP3$^+$ regulatory T cells ($T_{reg}$) (Yoshimura, 2011). In some embodiments, compounds of the present disclosure, including those that inhibit the activation of TGFβ and/or reduce $T_{reg}$ activity may be used to relieve immune suppression in disease states such as cancer, when administered alone or in combination with existing therapies. Mitigation of $T_{reg}$ activity with such compounds also has the potential to enhance the activity of vaccines which are intended to prevent or treat cancer and infectious diseases. TGFβ, in the presence of IL-6, promotes the conversion of naïve T cells to TH17 cells (Yoshimura, 2011). These cells promote a variety of autoimmune diseases. It has been reported that mice lacking all αvβ8 expression on dendritic cells have near complete protection from experimental autoimmune encephalitis, a model of multiple sclerosis (Melton et al., 2010). Therefore, compounds of the present disclosure, including those that inhibit the activation of TGFβ and/or reduce Th17 activity, and be used in preventing or treating autoimmune disease when administered alone or in combination with existing therapies.

Antagonism of the integrin αIIbβ3 (also known as the fibrinogen receptor), is known to block platelet aggregation as part of the blood coagulation process. Hence, to avoid increased bleeding when treating conditions or disease states mediated by integrin α5β1 and other integrins, it would be beneficial to utilize compounds which selectively spare αIIbβ3.

As discussed above, integrins are a family of integral cytoplasmic membrane proteins that mediate cell interactions with other cells and with the extracellular matrix (ECM). These proteins also play a role in cell signaling and thereby regulate cellular shape, motility, and the cell cycle. Not only do integrins perform "outside-in" signaling typical of receptors, but they also operate an "inside-out" mode. Thus, they transduce information from the ECM to the cell as well as reveal the status of the cell to the outside, allowing rapid and flexible responses to changes in the environment, for example to allow blood coagulation by platelets.

There are many types of integrin, and many cells have multiple types on their surface. Integrins are of vital importance to all animals and have been found in all animals investigated, from sponges to mammals. As such compounds which target integrins have found numerous uses in different animals including companion animals, livestock animals, zoo animals as well as wild animals. Integrins have been extensively studied in humans. Integrins work alongside other proteins such as cadherins, immunoglobulin superfamily cell adhesion molecules, selectins and syndecans to mediate cell-cell and cell-matrix interaction and communication. Integrins bind cell surface and ECM components such as fibronectin, vitronectin, collagen, and laminin.

Each integrin is formed by the non-covalent heterodimerization of alpha and beta glycoprotein subunits, the combination of which conveys distinct biological activities such as cell attachment, migration, proliferation, differentiation, and survival. Currently, 24 integrins have been described in mammals that are formed by pairing of 18 α subunits and 8 β subunits, as set out in Table 2.

TABLE 2

| \multicolumn{4}{c}{Integrins} | | | |
|---|---|---|---|
| Gene | Protein | Synonym | Type |
| ITGA1 | CD49a | VLA1 | Alpha |
| ITGA2 | CD49b | VLA2 | Alpha |
| ITGA3 | CD49c | VLA3 | Alpha |
| ITGA4 | CD49d | VLA4 | Alpha |
| ITGA5 | CD49e | VLA5 | Alpha |
| ITGA6 | CD49f | VLA6 | Alpha |
| ITGA7 | ITGA7 | FLJ25220 | Alpha |
| ITGA8 | ITGA8 |  | Alpha |
| ITGA9 | ITGA9 | RLC | Alpha |
| ITGA10 | ITGA10 |  | Alpha |
| ITGA11 | ITGA11 | HsT18964 | Alpha |
| ITGAD | CD11D | FLJ39841 | Alpha |
| ITGAE | CD103 | HUMINAE | Alpha |
| ITGAL | CD11a | LFA1A | Alpha |
| ITGAM | CD11b | MAC-1 | Alpha |
| ITGAV | CD51 | VNRA, MSK8 | Alpha |
| ITGAW | ITGAW |  | Alpha |
| ITGAX | CD11c |  | Alpha |
| ITGB1 | CD29 | FNRB, MSK12, MDF2 | Beta |
| ITGB2 | CD18 | LFA-1, MAC-1, MFI7 | Beta |
| ITGB3 | CD61 | GP3A, GPIIIa | Beta |
| ITGB4 | CD104 |  | Beta |
| ITGB5 | ITGB5 | FLJ26658 | Beta |
| ITGB6 | ITGB6 |  | Beta |
| ITGB7 | ITGB7 |  | Beta |
| ITGB8 | ITGB8 |  | Beta |

In addition, variants of some of the subunits are formed by differential splicing; for example, four variants of the beta-1 subunit exist. Through different combinations of these α and β subunits, some 24 unique integrins are generated, although the number varies according to different studies.

III. Therapeutic Methods

The present disclosure relates to the fields of pharmaceuticals, medicine and cell biology. More specifically, it relates to pharmaceutical agents (compounds) and pharmaceutical compositions thereof which may be used as integrin receptor antagonists, including in some embodiments, multi-integrin receptor antagonists. As such, these compounds may be used in pharmaceutical compositions and in methods for treating conditions mediated by one or more of such integrins, for example, by inhibiting or antagonizing one or more of these integrins. In several aspects of the present disclosure, the compounds provided herein may be used in a variety of biological, prophylactic or therapeutic areas, including those one or more the α5b1, α8β1, αvβ1, αvβ3, αvβ5, avb6, and avb8 integrins plays a role.

In another aspect, this disclosure provides methods of inhibiting or antagonizing one or more of the α5β1, α8β1, αvβ1, αvβ3, αvβ5, αvβ6 and αvβ8 integrins using one or more of the compounds disclosed herein, as well as pharmaceutical compositions thereof. In some embodiments, these methods inhibit pathological conditions associated therewith, such as angiogenesis, including tumor angiogenesis, fibrosis and fibrotic diseases, such as pulmonary, renal, cardiac, muscle, and liver fibrosis, scarring, such as retinal, corneal and dermal scarring, retinopathy, including diabetic retinopathy and macular degeneration, vitreoretinopathy, including retinopathy of prematurity (ROP) and familial exudative vitreoretinopathy (FEVR), osteoporosis, humoral hypercalcemia of malignancy, Paget's disease, tumor metastasis, solid tumor growth (neoplasia), arthritis, including rheumatoid arthritis, periodontal disease, psoriasis, smooth muscle cell migration and restenosis, autoimmune disease, such as multiple sclerosis, and infectious pathogens by administering a therapeutically effective amount of a compound provided herein. In some embodiments, the compound is administered as part of a pharmaceutical composition further comprising a pharmaceutically acceptable carrier. In some embodiments, the compounds and/or pharmaceutical compositions thereof may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitoneally. In some embodiments, the compounds of the present disclosure are administered by any suitable route in the form of a pharmaceutical composition adapted to such a route, and in a dose effective for the treatment intended. Therapeutically effective doses of the compounds required to prevent or arrest the progress of or to treat a medical condition are readily ascertained by one of ordinary skill in the art using preclinical and clinical approaches familiar to the medicinal arts.

Based upon standard laboratory experimental techniques and procedures well known and appreciated by those skilled in the art, as well as comparisons with compounds of known usefulness, the compounds described above can be used in the treatment of patients suffering from the above pathological conditions. One skilled in the art will recognize that selection of the most appropriate compound of the disclosure is within the ability of one with ordinary skill in the art and will depend on a variety of factors including assessment of results obtained in standard assay and animal models.

In another aspect, the compounds provided herein may be used in a variety of biological, prophylactic or therapeutic areas, including those in wherein one or more the α5b1, α8β1, αvβ1, αvβ3, αvβ5, avb6, and avb8 integrins play a role. The disclosure further involves treating or inhibiting pathological conditions associated therewith such as angiogenesis, including tumor angiogenesis, fibrosis and fibrotic diseases such as pulmonary fibrosis, renal, cardiac, muscle, and liver fibrosis, scleroderma, scarring, such as retinal, corneal and dermal scarring, retinopathy, including diabetic retinopathy and macular degeneration, vitreoretinopathy, including retinopathy of prematurity (ROP) and familial exudative vitreoretinopathy (FEVR), osteoporosis, humoral hypercalcemia of malignancy, Paget's disease, tumor metastasis, solid tumor growth (neoplasia), arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials. Further, such pharmaceutical agents are useful as immune system modulators via inhibition of TGF-β activation resulting from inhibiting or antagonizing the targeted integrins. Such immune modulation affects the immune activity and functions of T regulatory and T effector cells, and as such can be useful in the treatment of immune related pathologies, including autoimmune diseases such as multiple sclerosis, as well as in the treatment of tumors and infectious pathogens.

IV. Pharmaceutical Formulations and Routes of Administration

It is another object of the disclosure to provide pharmaceutical compositions comprising one or more of the compounds described herein. Such compositions are useful in inhibiting or antagonizing integrins, including, for examples, α5β1, α8β1, αvβ1, αvβ3, αvβ6, and αvβ8 integrins. In some embodiments, this disclosure provides pharmaceutical compositions comprising a compound that is effective in inhibiting or antagonizing one or more of the α5β1, α8β1, αvβ1, αvβ3, αvβ5, αvβ6 and αvβ8 integrins using one or more of the compounds disclosed herein, as well as pharmaceutical compositions thereof. In some of these embodiments, such pharmaceutical compositions further comprise one or more non-toxic, pharmaceutically acceptable carriers and/or diluents and/or adjuvants.

For the purpose of administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound of the present invention formulated with one or more excipients and/or drug carriers appropriate to the indicated route of administration. In some embodiments, the compounds of the present invention are formulated in a manner amenable for the treatment of human and/or veterinary patients. In some embodiments, formulation comprises admixing or combining one or more of the compounds of the present invention with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. Pharmaceutical formulations may be subjected to conventional pharmaceutical operations, such as sterilization and/or may contain drug carriers and/or excipients such as preservatives, stabilizers, wetting agents, emulsifiers, encapsulating agents such as lipids, dendrimers, polymers, proteins such as albumin, or nucleic acids, and buffers, etc.

The pharmaceutical compositions useful in the present disclosure may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions may be suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it may be useful to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the methods of preparation include vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

In some embodiments, it is advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the disclosure are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

In some embodiments, the therapeutic compound may also be administered topically to the skin, eye, or mucosa. Alternatively, if local delivery to the lungs is desired, the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general a human equivalent dose (HED) in mg/kg can be calculated in accordance with the following formula (see, e.g., Reagan-Shaw et al., 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 1% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may taken orally and that the timing of which is or is not dependent upon food intake. Thus, for example, the agent can be taken every morning and/or every evening, regardless of when the subject has eaten or will eat.

V. Combination Therapy

In addition to being used as a monotherapy, the compounds of the present disclosure may also find use in combination therapies. Effective combination therapy may be achieved with a single composition or pharmacological formulation that includes both agents, or with two distinct compositions or formulations, administered at the same time, wherein one composition includes a compound of this disclosure, and the other includes the second agent(s). Alternatively, the therapy may precede or follow the other agent treatment by intervals ranging from minutes to months.

Non-limiting examples of such combination therapy include combination of one or more compounds of the disclosure with another agent, for example, an anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the disclosure may be combined with agents designed to improve a patient's immune response to cancer, including (but not limited to) cancer vaccines.

VI. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; and "amino" means —NH$_2$.

In the context of chemical formulas, the symbol "—" means a single bond, "=" means a double bond, and "≡" means triple bond. The symbol "- - -" represents an optional bond, which if present is either single or double. The symbol ==== represents a single bond or a double bond. Thus, for example, the formula

includes

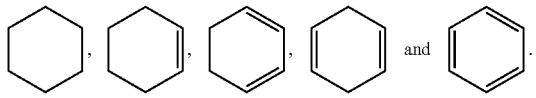

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿", when drawn perpendicularly across a bond

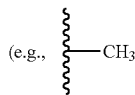

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀⦀⦀" means a single bond where the group attached to the thick end of the wedge is "into the page". The symbol "∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$(Me), —CH$_2$CH$_3$(Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The term "fluoroalkoxy" when used without the "substituted" modifier, refers to groups, defined as —OR, in which R is fluoroalkyl. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomotology of the disease, and/or (2) slowing the onset of the pathology or symptomotology of a disease in a subject or patient which may be at risk and/or predisposed to the disease but does not yet experience or display any or all of the pathology or symptomotology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

"Treatment" or "treating" includes (1) inhibiting a disease in a subject or patient experiencing or displaying the pathology or symptomotology of the disease (e.g., arresting further development of the pathology and/or symptomotology), (2) ameliorating a disease in a subject or patient that is experiencing or displaying the pathology or symptomotology of the disease (e.g., reversing the pathology and/or symptomotology), and/or (3) effecting any measurable decrease in a disease in a subject or patient that is experiencing or displaying the pathology or symptomotology of the disease.

Other abbreviations used herein are as follows: $^1$H NMR is proton nuclear magnetic resonance, AcOH is acetic acid, Ar is argon, ACN or CH$_3$CN is acetonitrile, CHN analysis is carbon/hydrogen/nitrogen elemental analysis, CHNCl analysis is carbon/hydrogen/nitrogen/chlorine elemental analysis, CHNS analysis is carbon/hydrogen/nitrogen/sulfur elemental analysis, DI water is deionized water, DIC is diisopropyl carbodiimide, DMA is N,N-dimethylacetamide, DMAP is 4-(N,N-dimethylamino)pyridine, DMF is N,N-dimethylformamide, EDCl is 1-(3-dimethylaminopropyl)-3-ethylcarbodiimide hydrochloride, EtOAc is ethyl acetate, EtOH is ethanol, FAB MS is fast atom bombardment mass spectroscopy, g is gram(s), HOBT is 1-hydroxybenzotriazole hydrate, HPLC is high performance liquid chromatography, IBCF is isobutylchloroformate, KSCN is potassium thiocyanate, L is liter, LiOH is lithium hydroxide, MEM is methoxyethoxymethyl, MEMCl is methoxyethoxymethyl chloride, MeOH is methanol, mg is milligram, MgSO$_4$ is magnesium sulfate, ml is milliliter, mL is milliliter, MS is mass spectroscopy, MTBE is methyl tert-butyl ether, N$_2$ is nitrogen, NaHCO$_3$ is sodium bicarbonate, NaOH is sodium hydroxide, Na$_2$SO$_4$ is sodium sulfate, NMM is N-methyl-morpholine, NMP is N-methyl pyrrolidinone, NMR is nuclear magnetic resonance, P$_2$O$_5$ is phosphorous pentoxide, PTSA is para-toluenesulfonic acid, RPHPLC is reverse phase high performance liquid chromatography, RT is room temperature, TFA is trifluoroacetic acid, THF is tetrahydrofuran, TMS is trimethylsilyl, and Δ signifies heating the reaction mixture.

The above definitions supersede any conflicting definition in any of the reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

VII. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

A. Instrumentation and General Methods.

Analytical HPLC analyses were performed on an Agilent 1100 system and LC-MS analyses were conducted on Agilent 1100 Series LC/MSD system. Reverse-phase preparative HPLC purifications were performed on a Biotage SP4 HPFC system using a variable dual wavelength UV detector on a Biotage KP-C18-HS 120 g SNAP column using acetonitrile/water gradient containing 0.05% TFA. All final compounds were analyzed by analytical HPLC and peaks were monitored at 210, 254 and 280 nM for purity. $^1$H and $^{19}$F NMR spectra were recorded in DMSO-d$_6$ on a Bruker Avance-III/400 MHz spectrometer equipped with a Broad Band NMR probe. The signal of the deuterated solvent was used as an internal reference. The chemical shifts are expressed in ppm (δ) and coupling constants (J) are reported in hertz (Hz). $^{19}$F NMR detects a signal for the TFA salt of final products (~74 ppm) stemming from TFA in the prep HPLC solvents during final purification. Reactions were performed under an atmosphere of dry nitrogen unless otherwise stated.

B. Preparation of Compounds

Example A

Preparation of 3-Hydroxy-5-((5-hydroxy-1,4,5,6-tetrahydropyrimidin-2-yl)aminobenzoic acid

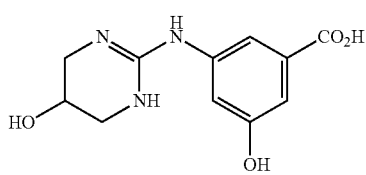 [SMILES: O=C(O)c1cc(O)cc(NC2=NCC(O)CN2)c1]

3-Hydroxy-5-((5-hydroxy-1,4,5,6-tetrahydropyrimidin-2-yl)aminobenzoic acid was synthesized according to literature procedures (see *Organic Process Research & Development*, 8:571-575, 2004, which is incorporated herein by reference).

Example B

Preparation of 2-(3-Hydroxy-5-((5-hydroxy-1,4,5,6-tetrahydropyrimidin-2-yl)amino)benzamido) acetic acid

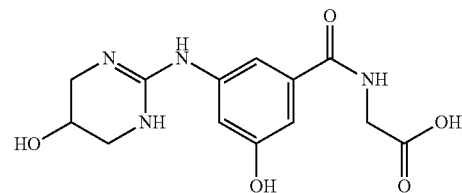 [SMILES: O=C(O)CNC(=O)c1cc(O)cc(NC2=NCC(O)CN2)c1]

2-(3-Hydroxy-5-((5-hydroxy-1,4,5,6-tetrahydropyrimidin-2-yl)amino)benzamido)acetic acid was prepared according to the following procedure:

Coupling of 3-hydroxy-5-((5-hydroxy-1,4,5,6-tetrahydropyrimidin-2-yl)aminobenzoic acid with glycine ethyl ester

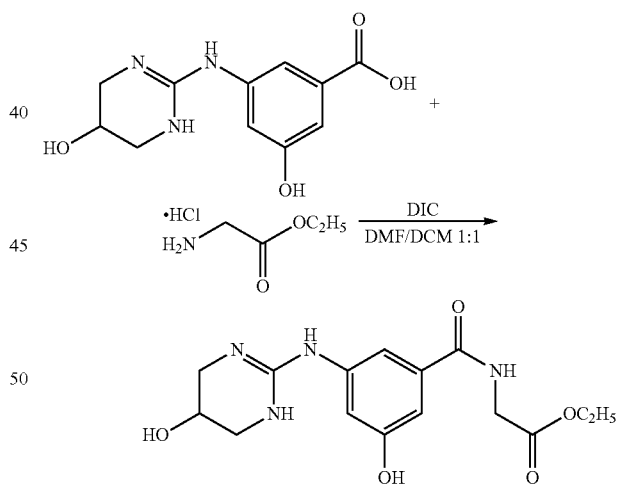

To a suspension of 3-hydroxy-5-((5-hydroxy-1,4,5,6-tetrahydropyrimidin-2-yl)aminobenzoic acid (9.013 g, 35.87 mmol) in a 1:1 mixture of DMF (50.0 mL) and DCM (50.0 mL) was added glycine ethyl ester hydrochloride (5.02 g, 35.95 mmol) and the mixture was stirred at room temperature under nitrogen atmosphere. Neat N,N'-diisopropylcarbodiimide (6.75 mL, 43.60 mmol) was added to above reaction mixture and the mixture was stirred at room temperature overnight to give a colorless suspension. The crude reaction mixture was used as such for the hydrolysis of the above ester.

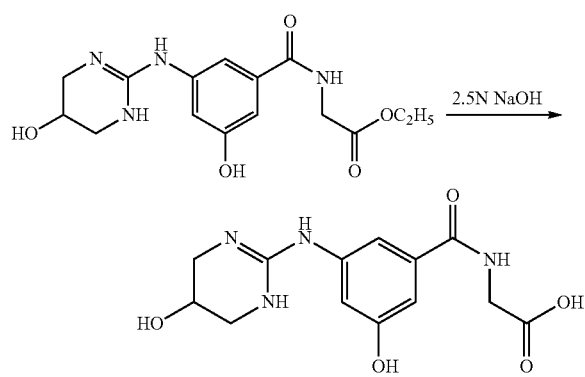

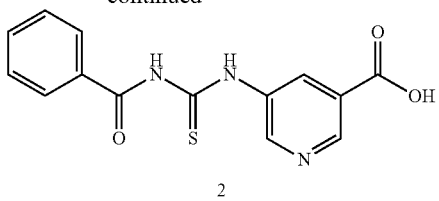

A mixture of compound 1 (40 g, 0.3 mol) and benzoylisothiocyanate (95 g, 0.58 mol) in $CH_3CN$ (2.0 L) was stirred at room temperature for 12 h. TLC showed no starting material left. The precipitate was filtered and washed with $CH_3CN$, dried to afford Compound 2 (80 g, 90%) as a light yellow solid.

Step 2

The above crude reaction mixture was cooled to 10° C. (ice-bath) and a 2.5 N NaOH solution (90.0 mL) was added slowly with stirring, the solution temperature was kept below 20° C., to give a pale yellow solution/suspension. The reaction mixture was stirred at room temperature for 1.5 h. The reaction mixture was acidified with 5N HCl with stirring to pH 5 to give a colorless precipitate and the mixture was stirred at room temperature for another 15 min and filtered to give a colorless solid. The solid was washed with water (1×25 mL) and then with acetonitrile (1×25 mL). The solid was dried in-vacuo to give a colorless powder (9.686 g, yield 88%).

$^1$H NMR (400 MHz, $D_2O$): δ 3.37 (dd, J=12.7 and 3.1 Hz, 2H), 3.50 (dd, J=12.7 and 2.8 Hz, 2H), 4.17 (s, 2H), 4.37 (m, 1H), 6.97 (t, J=2.01 Hz, 1H), 7.17-7.26 (m, 2H). $^1$H NMR spectrum of the sample was consistent with the suggested structure of the product.

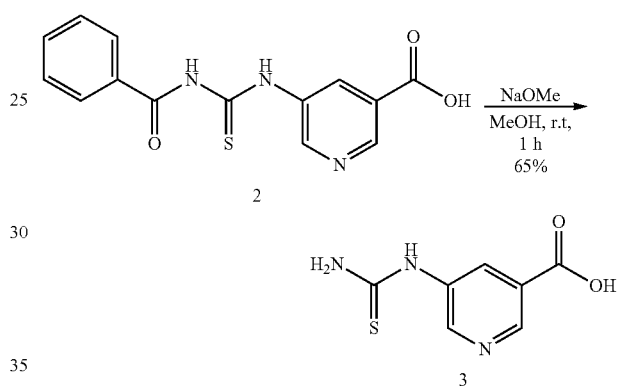

Into a stirred solution of compound 2 (80 g, 0.27 mol) in anhydrous $CH_3OH$ (500 ml) was added NaOMe (28.5 g, 0.53 mol) slowly at room temperature. A clear solution resulted in 20 min, and the reaction mixture was stirred for 1 h. The solvent was removed and the residue was triturated with t-BuOMe to leave a light yellow powder. The powder was diluted with $H_2O$, acidified to pH=2-3. The yellow solid formed was filtered, dried to afford Compound 3 (33.7 g, 65%).

Example C

Preparation of 5-((5-hydroxy-1,4,5,6-tetrahydropyrimidin-2-yl)amino nicotinic acid

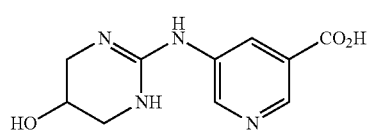 [SMILES: O=C(O)c1cncc(NC2=NCC(O)CN2)c1]

5-((5-hydroxy-1,4,5,6-tetrahydropyrimidin-2-yl)amino nicotinic acid was prepared according to the following procedure:

Step 1

Step 3

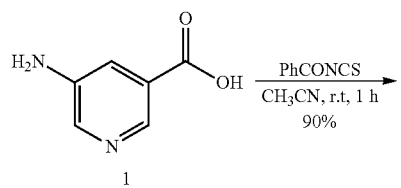

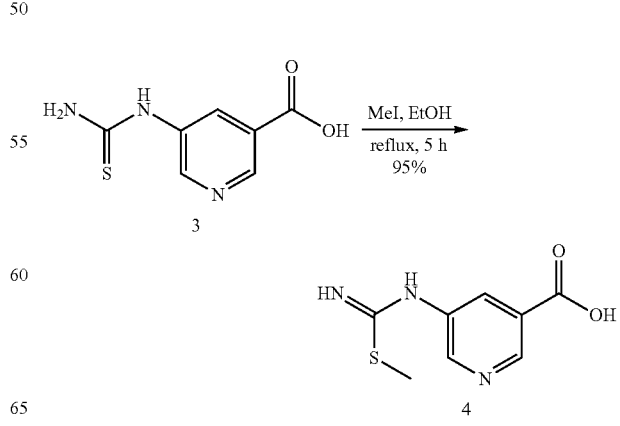

Into a stirred solution of compound 3 (33.7 g, 0.17 mol) in DMF (200 mL) was added CH₃I (24.3 g, 0.17 mol) slowly at room temperature. The reaction mixture was stirred at RT for 1 h. TLC showed no starting material left. The solvent was removed, and Compound 4 (34.3 g, 95%) was obtained as a yellow oil.

Step 4

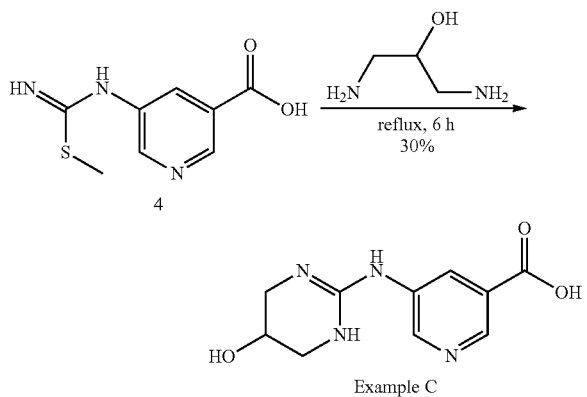

Example C

A mixture of compound 4 (15.5 g, 0.074 mol) and the hydroxy diamino propane (20 g, 0.22 mol) in DMF (100 mL) was heated to reflux and stirred for 5 h. The solid formed was filtered and dried. Example C (5.2 g, 30%) was obtained as a white solid. LC/MS (M+H=237) is consistent for the desired product. ¹H NMR: DMSO-d₆ 400 MHz δ 13.053 (s, 1H), 9.881 (s, 2H), 8.783 (s, 1H), 8.630 (s, 1H), 7.897 (s, 1H), 5.492 (s, 1H), 4.112 (s, 1H), 3.410 (s, 2H), 3.228-3.190 (m, 2H).

Example D

Preparation of 2-[[5-[(5-hydroxy-1,4,5,6-tetrahydro-pyrimidin-2-yl)amino]pyridine-3-carbonyl]amino] acetic acid 2-[[5-[(5-hydroxy-1,4,5,6-tetrahydropyrimidin-2-yl) amino]pyridine-3-carbonyl]amino]acetic acid was prepared according to the following procedure:

Step 1

To a suspension of 5-((5-Hydroxy-1,4,5,6-tetrahydropyrimidin-2-yl)amino)nicotinic acid (1.20 g, 5.08 mmol) in a 1:1 mixture of DMF (10.0 mL) and DCM (10.0 mL) was added glycine ethyl ester hydrochloride (0.798 g, 5.717 mmol) and the mixture was stirred at room temperature under nitrogen atmosphere for 10 min. Neat N,N'-diisopropylcarbodiimide (1.10 mL, 7.104 mmol) was added to above reaction mixture and the mixture was stirred at room temperature overnight to give a colorless to cream suspension. The solvent was evaporated in-vacuo to afford a pale yellow viscous residue. LC-MS analysis of the residue shows the desired product's mass: m/z 322 (M+H), m/z 344 (M+Na) and m/z 643 (2M+H Calculated for C₁₄H₁₉N₅O₄: 321.33. The crude product was used as such in the next step for the saponification of the above ester.

Step 2

Example D

The above crude product was dissolved in a mixture of DMF/DCM (1:1) (10 mL) and the solution was cooled to 10° C. (ice-bath) and a 2.5 N NaOH solution (10.0 mL) was added slowly with stirring, the solution temperature was kept below 20° C., to give a pale yellow solution. The reaction mixture was stirred at room temperature overnight. The reaction mixture was acidified with 5N HCl with stirring to pH 5 to give a yellow-orange solution. The mixture was diluted with DCM (25 mL) and the organic and the aqueous layers were separated. The aqueous layer was evaporated in-vacuo to afford a yellow gummy solid. The crude product was purified by reverse-phase HPLC with a gradient 10-40% CH₃CN in water containing 0.05% TFA to give the desired product as a colorless to yellow gummy solid. The solid was triturated with acetonitrile to give a colorless to pale yellow crystalline solid which was recrystallized from methanol to afford a cream solid (869.3 mg, yield 59%). LC-MS analysis of the solid shows the desired product's mass: m/z 294 (M+H), and m/z 316 (M+Na); Calculated for C₁₂H₁₅N₅O₄: 293.28. ¹H NMR (400 MHz, D₂O): δ 3.19 (dd, J=12.47 and 3.67 Hz, 2H), 3.37 (dd, J=12.47 and 2.93 Hz, 2H), 3.96 (s, 2H), 4.11 (m, 1H), 8.12

(t, J=2.20 Hz, 1H), 8.64 (d, J=2.45 Hz, 1H), 8.90 (d, J=1.96 Hz, 1H). $^1$H NMR spectrum of the compound was consistent with the suggested structure of the product as Example D.

Beta Amino Acids and Their Corresponding Beta Amino Ester Intermediates

Beta amino acids and their corresponding beta amino ester intermediates used as starting materials and reagents in the synthesis of examples 1-17 can be synthesized as depicted in Scheme III above. Briefly, such beta amino acids and esters can be synthesized from the appropriate benzaldehyde and under the conditions depicted. Alternatively, the appropriate benzaldehyde can be reacted with mono-ethyl or methyl malonate to yield the racemic beta amino ethyl ester directly. Examples utilizing such an alternative method are described below. Unless otherwise exemplified, all relevant benzaldehydes are readily available commercially or can be readily synthesized from the appropriate phenyl bromide, n-BuLi and DMF by methods known to those skilled in the art. As noted in Scheme III, the corresponding racemic beta amino esters can be converted to the desired (S) enantiomer either via supercritical fluid chiral chromatographic separation or via selective enzymatic cleavage of the (S) beta amino ester with Amano Lipase PS (Sigma Aldrich) to the readily isolated (S) beta amino acid, which can then be converted to the (S) ester and used as such for the synthesis of the examples 1-17 disclosed herein.

The following are representative methods exemplifying a variety of general procedures used in various steps in the formation of all beta amino ester intermediates utilized in the synthesis of examples 1-17 which follow, and are meant to illustrate the general utility of such methods:

Example E

Preparation of ethyl (3S)-3-amino-3-[3-chloro-5-(trifluoromethyl)phenyl]propanoate hydrochloride

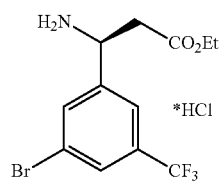 [SMILES: CCOC(=O)C[C@H](N)c1cc(Br)cc(C(F)(F)F)c1]

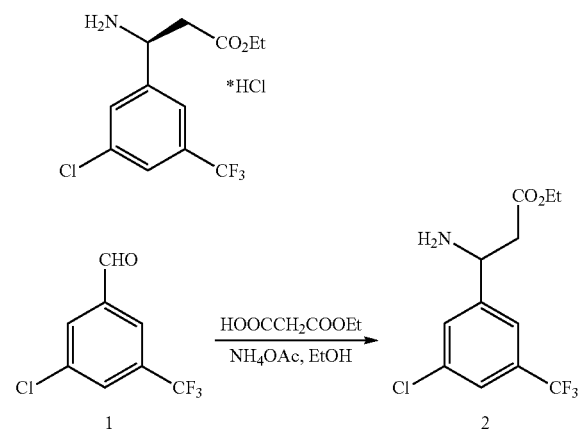

NH$_4$OAc (1.33 g, 0.12 mol), HOOCCH$_2$COOEt (4.5 g, 0.034 mol) and benzaldehyde 1 (3.6 g, 0.017 mol) in EtOH (30 mL) were stirred at 70° C. for 6 h. The mixture was concentrated and adjusted to pH=7.5 by addition of aq. NaHCO$_3$. The mixture was extracted with EtOAc (3×50 mL). The organic layer was washed with brine, dried with Na$_2$SO$_4$ and concentrated to dryness to give an oil. The crude product was purified via silica gel chromatography to give racemic compound 2 (1.5 g, 29.4%). The (S) enantiomer, Example E, was isolated using the enzymatic resolution procedures described for Example F (below).

Example F

Preparation of ethyl (3S)-3-amino-3-[3-bromo-5-(trifluoromethyl)phenyl]propanoate hydrochloride

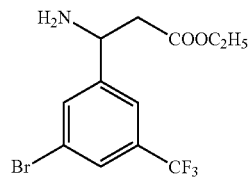

Step 1

Preparation of racemic ethyl 3-amino-3-[3-bromo-5-(trifluoromethyl)phenyl]propanoate

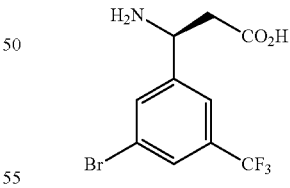

(rac)-Ethyl 3-amino-3-[3-bromo-5-(trifluoromethyl)phenyl]propanoate was prepared according to the method described for the preparation of Example E, substituting 3-bromo-5-trifluoromethyl benzaldehyde for 3-chloro-5-trifluoromethyl benzaldehyde.

Step 2

Preparation of (3S)-3-amino-3-[3-bromo-5-(trifluoromethyl)phenyl]propanoic acid

Enzymatic resolution of the racemic mixture: A suspension of (rac)-ethyl 3-amino-3-[3-bromo-5-(trifluoromethyl)phenyl]propanoate (570.0 mg, 1.676 mmol) in 50 mM KH$_2$PO$_4$ solution (30.0 mL) was stirred at room temperature and the pH of the aqueous layer was adjusted to pH 8.32 by the addition of 1.0 N NaOH solution and 50 mM KH$_2$PO$_4$ solution. Amano Lipase PS (625.0 mg) was added to the above suspension and the reaction mixture was stirred at room temperature for 2 days. The mixture was diluted with MTBE (25 mL) and reaction mixture was stirred at room temperature for 1 h to extract the (R)-ester. The MTBE layer containing the (R)-ester was discarded after analyzing by LC-MS. Evaporation of the aqueous layer in-vacuo afforded a cream solid containing the (S)-acid as well as Amano Lipase and Phosphate buffer salt. The above crude product was purified by reverse-phase HPLC with a gradient 10-60% CH3CN in water containing 0.05% TFA to give the desired product as a colorless glassy solid (231.0 mg). LC/MS analysis of the product shows the desired product's mass: m/z 312 ($^{79Br}$M+H), m/z 314 ($^{81Br}$M+H), m/z 334 ($^{79Br}$M+Na), and m/z 336 ($^{81Br}$M+Na); Calculated for m/z 314 ($^{81Br}$M+H), m/z 334 ($^{79Br}$M+Na), and m/z 336 ($^{81Br}$M+Na); Calculated for $C_{10}H_9BrF_3NO_2$: 312.08. The isolated TFA salt of the (S)-acid was used as such for the preparation of the (S)-ester.

Step 3

Preparation of ethyl (3S)-3-amino-3-[3-bromo-5-(trifluoromethyl)phenyl]propanoate hydrochloride (Example F)

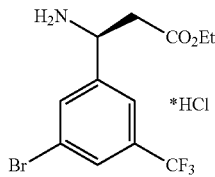

To a solution of (3S)-3-amino-3-[3-bromo-5-(trifluoromethyl)phenyl]propanoic acid TFA salt from step 2 above (231.0 mg, 0.542 mmol) in absolute ethanol (3 mL) was added absolute ethyl alcohol saturated with dry HCl gas (10 mL) and the reaction mixture was stirred at room temperature for 1.5 h. Evaporation of the solvent in-vacuo gave a colorless crystalline solid, (Example F) (198.5 mg, 97%). LC-MS analysis of the solid shows the desired product's mass: m/z 340 ($^{79Br}$M+H), m/z 342 ($^{81Br}$M+H), m/z 362 ($^{79Br}$M+Na), and m/z 364 ($^{81Br}$M+Na); Calculated for $C_{12}H_{13}BrF_3NO_2$: 340.14.

Example G

Preparation of ethyl (3S)-3-amino-3-[3-chloro-5-(trifluoromethoxy)phenyl]propanoate hydrochloride

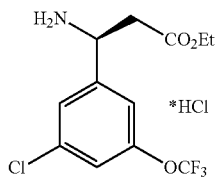 [SMILES: CCOC(=O)C[C@H](N)c1cc(Cl)cc(OC(F)(F)F)c1]

Step 1

Preparation of racemic ethyl 3-amino-3-[3-chloro-5-(trifluoromethoxy)phenyl]propanoate

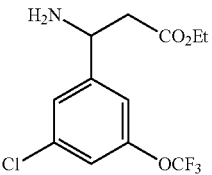

A solution of a mixture of 3-chloro-5-(trifluoromethoxy) benzaldehyde (1.05 g, 4.676 mmol) mono-ethyl malonate (1.54 g, 11.69 mmol) and ammonium acetate (1.985 g, 25.75 mmol) in absolute ethanol (30 mL) was heated at 80° C. overnight to give a colorless solution. The reaction mixture was cooled to room temperature and the solvent was evaporated in-vacuo to give a yellow viscous liquid. The residue was partitioned between aqueous saturated $NaHCO_3$ solution (50 mL) and ethyl acetate (50 mL), the organic layer was removed, dried over anhydrous sodium sulfate, filtered and evaporated in-vacuo to give a yellow-brown viscous liquid (1.56 g). LC-MS analysis of the crude product shows the desired product's mass: m/z 312 ($^{35Cl}$M+H), m/z 314 ($^{37Cl}$M+H), m/z 334 ($^{35Cl}$M+Na), and m/z 336 ($^{37Cl}$M+Na); Calculated for $C_{12}H_{13}ClF_3NO_3$: 311.68. LC-MS also shows the byproduct: (E)-ethyl 3-(3-chloro-5-(trifluoromethoxy) phenyl)acrylate's mass: m/z 295 ($^{35Cl}$M+H), and m/z 297 ($^{37Cl}$M+H); Calculated for $C_{12}H_{10}ClF_3O_3$: 294.65. To a solution of the crude residue in absolute ethanol (2 mL) was added a 2.0 M solution of HCl in diethyl ether (10.0 mL) and the reaction mixture was stirred at room temperature for 1 h to give a yellow solution. The residue after evaporation of the solvents was partitioned between water (25 mL) and dichloromethane (50 mL). The organic and the aqueous layers were separated. The aqueous layer was evaporated in-vacuo to afford a colorless gummy residue. The residue was purified by reverse-phase preparative HPLC with a gradient 10-70% $CH_3CN$ in water containing 0.05% TFA. The pure fractions mixture was evaporated in-vacuo to afford the desired product as a colorless crystalline solid (347.2 mg, yield 24%). LC/MS analysis of the product shows the desired product's mass: m/z 312 ($^{35Cl}$M+H), m/z 314 ($^{37Cl}$M+H), m/z 334 ($^{35Cl}$M+Na), and m/z 336 ($^{37Cl}$M+Na); Calculated for $C_{12}H_{13}ClF_3NO_3$: 311.68

Step 2

Preparation of racemic ethyl 3-amino-3-[3-chloro-5-(trifluoromethoxy)phenyl]propanoate hydrochloride

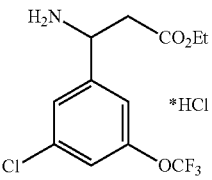 [SMILES: CCOC(=O)CC(N)c1cc(Cl)cc(OC(F)(F)F)c1]

To a solution of (rac)-ethyl 3-amino-3-[3-chloro-5-(trifluoromethoxy)phenyl]propanoate TFA salt from above (347.2 mg, 0.816 mmol) in absolute ethanol (2 mL) was added absolute ethyl alcohol saturated with dry HCl gas (5 mL) and the reaction mixture was stirred at room temperature for 30 min. Evaporation of the solvent in-vacuo gave a colorless gummy solid. The solid was slurried with hexanes (2×10 mL), the solvent layer was decanted off and the residue was dried in-vacuo to afford a colorless crystalline solid (270.7 mg, yield 95%). LC-MS analysis of the solid shows the desired product's mass: m/z 312 ($^{35Cl}$M+H), m/z 314 ($^{37Cl}$M+H), m/z 334 ($^{35Cl}$M+Na) and m/z 336 ($^{37Cl}$M+Na); Calculated for $C_{12}H_{13}ClF_3NO_3$: 311.68 $^1$H NMR (400 MHz, DMSO-$d_6$): δ 1.08 (t, J=7.1 Hz, 3H, $CH_3$—$CH_2$—), 3.06 (dd, J=16.1 and 8.8 Hz, 1H, CHH—C=O—), 3.20 (dd, J=16.4 and 10.3 Hz, 1H, —CHH—C=O—), 4.01 (q, J=7.1 and 2.0 Hz, 2H, $CH_3$—$CH_2$—), 4.72 (m, 1H, —$NH_2$—CH—$CH_2$—C=O—), 7.62 (s, 1H, H-2), 7.64 (s, 1H, H-6), 7.80 (s, 1H, H-4), 8.87 (brs, 3H, —$NH_2$.HCl). $^1$H NMR spectrum of the solid was consistent with the suggested structure of the product.

Step 3

Preparation of (3S)-3-amino-3-[3-chloro-5-(trifluoromethoxy)phenyl]propanoic acid

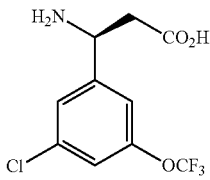 [SMILES: N[C@@H](CC(=O)O)c1cc(Cl)cc(OC(F)(F)F)c1]

Enzymatic resolution of the racemic mixture: A suspension of (rac)-ethyl 3-amino-3-[3-chloro-5-(trifluoromethoxy)phenyl]propanoate hydrochloride (185.30 mg, 0.532 mmol) in 50 mM $KH_2PO_4$ solution (25.0 mL) was stirred at room temperature and the pH of the aqueous layer was adjusted to pH 8.32 by the addition of 1.0 N NaOH solution and 50 mM $KH_2PO_4$ solution. Amano Lipase PS (201.0 mg) was added to above suspension and the reaction mixture was stirred at room temperature for 2 days. The mixture was diluted with MTBE (25 mL) and reaction mixture was stirred at room temperature for 1 h to extract the (R)-ester. The MTBE layer containing the (R)-ester was discarded after analyzing by LC-MS. Evaporation of the aqueous layer in-vacuo afforded a cream solid containing the (S)-acid as well as Amano Lipase and Phosphate buffer salt. The above crude product was purified by reverse-phase HPLC with a gradient 10-70% $CH_3CN$ in water containing 0.05% TFA to give the desired product as a colorless glassy solid (83.1 mg). LC/MS analysis of the product shows the desired product's mass: m/z 284 ($^{35Cl}$M+H), m/z 286 ($^{37Cl}$M+H), m/z 306 ($^{35Cl}$M+Na), and m/z 308 ($^{37Cl}$M+Na); Calculated for $C_{10}H_9ClF_3NO_3$: 283.63. The isolated TFA salt of the (S)-acid was used as such for the preparation of the (S)-ester.

Step 4

Preparation of ethyl (3S)-3-amino-3-[3-chloro-5-(trifluoromethoxy)phenyl]propanoate hydrochloride (Example G)

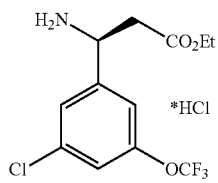 [SMILES: CCOC(=O)C[C@H](N)c1cc(Cl)cc(OC(F)(F)F)c1]

To a solution of (S)-3-amino-3-[3-chloro-5-(trifluoromethoxy)phenyl]propanoic acid TFA salt from Step 3 above (83.0 mg, 0.209 mmol), in absolute ethanol (2.0 mL), was added absolute ethyl alcohol saturated with dry HCl gas (5 mL) and the reaction mixture was stirred at room temperature for 1 h to give a colorless solution. LC-MS analysis of the reaction mixture after 1 h shows the desired product: ethyl (3S)-3-amino-3-[3-chloro-5-(trifluoromethoxy)phenyl]propanoate's mass: m/z 312 ($^{35Cl}$M+H), m/z 314 ($^{37Cl}$M+H), m/z 334 ($^{35Cl}$M+Na), and m/z 336 ($^{37Cl}$M+Na); Calculated for $C_{12}H_{13}ClF_3NO_3$: 311.68. The solvent was evaporated in-vacuo to afford the desired HCl salt of the ester (Example G) as a colorless crystalline solid (68.70 mg, yield 94%).

Example H

Preparation of ethyl (3S)-3-amino-3-[3-bromo-5-(trifluoromethoxy)phenyl]propanoate hydrochloride

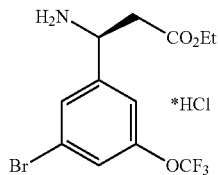

Step 1

Preparation of racemic ethyl 3-amino-3-[3-bromo-5-(trifluoromethoxy)phenyl]propanoate

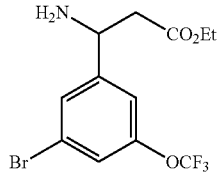 [SMILES: CCOC(=O)CC(N)c1cc(Br)cc(OC(F)(F)F)c1]

A solution of a mixture of 3-bromo-5-(trifluoromethoxy) benzaldehyde (1.05 g, 3.90 mmol) mono-ethyl malonate (1.31 g, 9.91 mmol) and ammonium acetate (1.68 g, 21.79 mmol) in absolute ethanol (25 mL) was heated at 80° C. for 5 h to give a colorless solution. The reaction mixture was cooled to room temperature and the solvent was evaporated in-vacuo to give a colorless viscous liquid. The residue was partitioned between aqueous saturated NaHCO$_3$ solution (50 mL) and ethyl acetate (50 mL), the organic layer was removed, dried over anhydrous sodium sulfate, filtered and evaporated in-vacuo to give a pale yellow viscous liquid (1.40 g). LC-MS analysis of the crude product shows the desired product's mass: m/z 356 ($^{79Br}$M+H), m/z 358 ($^{81Br}$M+H) m/z 378 ($^{79Br}$M+Na), and m/z 380 ($^{81Br}$M+Na); Calculated for C$_{12}$H$_{13}$BrF$_3$NO$_3$: 356.14. LC-MS also shows the byproduct: (E)-ethyl 3-(3-bromo-5-(trifluoromethoxy)phenyl)acrylate's mass: m/z 339 ($^{79Br}$M+H), and m/z 341 ($^{81Br}$M+H); Calculated for C$_{12}$H$_{10}$BrF$_3$O$_3$: 339.11. To a solution of the crude residue in absolute ethanol (2 mL) was added a 2.0 M solution of HCl in diethyl ether (15.0 mL) and the reaction mixture was stirred at room temperature for 30 min to give a pale yellow solution. The residue after evaporation of the solvents was partitioned between water (25 mL) and dichloromethane (25 mL). The organic and the aqueous layers were separated. The aqueous layer was evaporated in-vacuo to afford a colorless gummy residue. The residue was purified by reverse-phase preparative HPLC with a gradient 10-70% CH$_3$CN in water containing 0.05% TFA. The pure fractions mixture was evaporated in-vacuo to afford the desired product as a colorless crystalline solid (442.5 mg, yield 31%). LC/MS analysis of the product shows the desired product's mass: m/z 356 ($^{79Br}$M+H), m/z 358 ($^{81Br}$M+H), 378 ($^{79Br}$M+Na), and m/z 380 ($^{81Br}$M+Na); Calculated for C$_{12}$H$_{13}$BrF$_3$NO$_3$: 356.14.

Step 2

Preparation of racemic ethyl 3-amino-3-[3-bromo-5-(trifluoromethoxy)phenyl]propanoate hydrochloride

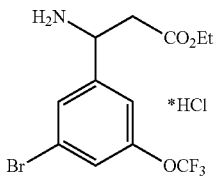

To a solution of (rac)-ethyl 3-amino-3-[3-bromo-5-(trifluoromethoxy)phenyl]propanoate TFA salt from above (442.8 mg, 0.942 mmol) in absolute ethanol (2 mL) was added a 2.0 M HCl solution in diethyl ether (10 mL) and the reaction mixture was stirred at room temperature for 1 h. Evaporation of the solvent in-vacuo gave a colorless gummy solid. The solid was slurried with hexanes (2×10 mL), the solvent layer was decanted off and the residue was dried in-vacuo to afford a colorless crystalline solid (358.0 mg, yield 96%). LC-MS analysis of the solid shows the desired product's mass: m/z 356 ($^{79Br}$M+H), m/z 358 ($^{81Br}$M+H), m/z 378 ($^{79Br}$M+Na), and m/z 380 ($^{81Br}$M+Na); Calculated for C$_{12}$H$_{13}$BrF$_3$NO$_3$: 356.14. $^1$H NMR (400 MHz, DMSO-d$_6$): δ 1.08 (t, J=7.1 Hz, 3H, CH$_3$—CH$_2$—), 3.095 (double AB q, J=16.4 and 8.7 Hz, and J=16.4 and 10.3 Hz, (each 1H), 2H, —CHH—C=O— and —CHH—C=O—; diastereotopic), 4.01 (dq, J=7.1 and 2.0 Hz, 2H, CH$_3$—CH$_2$—), 4.72 (dd, J=8.3 and 6.1 Hz, 1H, —NH$_2$—CH—CH$_2$—C=O—), 7.65 (appt, J=1.7 Hz, 1H), 7.73 (appt, J=1.7 Hz, 1H), 7.90 (appt, J=1.5 Hz, 1H), 8.74 (brs, 3H, —NH$_2$.HCl).

$^1$H NMR spectrum of the solid was consistent with the suggested structure of the product.

Step 3

Preparation of (3S)-3-amino-3-[3-bromo-5-(trifluoromethoxy)phenyl]propanoic acid

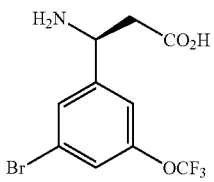

Enzymatic resolution of the racemic mixture:

A suspension of (rac)-ethyl 3-amino-3-[3-bromo-5-(trifluoromethoxy)phenyl]propanoate hydrochloride from step 2 above (345.40 mg, 0.880 mmol) in 50 mM KH$_2$PO$_4$ solution (30.0 mL) was stirred at room temperature and the pH of the aqueous layer was adjusted to pH 8.32 by the addition of 1.0 N NaOH solution and 50 mM KH$_2$PO$_4$ solution. Amano Lipase PS (317.0 mg) was added to above suspension and the reaction mixture was stirred at room temperature overnight. The mixture was diluted with MTBE (25 mL) and reaction mixture was stirred at room temperature for 1 h to extract the (R)-ester. The MTBE layer containing the (R)-ester was discarded after analyzing by LC-MS. Evaporation of the aqueous layer in-vacuo afforded a cream solid containing the (S)-acid as well as Amano Lipase and Phosphate buffer salt. The above crude product was purified by reverse-phase HPLC with a gradient 10-70% CH$_3$CN in water containing 0.05% TFA to give the desired product as a colorless glassy solid (201.3 mg). LC/MS analysis of the product shows the desired product's mass: m/z 328 ($^{79Br}$M+H), m/z 330 ($^{81Br}$M+H), m/z 350 ($^{79Br}$M+Na), and m/z 352 ($^{81Br}$M+Na), Calculated for C$_{10}$H$_9$BrF$_3$NO$_3$: 328.08. The isolated TFA salt of the (S)-acid was used as such for the preparation of the (S)-ester.

Step 4

Preparation of ethyl (3S)-3-amino-3-[3-bromo-5-(trifluoromethoxy)phenyl]propanoate hydrochloride (Example H)

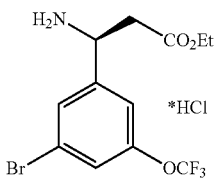 [SMILES: CCOC(=O)C[C@H](N)c1cc(Br)cc(OC(F)(F)F)c1]

To a solution of (S)-3-amino-3-[3-bromo-5-(trifluoromethoxy)phenyl]propanoic acid TFA salt from step 3 above (201.30 mg, 0.455 mmol) in absolute ethanol (2.0 mL) was added absolute ethyl alcohol saturated with dry HCl gas (5 mL) and the reaction mixture was stirred at room temperature for 1.5 h to give a colorless solution. LC-MS analysis of the reaction mixture after 1.5 h shows the desired product: (S)-ethyl 3-amino-3-[3-bromo-5-(trifluoromethoxy)phenyl]propanoate's mass: m/z 356 ($^{79Br}$M+H) m/z 358 ($^{81Br}$M+H) m/z 378 ($^{79Br}$M+Na), and m/z 380 ($^{81Br}$M+Na), Calculated for $C_{12}H_{13}BrF_3NO_3$: 356.14 The solvent was evaporated in-vacuo to afford the desired HCl salt of the ester (Example H) as a colorless crystalline solid (171.0 mg, yield 95%).

Example I

Preparation of ethyl (3S)-3-amino-3-[3,5-dichloro-phenyl]propanoate hydrochloride

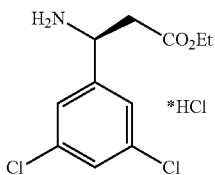 [SMILES: CCOC(=O)C[C@H](N)c1cc(Cl)cc(Cl)c1]

Step 1

Preparation of (S)-3-amino-3-[3,5-dichloro-phenyl]propanoic acid

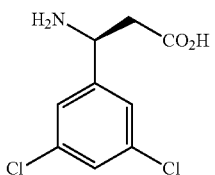 [SMILES: N[C@@H](CC(=O)O)c1cc(Cl)cc(Cl)c1]

Enzymatic Resolution of the Racemic Mixture:

A suspension of (rac)-ethyl 3-amino-3-[3,5-dichlorophenyl]propanoate hydrochloride (synthesized according to procedures described herein starting from 3,5-dichlorophenyl benzaldehyde) (316.0 mg, 1.058 mmol) in 50 mM $KH_2PO_4$ solution (30.0 mL) was stirred at room temperature and the pH of the aqueous layer was adjusted to pH 8.32 by the addition of 1.0 N NaOH solution and 50 mM $KH_2PO_4$ solution. Amano Lipase PS (295.0 mg) was added to above suspension and the reaction mixture was stirred at room temperature for 2 days. The mixture was diluted with MTBE (25 mL) and reaction mixture was stirred at room temperature for 1 h to extract the (R)-ester. The MTBE layer containing the (R)-ester was discarded after analyzing by LC-MS. Evaporation of the aqueous layer in-vacuo afforded a cream solid containing the (S)-acid as well as Amano Lipase and Phosphate buffer salt. The above crude product was purified by reverse-phase HPLC with a gradient 10-50% $CH_3CN$ in water containing 0.05% TFA to give the desired product as a colorless glassy solid (103.0 mg). LC/MS analysis of the product shows the desired product's mass: m/z 234 ($^{35Cl}$M+H), m/z 236 ($^{37Cl}$M+H) m/z 256 ($^{35Cl}$M+Na), and m/z 258 ($^{37Cl}$M+Na); Calculated for $C_9H_9Cl_2NO_2$: 234.08. The isolated TFA salt of the (S)-acid was used as such for the preparation of the (S)-ester.

Step 2

Preparation of ethyl (3S)-3-amino-3-[3,5-dichloro-phenyl]propanoate hydrochloride (Example I)

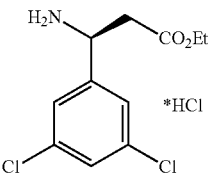 [SMILES: CCOC(=O)C[C@H](N)c1cc(Cl)cc(Cl)c1]

To a suspension of (S)-3-amino-3-[3,5-dichlorophenyl] propanoic acid from step 1 above (103.0 mg, 0.440 mmol) in absolute ethanol (2.0 mL) was added absolute ethyl alcohol saturated with dry HCl gas (5 mL) and the reaction mixture was stirred at room temperature for 1 h to give a colorless solution. LC-MS analysis of the reaction mixture after 1.5 h shows the desired product: (S)-ethyl 3-amino-3-[3,5-dichlorophenyl]propanoate's mass: m/z 262 ($^{35Cl}$M+H), m/z 264 ($^{37Cl}$M+H), m/z 284 ($^{35Cl}$M+Na), and m/z 286 ($^{37Cl}$M+Na); Calculated for $C_{11}H_{13}Cl_2NO_2$: 262.13. The solvent was evaporated in-vacuo to afford the desired HCl salt of the ester (Example I) as a colorless crystalline solid (131.20 mg, yield 99%).

Example J

Preparation of racemic ethyl 3-amino-3-[3,5-bromophenyl]propanoate hydrochloride

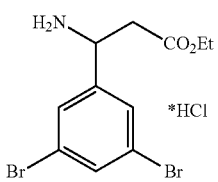 [SMILES: CCOC(=O)CC(N)c1cc(Br)cc(Br)c1]

Step 1

Preparation of racemic 3-amino-3-[3,5-bromo-phenyl]propanoic acid

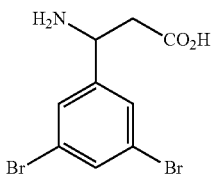

A suspension of 3,5-dibromo-benzaldehyde (50 g, 189.39 mmol), malonic acid (39.39 g, 378.78 mmol) and ammonium acetate (29.19 g, 378.78 mmol) in isopropanol (350 mL) was heated at reflux under nitrogen for 14 h to afford a thick colorless solid. The solid was filtered hot, washed with hot isopropanol (2×100 mL) and dried in vacuo to give the desired racemic product as a colorless solid (32.2 g).

Step 2

Preparation of racemic ethyl 3-amino-3-[3,5-bromophenyl]propanoate hydrochloride

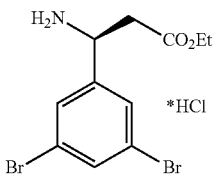

Absolute ethanol (500 mL, saturated with anhydrous HCl gas) was added to 3-amino-3-(3,5-dibromo-phenyl)-propionic acid from step 1 above (32 g, 99.07 mmol) and the reaction mixture was heated to reflux for 1.5 h to give a pale yellow solution. The solvent was removed in vacuo to give a colorless solid. The solid was washed with hexane (2×100 mL). After the solvent layer was decanted off, the residue was dried in vacuo to give the racemic amino ester hydrochloride salt (Example J) as a white solid (38 g).

Example K

Preparation of ethyl (3S)-3-amino-3-[3-bromo-5-(di-fluoromethyl)phenyl]propanoate hydrochloride

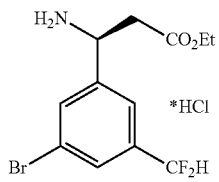

Step 1

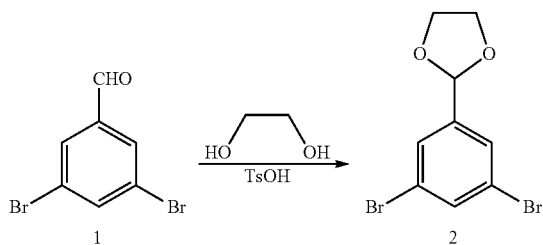

3,5-dibromo benzaldehyde 1 (10 g, 37.8 mmol, 1.0 eq), ethane-1,2-diol (7.0 g, 114 mmol, 3.0 eq) and TsOH (0.32 g, 1.89 mmol) in toluene (20 mL) was stirred at 110° C. for 4 h. The mixture was cooled to 23° C. and concentrated, extracted with EtOAc. The organic layer was washed with brine, dried (Na$_2$SO$_4$) and concentrated to dryness to give compound 2 (9.2 g, 83.6%) as an oil.

Step 2

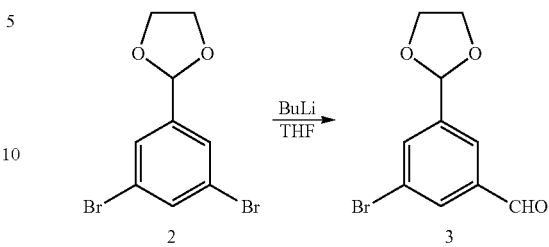

Compound 2 (9.2 g, 29.8 mmol, 1.0 eq) in THF (100 mL) was stirred at −78° C. n-BuLi (12 mL, 1.0 eq) was added dropwise to above mixture at −78° C. The mixture was stirred at −78° C. for 1 h. DMF (4.56 g, 1.5 eq) was added dropwise to above mixture at −78° C. The mixture was stirred at −78° C. for 3 h then warmed to 25° C. Water was added to the mixture and then extracted with ethyl acetate. The organic layer was washed with brine, dried (Na$_2$SO$_4$) and concentrated to dryness to give crude product. The crude product was purified by silica gel chromatograph to give compound 3 (6.6 g, 86.8%) as a white solid.

Step 3

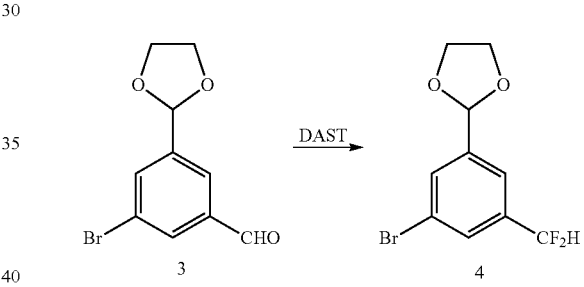

Compound 3 (6.6 g, 0.026 mol) was added to DCM (50 mL), then DAST (8.3 g, 0.052 mol) was added to the solution and the reaction was stirred for 8 h under N$_2$. The solution was washed with aq. NaHCO$_3$, and the mixture was extracted with DCM. The organic layer was washed with brine, dried (Na$_2$SO$_4$) and concentrated. The crude material was purified by silica gel chromatograph to give compound 4 (4.2 g, 58.3%).

Step 4

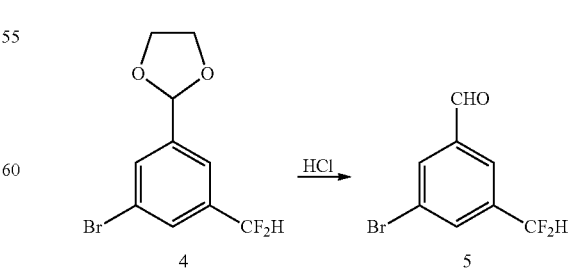

Compound 4 (4.2 g, 0.026 mol) was added to a solution of THF (40 mL) and 3N HCl (20 mL) and the reaction was stirred for 6 h. The mixture was concentrated and the crude product was purified by silica gel chromatography to give compound 5 (3.6 g, 76.9%).

Step 5

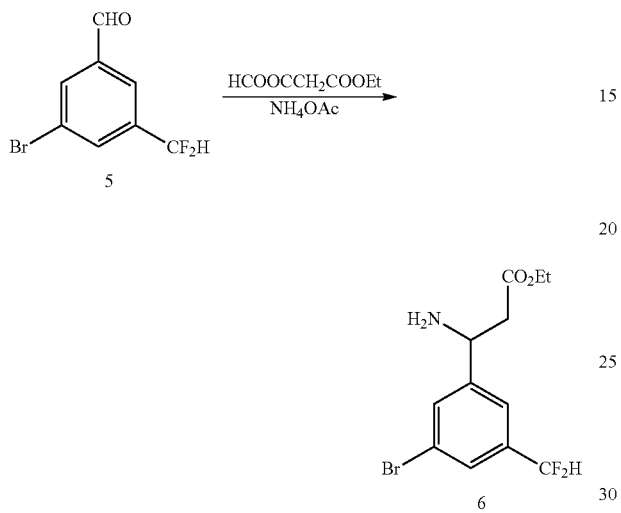

NH₄OAc (0.54 g, 0.077 mol), HOOCCH₂COOEt (2.9 g, 0.022 mol) and compound 5 (3.6 g, 0.011 mol), in EtOH (30 mL) were stirred at 70° C. for 6 h. The mixture was concentrated and adjusted to pH=7.5 by addition of aq. NaHCO₃. The mixture was extracted with EtOAc. The organic layer was washed with brine, dried (Na₂SO₄) and concentrated to dryness to give oil. The crude was purified by silica gel chromatography to give compound 6 (0.6 g, 17.1%). The (S) enantiomer, Example K, was isolated using the enzymatic resolution procedures described above.

Example L

Preparation of ethyl (3S)-3-amino-3-[3-chloro-5-(difluoromethyl)phenyl]propanoate hydrochloride

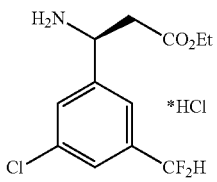

Example L was synthesized as described in the procedure for Example K, but substituting 3-bromo-5-chloro benzaldehyde for 3,5-di-bromo benzaldehyde in Step 1.

Example 1

Preparation of (3S)-3-(3,5-dibromophenyl)-3-(2-(3-hydroxy-5-((5-hydroxy-1,4,5,6-tetrahydropyrimidin-2-yl)amino)benzamido)acetamido)propanoic acid

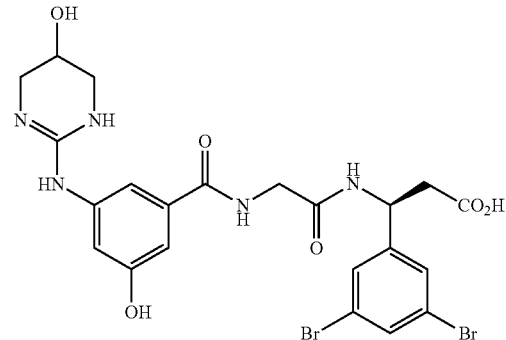

Step 1

Preparation of ethyl (3S) 3-[3,5-dibrom-phenyl]-3-(2-(3-hydroxy-5-((5-hydroxy-1,4,5,6-tetrahydropyrimidin-2-yl)amino)benzamido)acetamido]propanoate

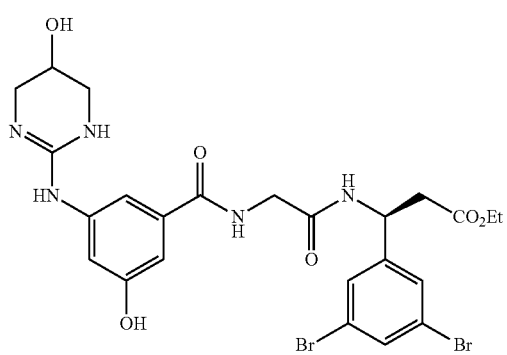

A mixture of 2-(3-hydroxy-5-((5-hydroxy-1,4,5,6-tetrahydropyrimidin-2-yl)amino)benzamido)acetic acid (Example B) (513.80 mg, 1.667 mmol), ethyl (3S)-3-amino-3-(3,5-dibromophenyl) propanoate hydrochloride (the (S) ester of Example J formed via the enzymatic lipase cleavage method) (645.80 mg, 1.667 mmol) and 1-hydroxybenzotriazole hydrate (52.0 mg, 0.340 mmol) was dissolved in a mixture of DMF (6 mL) and dichloromethane (6 mL) and the reaction mixture was stirred under nitrogen atmosphere for 10 min to give a cream suspension. Neat N,N'-diisopropylcarbodiimide (360.0 µL, 2.325 mmol) was added and the reaction mixture was stirred at room temperature under nitrogen atmosphere overnight. The solvent was evaporated in-vacuo to give a colorless viscous residue of the product: ethyl (3S)-3-[3,5-dibromophenyl]-3-[[2-[[3-hydroxy-5-[(5-hydroxy-1,4,5,6-tetrahydropyrimidin-2-yl)amino]benzoyl]amino]acetyl]amino]propanoate. LC-MS analysis of the crude residue shows the desired product's mass: m/z 640 ($^{79Br,79Br}$M+H), m/z 642 ($^{79Br,81Br}$M+H), m/z 644 ($^{81Br,81Br}$M+H), m/z 662 ($^{79Br,79Br}$M+Na), m/z 664 ($^{79Br,81Br}$M+Na), and m/z 666 ($^{81Br,81Br}$M+Na); Calculated for $C_{24}H_{27}Br_2N_5O_6$: 641.31. The crude residue was used as such for the saponification reaction in Step 2.

Step 2

Preparation of (3S)-3-(3,5-dibromophenyl)-3-(2-(3-hydroxy-5-((5-hydroxy-1,4,5,6-tetrahydropyrimidin-2-yl)amino)benzamido)acetamido)propanoic acid

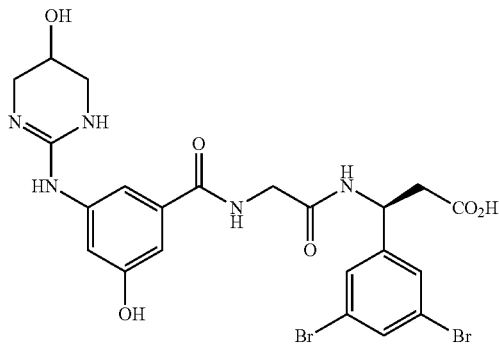

To a solution of crude ethyl (3S)-3-[3,5-dibromophenyl]-3-[[2-[[3-hydroxy-5-[(5-hydroxy-1,4,5,6-tetrahydropyrimidin-2-yl)amino]benzoyl]amino]acetyl]amino]propanoate from step 1 above (1.667 mmol) in a mixture of a 1:1 mixture of acetonitrile/water (10 mL) was added lithium hydroxide monohydrate (350.0 mg, 8.341 mmol) at room temperature and the reaction mixture was stirred at room temperature for 1 h. The mixture was neutralized with TFA (1.0 mL in 10.0 mL $CH_3CN$) and the mixture was evaporated in-vacuo to give a colorless gummy residue. The above crude product was purified by reverse-phase HPLC with a gradient 10-70% $CH_3CN$ in water containing 0.05% TFA to give the desired product, after lyophilization, as a colorless lyophilized solid (Example 1) (684.2 mg, yield 67%). LC/MS analysis of the product shows the desired product's mass: m/z 612 ($^{79Br,79Br}$M+H) m/z 614 ($^{79Br,81Br}$M+H), and m/z 616 ($^{81Br,81Br}$M+H); Calculated for $C_{22}H_{23}Br_2N_5O_6$: 613.26. $^1$H NMR (400 MHz, DMSO-$d_6$): δ 2.74 (d, J=7.10 Hz, 2H), 3.16 (d, J=12.23 Hz, 2H), 3.33 (d, J=11.25 Hz, 2H), 3.86 (d, J=5.87 Hz, 2H), 4.08 (brs, 1H), 5.14 (q, J=7.34 Hz, 1H), 6.74 (appt, J=2.0 Hz, 1H), 7.11 (appt, 1H), 7.14 (appt, J=1.7 Hz, 1H), 7.56 (d, J=1.71 Hz, 2H), 7.71 (t, J=1.7 Hz, 1H), 8.11 (s, 1H), 8.53 (d, J=7.8 Hz, 1H), 8.64 (t, J=6.0 Hz, 1H), 9.61 (s, 1H), 10.01 (brs, 1H), 12.40 (brs, 1H). $^1$H NMR spectrum of the sample was consistent with the proposed structure for Example 1.

Example 2

Preparation of (3S)-3-(3-bromo-5-(trifluoromethyl)phenyl)-3-(2-(3-hydroxy-5-((5-hydroxy-1,4,5,6-tetrahydropyrimidin-2-yl)amino)benzamido)acetamido)propanoic acid

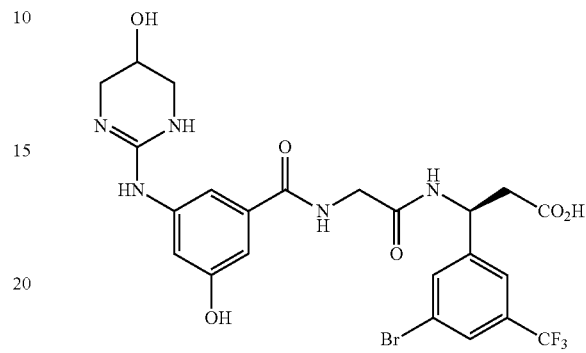

Step 1

Preparation of ethyl (3S) 3-(3-bromo-5-(trifluoromethyl)phenyl)-3-(2-(3-hydroxy-5-((5-hydroxy-1,4,5,6-tetrahydropyrimidin-2-yl)amino)benzamido)acetamido)propanoate

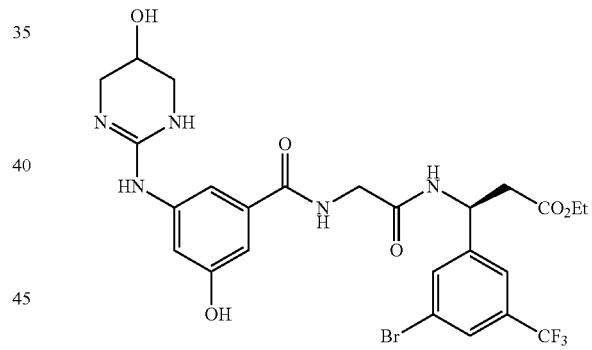

A mixture of 2-(3-hydroxy-5-((5-hydroxy-1,4,5,6-tetrahydropyrimidin-2-yl)amino)benzamido)acetic acid (Example B) (83.0 mg, 0.269 mmol), ethyl (3S)-3-amino-3-(3-bromo-5-(trifluoromethyl)phenyl)propanoate hydrochloride (Example F) (102.0 mg, 0.271 mmol) was dissolved in DMF (4 mL) and dichloromethane (4 mL) to give a cream suspension. Solid 1-hydroxybenzotriazole hydrate (8.7 mg, 0.057 mmol) was added to above reaction mixture and the reaction mixture was stirred under nitrogen atmosphere for 10 min. N,N'-diisopropylcarbodiimide (60.0 μL, 0.387 mmol) was added and the reaction mixture was stirred at room temperature under nitrogen atmosphere overnight. The solvent was evaporated in-vacuo to give a colorless gummy residue of the product: ethyl (3S)-3-[3-bromo-5-(trifluoromethyl)phenyl]-3-[[2-[[3-hydroxy-5-[(5-hydroxy-1,4,5,6-tetrahydropyrimidin-2-yl)amino]benzoyl]amino]acetyl]amino]propanoate. LC-MS analysis of the crude residue shows the desired product's mass: m/z 630 ($^{79Br}$M+H), m/z 632 ($^{81Br}$M+H), m/z 652 ($^{79Br}$M+Na), and m/z 654 ($^{81Br}$m+

Na); Calculated for $C_{25}H_{27}BrF_3N_5O_6$: 630.41. The crude residue was used as such for the saponification reaction in step 2.

Step 2

Preparation of (3S)-3-(3-bromo-5-(trifluoromethyl)phenyl)-3-(2-(3-hydroxy-5-((5-hydroxy-1,4,5,6-tetrahydropyrimidin-2-yl)amino)benzamido)acetamido)propanoic acid

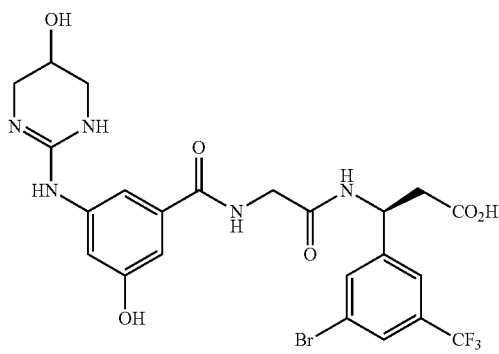

To a solution of crude ethyl (3S)-3-[3-bromo-5-(trifluoromethyl)phenyl]-3-[[2-[[3-hydroxy-5-[(5-hydroxy-1,4,5,6-tetrahydropyrimidin-2-yl)amino]benzoyl]amino]acetyl]amino]propanoate from step 1 above (0.344 mmol) in a mixture of a 1:1 mixture of acetonitrile/water (4 mL) was added lithium hydroxide monohydrate (77.0 mg, 1.83 mmol) at room temperature and the reaction mixture was stirred at room temperature for 1.5 h. The mixture was neutralized with TFA (1.0 mL in 10.0 mL $CH_3CN$) and the mixture was evaporated in-vacuo to give a colorless gummy residue. The above crude product was purified by reverse-phase HPLC with a gradient 10-60% $CH_3CN$ in water containing 0.05% TFA to give the desired product, after lyophilization, as a colorless lyophilized solid (Example 2) (124.0 mg, yield 60%). LC/MS analysis of the product shows the desired product's mass: m/z 602 ($^{79Br}$M+H), and m/z 604 ($^{81Br}$M+H); Calculated for $C_{23}H_{23}BrF_3N_5O_6$: 602.36. $^1$H NMR (400 MHz, DMSO-$d_6$): δ 2.78 (d, J=7.3 Hz, 2H), 3.16 (d, J=12.2 Hz, 2H), 3.33 (d, J=12.2 Hz, 2H), 3.87 (d, J=5.8 Hz, 2H), 4.08 (appt, J=3.07 Hz, 1H), 5.23 (q, J=7.3 Hz, 1H), 6.74 (t, J=2.1 Hz, 1H), 7.11 (t, J=1.8 Hz, 1H), 7.14 (t, J=1.8 Hz, 1H), 7.72 (s, 1H), 7.85 (s, 1H), 7.87 (s, 1H), 8.10 (brs, 2H), 8.61 (d, J=7.9 Hz, 1H), 8.64 (t, J=5.9 Hz, 1H), 9.60 (s, 1H), 10.02 (brs, 1H), 12.41 (brs, 1H, —COOH). $^1$H NMR spectrum of the product was consistent with the proposed structure for Example 2. $^{19}$F NMR (376 MHz, DMSO-$d_6$): δ −61.09 (s), and −73.82 (s).

Example 3

Preparation of (3S)-3-[3-chloro-5-(difluoromethyl)phenyl)-3-(2-(3-hydroxy-5-((5-hydroxy-1,4,5,6-tetrahydropyrimidin-2-yl)amino)benzamido)acetamido]propanoic acid

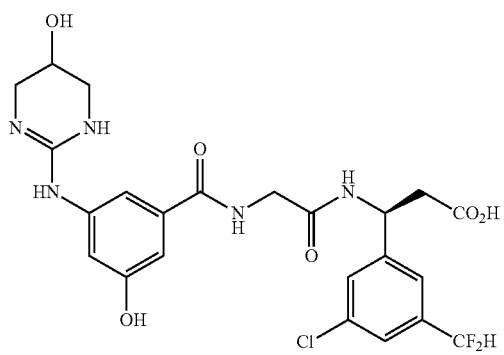

Step 1

Preparation of (3S)-ethyl 3-[3-chloro-5-(difluoromethyl)phenyl)-3-(2-(3-hydroxy-5-((5-hydroxy-1,4,5,6-tetrahydropyrimidin-2-yl)amino)benzamido)acetamido]propanoate

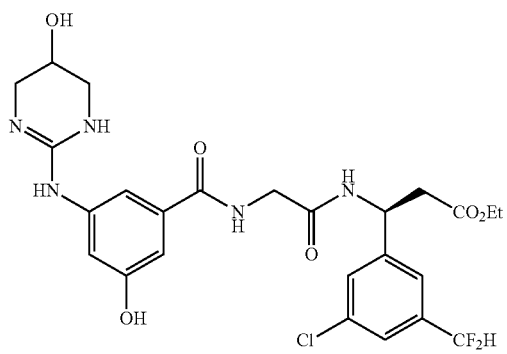

A mixture of 2-(3-hydroxy-5-((5-hydroxy-1,4,5,6-tetrahydropyrimidin-2-yl)amino)benzamido)acetic acid (Example B) (27.0 mg; 0.088 mmol), (S)-ethyl 3-amino-3-(3-chloro-5-(1-(difluoromethyl)phenyl)propanoate hydrochloride (Example L) (27.51 mg, 0.088 mmol) was dissolved in DMF (1 mL) and dichloromethane (1 mL) to give a colorless suspension. Solid 1-hydroxybenzotriazole hydrate (3.0 mg, 0.020 mmol) was added to above reaction mixture and the reaction mixture was stirred under nitrogen atmosphere for 10 min. N,N'-diisopropylcarbodiimide (20.0 µL, 0.129 mmol) was added and the reaction mixture was stirred at room temperature under nitrogen atmosphere overnight. The solvent was evaporated in-vacuo to give a pale yellow viscous residue of the product: (3S)-ethyl 3-(3-chloro-5-(difluoromethyl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 568 ($^{35Cl}$M+H), m/z 570 ($^{37Cl}$M+H), m/z 590 ($^{35Cl}$M+Na), and m/z 592 ($^{37Cl}$M+Na); Calculated for $C_{25}H_{28}ClF_2N_5O_6$: 567.97. The crude residue was used as such for the saponification reaction in Step 2.

Step 2

Preparation of (3S)-3-[3-chloro-5-(difluoromethyl)phenyl)-3-(2-(3-hydroxy-5-((5-hydroxy-1,4,5,6-tetrahydropyrimidin-2-amino)benzamido)acetamido]propanoic acid

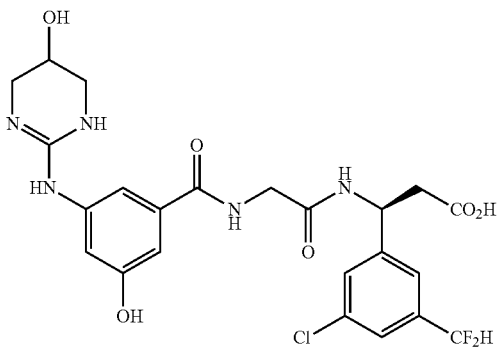 [SMILES: O=C(O)C[C@H](NC(=O)CNC(=O)c1cc(O)cc(NC2=NCC(O)CN2)c1)c1cc(Cl)cc(C(F)F)c1]

To a suspension of crude (3S)-ethyl 3-(3-chloro-5-(difluoromethyl)phenyl)-3-(2-(3-hydroxy-5-((5-hydroxy-1,4,5,6-tetrahydropyrimidin-2-yl)amino)benzamido)acetamido)propanoate from step 1 above (0.088 mmol) in a mixture of a 1:1 mixture of acetonitrile/water (4 mL) was added lithium hydroxide monohydrate (20.0 mg, 0.477 mmol) at room temperature and the reaction mixture was stirred at room temperature overnight. The mixture was neutralized with TFA (1 mL in 10.0 mL $CH_3CN$) and the mixture was evaporated in-vacuo to give a yellow gummy residue. The above crude product was purified by reverse-phase HPLC with a gradient 10-60% CH3CN in water containing 0.05% TFA to give the desired product, after lyophilization, as a colorless lyophilized solid (Example 3) (41.2 mg, yield 87%). LC/MS analysis of the product shows the desired product's mass: m/z 540 ($^{35Cl}$M+H) and m/z 542 ($^{37Cl}$M+H), Calculated for $C_{23}H_{24}ClF_2N_5O_6$: 539.92. $^1$H NMR (400 MHz, DMSO-$d_6$): δ 2.76 (d, J=7.34 Hz, 2H, —$CH_2$—COOH), 3.16 (d, J=12.23 Hz, 2H), 3.33 (d, J=10.76 Hz, 2H), 3.87 (dd/m, 3H), 4.08 (t, J=3.18 Hz, 1H), 5.21 (q, J=7.34 Hz, 1H, —NH—CH—$CH_2$—COOH), 6.74 (t, J=2.08 Hz, 1H), 7.03 (s, 1H), 7.11 (t, J=1.71 Hz, 1H), 7.13 (apt, 1H), 7.53 (brs, 1H), 7.59 (s, 1H), 8.14 (brs, 2H), 8.63 (t, J=5.87 Hz, 1H), 9.67 (brs, 1H), 10.02 (brs, 1H), 12.44 (brs, 1H, —COOH). $^1$H NMR spectrum of the product was consistent with the proposed structure for Example 3. $^{19}$F NMR (376 MHz, DMSO-$d_6$): δ −74.12 (s), and −110.28 (d, J=56.0 Hz).

Example 4

Preparation of (3S)-3-[3-bromo-5-(difluoromethyl)phenyl)-3-(2-(3-hydroxy-5-((5-hydroxy-1,4,5,6-tetrahydropyrimidin-2-yl)amino)benzamido)acetamido]propanoic acid

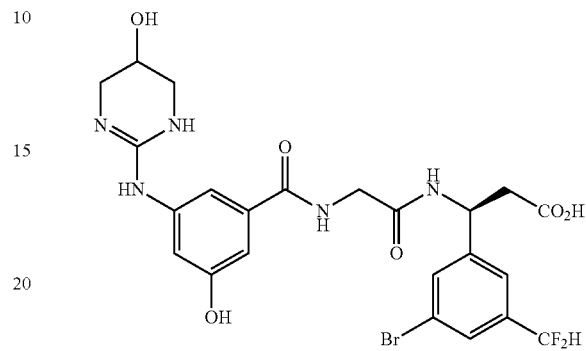

Step 1

Preparation of (3S)-ethyl 3-[3-bromo-5-(difluoromethyl)phenyl)-3-(2-(3-hydroxy-5-((5-hydroxy-1,4,5,6-tetrahydropyrimidin-2-yl)amino)benzamido)acetamido]propanoate

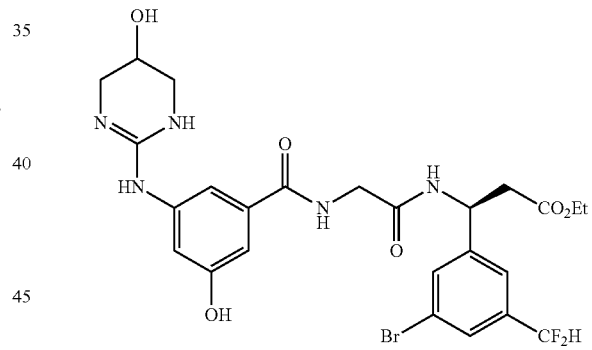

A mixture of 2-(3-hydroxy-5-((5-hydroxy-1,4,5,6-tetrahydropyrimidin-2-yl)amino)benzamido)acetic acid (Example B) (25.0 mg; 0.081 mmol), ethyl (3S)-3-amino-3-(3-bromo-5-(1-(difluoromethyl)phenyl)propanoate hydrochloride (Example K) (29.08 mg, 0.081 mmol) was dissolved in DMF (1 mL) and dichloromethane (1 mL) to give a colorless suspension. Solid 1-hydroxybenzotriazole hydrate (3.0 mg, 0.020 mmol) was added to above reaction mixture and the reaction mixture was stirred under nitrogen atmosphere for 10 min. N,N'-diisopropylcarbodiimide (20.0 µL, 0.129 mmol) was added and the reaction mixture was stirred at room temperature under nitrogen atmosphere overnight. The solvent was evaporated in-vacuo to give a yellow orange viscous residue of the product: (3S)-ethyl 3-(3-bromo-5-(difluoromethyl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 612 ($^{79Br}$M+H), m/z 614 ($^{81Br}$M+H), m/z 634 ($^{79Br}$M+Na), and m/z 636 ($^{81Br}$M+Na); Calculated for $C_{25}H_{28}BrF_2N_5O_6$: 612.42. The crude residue will be used as such for the saponification reaction in Step 2.

Step 2

Preparation of (3S)-[3-bromo-5-(difluoromethyl)phenyl)-3-(2-(3-hydroxy-5-((5-hydroxy-1,4,5,6-tetrahydropyrimidin-2-amino)benzamido)acetamido]propanoic acid

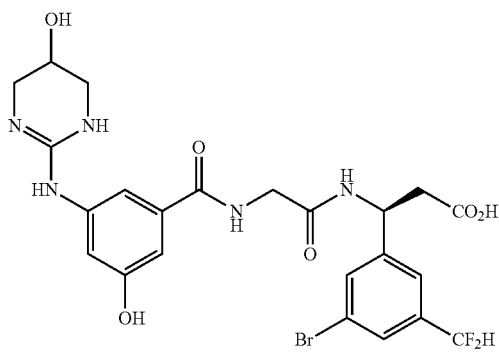 [SMILES: O=C(O)C[C@H](NC(=O)CNC(=O)c1cc(O)cc(NC2=NCC(O)CN2)c1)c1cc(Br)cc(C(F)F)c1]

To a suspension of crude ethyl (3S)-3-(3-bromo-5-(difluoromethyl)phenyl)-3-(2-(3-hydroxy-5-((5-hydroxy-1,4,5,6-tetrahydropyrimidin-2-yl)amino)benzamido)acetamido)propanoate from step 1 above (0.080 mmol) in a mixture of a 1:1 mixture of acetonitrile/water (4 mL) was added lithium hydroxide monohydrate (18.0 mg, 0.429 mmol) at room temperature and the reaction mixture was stirred at room temperature overnight. The mixture was neutralized with TFA (500 µL in 5.0 mL CH$_3$CN) and the mixture was evaporated in-vacuo to give a yellow gummy residue. The above crude product was purified by reverse-phase HPLC with a gradient 10-60% CH$_3$CN in water containing 0.05% TFA to give the desired product, after lyophilization, as a colorless lyophilized solid (Example 4) (33.4 mg, yield 71%). LC/MS analysis of the product shows the desired product's mass: m/z 584 ($^{79Br}$M+H), m/z 586 ($^{81Br}$M+H), m/z 606 ($^{79Br}$M+Na), and m/z 608 ($^{81Br}$M+Na); Calculated for $C_{23}H_{24}BrF_2N_5O_6$: 584.37. $^1$H NMR (400 MHz, DMSO-d$_6$): δ 2.76 (d, J=7.34 Hz, 2H, —CH$_2$—COOH), 3.16 (d, J=12.47 Hz, 2H), 3.33 (d, J=10.76 Hz, 2H), 3.87 (dd/m, 3H), 4.08 (t, J=2.90 Hz, 1H), 5.21 (q, J=7.34 Hz, 1H, —NH—CH—CH$_2$—COOH), 6.74 (t, J=2.08 Hz, 1H), 7.02 (appt, 1H), 7.14 (appt, 1H), 7.56 (s, 1H), 7.66 (s, 1H), 7.72 (s, 1H), 8.13 (brs, 1H), 8.58 (s, 1H), 8.62 (t, J=5.99 Hz, 1H), 9.65 (brs, 1H), 10.02 (brs, 1H), 12.40 (brs, 1H, —COOH). $^1$H NMR spectrum of the product was consistent with the proposed structure for Example 4. $^{19}$F NMR (376 MHz, DMSO-d$_6$): δ −73.81 (s), and −110.23 (d, J=56.0 Hz).

Example 5

Preparation of (3S)-3-[3-chloro-5-(trifluoromethyl)phenyl)-3-(2-(3-hydroxy-5-((5-hydroxy-1,4,5,6-tetrahydropyrimidin-2-yl)amino)benzamido)acetamido]propanoic acid

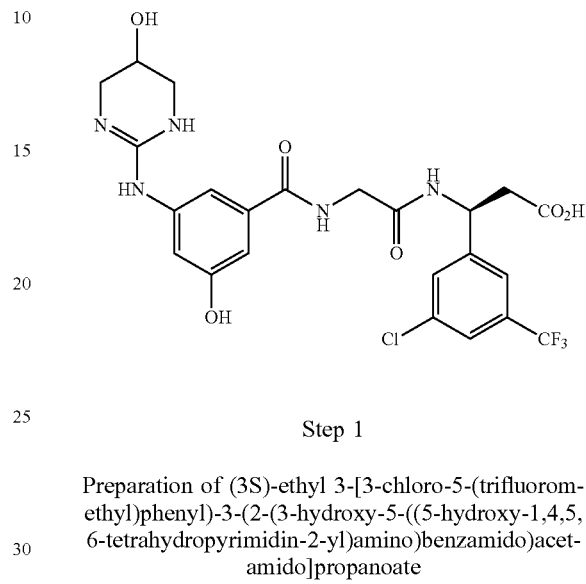

Step 1

Preparation of (3S)-ethyl 3-[3-chloro-5-(trifluoromethyl)phenyl)-3-(2-(3-hydroxy-5-((5-hydroxy-1,4,5,6-tetrahydropyrimidin-2-yl)amino)benzamido)acetamido]propanoate

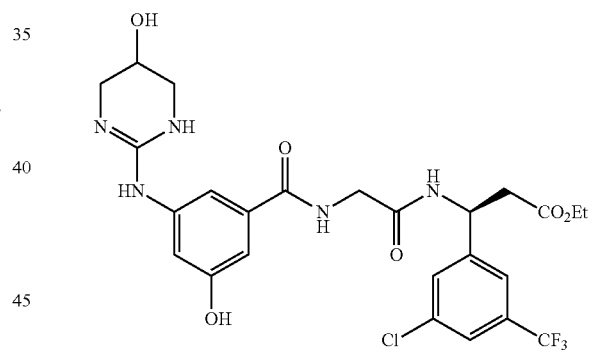

A mixture of 2-(3-hydroxy-5-((5-hydroxy-1,4,5,6-tetrahydropyrimidin-2-yl)amino)benzamido)acetic acid (Example B) (43.0 mg; 0.139 mmol), ethyl (3S)-3-amino-3-(3-chloro-5-(1-(trifluoromethyl)phenyl)propanoate hydrochloride (Example E) (46.33 mg, 0.139 mmol) was dissolved in DMF (1 mL) and dichloromethane (1 mL) to give a colorless suspension. Solid 1-hydroxybenzotriazole hydrate (4.40 mg, 0.029 mmol) was added to above reaction mixture and the reaction mixture was stirred under nitrogen atmosphere for 10 min. N,N'-diisopropylcarbodiimide (32.0 µL, 0.207 mmol) was added and the reaction mixture was stirred at room temperature under nitrogen atmosphere overnight. The solvent was evaporated in-vacuo to give a colorless gummy residue of the product: (3S)-ethyl 3-(3-chloro-5-(trifluoromethyl)phenyl)-3-(2-(3-hydroxy-5-((5-hydroxy-1,4,5,6-tetrahydropyrimidin-2-yl)amino)benzamido)

acetamido)propanoate. LC-MS analysis of the crude residue shows the desired product's mass: m/z 586 ($^{35Cl}$M+H), m/z 588 ($^{37Cl}$M+H) m/z 608 ($^{35Cl}$M+Na), and m/z 610 ($^{37Cl}$M+Na); Calculated for $C_{25}H_{27}ClF_3N_5O_6$: 585.96. The crude residue was used as such for the saponification reaction in step 2.

Step 2

Preparation of (3S)-3-[3-chloro-5-(trifluoromethyl)phenyl)-3-(2-(3-hydroxy-5-((5-hydroxy-1,4,5,6-tetrahydropyrimidin-2-yl)amino)benzamido)acetamido]propanoic acid

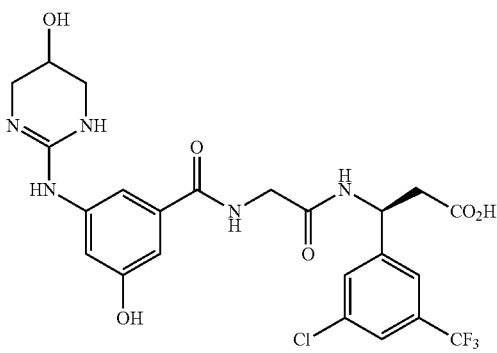

To a suspension of crude ethyl (3S)-3-(3-chloro-5-(trifluoromethyl)phenyl)-3-(2-(3-hydroxy-5-((5-hydroxy-1,4,5,6-tetrahydropyrimidin-2-yl)amino)benzamido)acetamido)propanoate from step 1 above (0.139 mmol) in a mixture of a 1:1 mixture of acetonitrile/water (4 mL) was added lithium hydroxide monohydrate (30.0 mg, 0.715 mmol) at room temperature and the reaction mixture was stirred at room temperature overnight. The mixture was neutralized with TFA (1 mL in 10.0 mL $CH_3CN$) and the mixture was evaporated in-vacuo to give a cream gummy residue. The above crude product was purified by reverse-phase HPLC with a gradient 10-60% $CH_3CN$ in water containing 0.05% TFA to give the desired product, after lyophilization, as a colorless lyophilized solid (Example 5) (63.2 mg, yield 81%)). LC/MS analysis of the product shows the desired product's mass: m/z 558 ($^{35Cl}$M+H) and m/z 560 ($^{37Cl}$M+H), Calculated for $C_{23}H_{23}ClF_3N_5O_6$: 557.91. $^1$H NMR (400 MHz, DMSO-$d_6$): δ 2.79 (d, J=7.09 Hz, 2H, —$CH_2$—COOH), 3.16 (d, J=11.98 Hz, 2H), 3.33 (d, J=11.00 Hz, 2H), 3.87 (d, J=5.87 Hz, 2H), 4.08 (t, J=3.18 Hz, 1H), 5.24 (q, J=7.09 Hz, 1H, —NH—CH—$CH_2$—COOH), 6.75 (s, 1H), 7.11 (s, 1H), 7.13 (t, J=2.00 Hz, 1H), 7.69 (s, 1H), 7.74 (s, 1H), 8.12 (brs, 1H), 8.61 (d, J=8.07 Hz, 1H), 8.65 (t, J=5.75 Hz, 1H), 9.66 (brs, 1H), 10.02 (brs, 1H), 12.43 (brs, 1H, —COOH). $^1$H NMR spectrum of the product was consistent with the proposed structure for Example 5. $^{19}$F NMR (376 MHz, DMSO-$d_6$): δ −61.11 (s), and −73.94 (s).

Example 6

Preparation of (3S)-3-[3-bromo-5-chloro-phenyl)-3-(2-(3-hydroxy-5-((5-hydroxy-1,4,5,6-tetrahydropyrimidin-2-yl)amino)benzamido)acetamido]propanoic acid

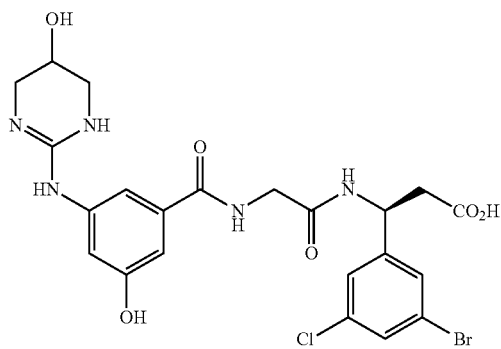

Step 1

Preparation of (3S)-ethyl 3-[3-bromo-5-chloro-phenyl)-3-(2-(3-hydroxy-5-((5-hydroxy-1,4,5,6-tetrahydropyrimidin-2-yl)amino)benzamido)acetamido]propanoate

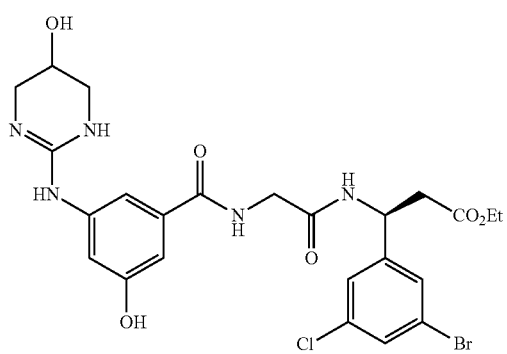

A mixture of 2-(3-hydroxy-5-((5-hydroxy-1,4,5,6-tetrahydropyrimidin-2-yl)amino)benzamido)acetic acid (Example B) (82.0 mg; 0.266 mmol), ethyl (3S)-3-amino-3-(3-bromo-5-chloro-phenyl)propanoate hydrochloride (synthesized as in the methods described above starting from 3-bromo-5-chloro benzaldehyde) (91.40 mg, 0.266 mmol) was dissolved in DMF (1.5 mL) and dichloromethane (1.5 mL) to give a cream-orange suspension. Solid 1-hydroxybenzotriazole hydrate (9.0 mg, 0.059 mmol) was added to above reaction mixture and the reaction mixture was stirred under nitrogen atmosphere for 10 min. N,N'-diisopropylcarbodiimide (60.0 µL, 0.387 mmol) was added and the reaction mixture was stirred at room temperature under nitrogen atmosphere overnight. The solvent was evaporated in-vacuo to give a dirty yellow-orange gummy residue of the product: (3S)-ethyl 3-(3-bromo-5-chloro-phenyl)-3-(2-(3-hydroxy-5-

((5-hydroxy-1,4,5,6-tetrahydropyrimidin-2-yl)benzamido)acetamido)propanoate. LC-MS analysis of the crude residue shows the desired product's mass: m/z 596 ($^{35Cl,79Br}$M+H), m/z 598 ($^{35Cl,81Br,37Cl,79Br}$M+H), m/z 600 ($^{37Cl,81Br}$M+H), m/z 618 ($^{35Cl,79Br}$M+Na), m/z 620 ($^{35Cl,81Br,37Cl,79Br}$M+Na) and m/z 622 ($^{37Cl,81Br}$M+Na), Calculated for $C_{24}H_{27}BrClN_5O_6$: 596.86. The crude residue was used as such for the saponification reaction in Step 2.

Step 2

Preparation of (3S)-3-[3-bromo-5-chloro-phenyl)-3-(2-(3-hydroxy-5-((5-hydroxy-1,4,5,6-tetrahydropyrimidin-2-yl)amino)benzamido)acetamido]propanoic acid

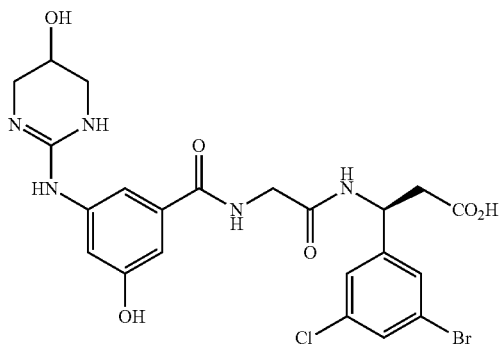

To a suspension of crude ethyl (3S)-3-(3-bromo-5-chlorophenyl)-3-(2-(3-hydroxy-5-((5-hydroxy-1,4,5,6-tetrahydropyrimidin-2-yl)amino)benzamido)acetamido)propanoate from step 1 above (0.266 mmol) in a mixture of a 1:1 mixture of acetonitrile/water (4 mL) was added lithium hydroxide monohydrate (56.0 mg, 0.1.334 mmol) at room temperature and the reaction mixture was stirred at room temperature for 4 h to give an orange-yellow solution. The mixture was neutralized with TFA (1 mL in 10.0 mL $CH_3CN$) and the mixture was evaporated in-vacuo to give a colorless gummy residue. The above crude product was purified by reverse-phase HPLC with a gradient 10-60% $CH_3CN$ in water containing 0.05% TFA to give the desired product, after lyophilization, as a colorless lyophilized solid (Example 6) (88.7 mg, yield 59%). LC/MS analysis of the product shows the desired product's mass: m/z 568 ($^{35Cl,79Br}$M+H), m/z 570 ($^{35Cl,81Br,37Cl,79Br}$M+H), and m/z 572 ($^{37Cl,81Br}$M+H); Calculated for $C_{22}H_{23}BrClN_5O_6$: 568.80. $^1$H NMR (400 MHz, DMSO-$d_6$): δ 2.74 (d, J=7.34 Hz, 2H, —$CH_2$—COOH), 3.16 (d, J=12.23 Hz, 2H), 3.34 (d, J=11.74 Hz, 2H), 3.87 (d, J=5.87 Hz, 2H), 4.08 (appt, 1H), 5.15 (q, J=7.42 Hz, 1H, —NH—CH—$CH_2$—COOH), 6.75 (t, J=1.96 Hz, 1H), 7.11 (s, 1H), 7.14 (s, 1H), 7.43 (s, 1H), 7.52 (s, 1H), 7.60 (s, 1H), 8.13 (brs, 1H), 8.84 (d, J=8.07 Hz, 1H), 8.64 (t, J=5.87 Hz, 1H), 9.65 (brs, 1H), 10.03 (brs, 1H), 12.45 (brs, 1H, —COOH). $^1$H NMR spectrum of the product was consistent with the proposed structure for Example 6.

Example 7

Preparation of (3S)-3-[3-chloro-5-(trifluoromethyl)phenyl]3-[[2-[[5-hydroxy-1,4,5,6-tetrahydropyrimidin-2-yl)amino]pyridine-3-carbonyl]amino]acetyl]amino]propanoic acid

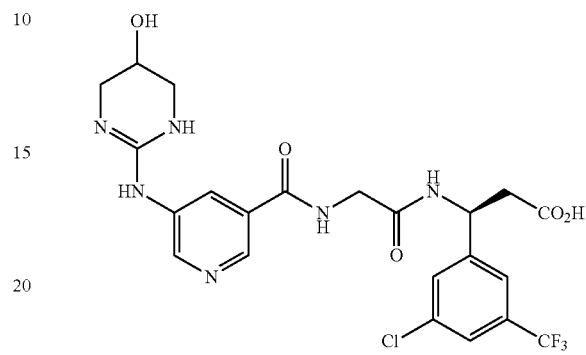

Step 1

Preparation of ethyl (3S)-3-[3-chloro-5-(trifluoromethyl)phenyl]-3-[[2-[[5-[(5-hydroxy-1,4,5,6-tetrahydropyrimidin-2-yl)amino]pyridine-3-carbonyl]amino]acetyl]amino]propanoate

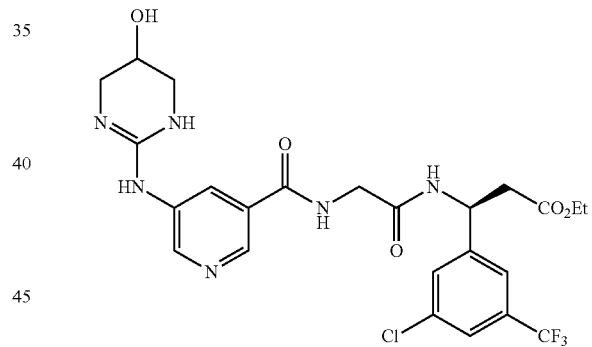

A mixture of 2-[[5-[(5-hydroxy-1,4,5,6-tetrahydropyrimidin-2-yl)amino]pyridine-3-carbonyl]amino]acetic acid (Example D) (56.0 mg, 0.115 mmol), ethyl (3S)-3-amino-3-[3-chloro-5-(trifluoromethyl)phenyl)propanoate hydrochloride (Example E) (38.05 mg, 0.115 mmol) and 1-hydroxybenzotriazole hydrate (3.5 mg, 0.023 mmol) was dissolved in DMF (3 mL) and dichloromethane (3 mL) and stirred at room temperature under nitrogen atmosphere for 10 min to give a cream suspension. N,N'-diisopropylcarbodiimide (25 μL, 0.161 mmol) was added and the reaction mixture was stirred at room temperature under nitrogen atmosphere overnight. The solvent was evaporated in-vacuo to give a colorless gummy solid of the intermediate product: ethyl (3S)-3-[3-chloro-5-(trifluoromethyl)phenyl]-3-[[2-[[5-[(5-hydroxy-1,4,5,6-tetrahydropyrimidin-2-yl)amino]pyridine-3-carbonyl]amino]acetyl]amino]propanoate. LC-MS analysis of the crude residue shows the desired product's mass: m/z 571 ($^{35Cl}$M+H), m/z 573 ($^{37Cl}$M+H); m/z 593 ($^{35Cl}$M+Na), and m/z 595 ($^{37Cl}$M+Na); Calculated for $C_{24}H_{26}ClF_3N_6O_5$: 570.95. The crude residue was used as such for the saponification reaction in Step 2.

Step 2

Preparation of (3S)-3-[3-chloro-5-(trifluoromethyl)phenyl]-3-[[2-[[5-[(5-hydroxy-1,4,5,6-tetrahydropyrimidin-2-yl)amino]pyridine-3-carbonyl]amino]acetyl]amino]propanoic acid

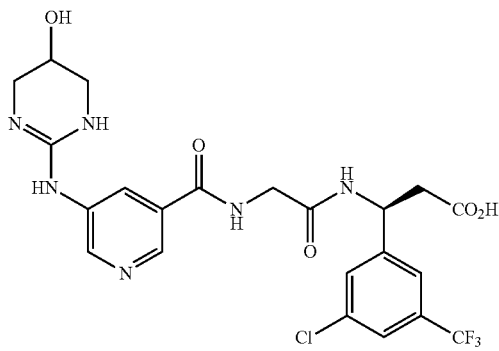

To a suspension of ethyl (3S)-3-[3-chloro-5-(trifluoromethyl)phenyl]-3-[[2-[[5-[(5-hydroxy-1,4,5,6-tetrahydropyrimidin-2-yl)amino]pyridine-3-carbonyl]amino]acetyl]amino]propanoate from step 1 above (0.115 mmol) in a mixture of a 1:1 mixture of acetonitrile/water (4 mL) was added lithium hydroxide monohydrate (25.0 mg, 0.596 mmol) and the reaction mixture was stirred at room temperature for 1 h. The reaction mixture was neutralized with TFA (250 µL in 5 mL CH$_3$CN) and the mixture was evaporated in-vacuo to give a colorless residue. The crude product was purified by reverse-phase HPLC with a gradient 10-70% CH$_3$CN in water containing 0.05% TFA to give the desired product, after lyophilization, as a colorless lyophilized solid (Example 7) (46.4 mg, yield 74%). LC/MS analysis of the product shows the desired product's mass: m/z 558 ($^{35Cl}$M+H), and m/z 560 ($^{37Cl}$M+H); Calculated for $C_{22}H_{22}ClF_3N_6O_5$: 542.90. $^1$H NMR (400 MHz, DMSO-d$_6$): δ 2.79 (d, J=7.34 Hz, 2H, —CH$_2$—COOH), 3.17 (d, J=11.98 Hz, 2H), 3.36 (d, J=11.98 Hz, 2H), 3.94 (d, J=5.87 Hz, 2H), 4.11 (brt, 1H), 5.25 (q, J=7.09 Hz, 1H, —NH—CH—CH$_2$—COOH), 7.70 (s, 1H), 7.75 (s, 2H), 8.02 (s, 1H), 8.43 (brs, 2H), 8.59 (brs, 1H), 8.66 (d, J=8.07 Hz, 1H), 8.90 (brs, 1H), 9.04 (t, J=5.75 Hz, 1H), 9.92 (s, 1H), 12.41 (brs, 1H, —COOH). $^1$H NMR spectrum of the product was consistent with the proposed structure for Example 7. $^{19}$F NMR (376 MHz, DMSO-d$_6$): δ −61.12 (s), and −74.31 (s).

Example 8

Preparation of (3S)-3-(3-bromo-5-chloro-phenyl)-3-[[2-[[5-[(5-hydroxy-1,4,5,6-tetrahydropyrimidin-2-yl)amino]pyridine-3-carbonyl]amino]acetyl]amino]propanoic acid

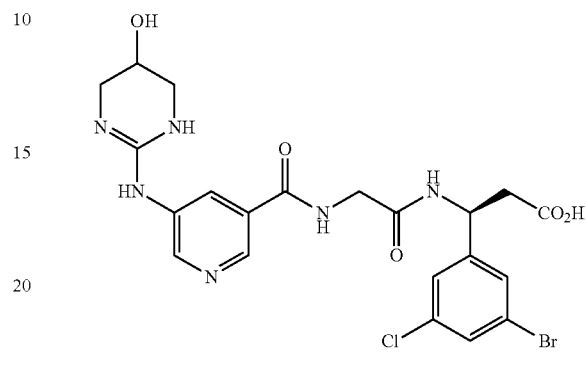

Step 1

Preparation of ethyl (3S)-3-(3-bromo-5-chloro-phenyl)-3-[[2-[[5[(5-hydroxy-1,4,5,6-tetrahydropyrimidin-2-yl)amino]pyridine-3-carbonyl]amino]acetyl]amino]propanoate

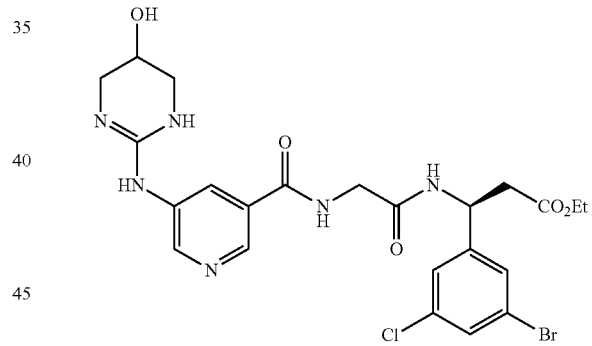

A mixture of 2-[[5-[(5-hydroxy-1,4,5,6-tetrahydropyrimidin-2-yl)amino]pyridine-3-carbonyl]amino]acetic acid (Example D) (80.0 mg, 0.164 mmol), ethyl (3S)-3-amino-3-[3-bromo-5-chlorophenyl)propanoate hydrochloride (synthesized as in the methods described above starting from 3-bromo-5-chloro benzaldehyde) (56.15 mg, 0.164 mmol) and 1-hydroxybenzotriazole hydrate (6.0 mg, 0.039 mmol) was dissolved in DMF (3 mL) and dichloromethane (3 mL) and stirred at room temperature under nitrogen atmosphere for 10 min to give a cream suspension. N,N'-diisopropylcarbodiimide (35.0 µL, 0.226 mmol) was added and the reaction mixture was stirred at room temperature under nitrogen atmosphere overnight. The solvent was evaporated in-vacuo to give a colorless solid of the intermediate product: ethyl (3S)-3-[3-bromo-5-chloro-phenyl]-3-[[2-[[5-[(5-hydroxy-1,4,5,6-tetrahydropyrimidin-2-yl)amino]pyridine- 3-carbonyl]amino]acetyl]amino]propanoate. LC-MS analysis of the crude residue shows the desired product's mass: m/z 581 ($^{35Cl,79Br}$M+H), m/z 583 ($^{35Cl,81Br,37Cl,79Br}$M+H), m/z 585 ($^{37Cl,81Br}$M+H), m/z 603 ($^{35Cl,79Br}$M+Na), m/z 605 ($^{35Cl,81Br,37Cl,79Br}$M+Na) and m/z 607 ($^{37Cl,81Br}$M+Na); Calculated for $C_{23}H_{26}BrClN_6O_5$: 581.85. The crude residue was used as such for the saponification reaction in Step 2.

Step 2

Preparation of (3S)-3-(3-bromo-5-chloro-phenyl)-3-[[2-[[5-[(5-hydroxy-1,4,5,6-tetrahydropyrimidin-2-yl)amino]pyridine-3-carbonyl]amino]acetyl]amino] propanoic acid

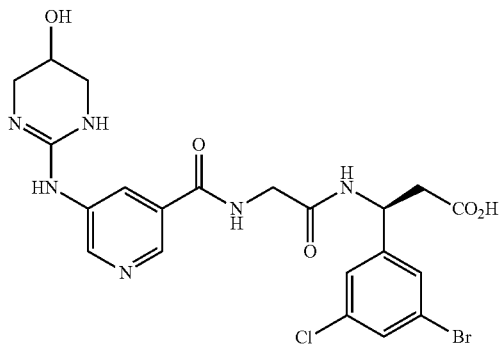 [SMILES: O=C(O)C[C@H](NC(=O)CNC(=O)c1cncc(NC2=NCC(O)CN2)c1)c1cc(Cl)cc(Br)c1]

To a suspension of ethyl (3S)-3-[3-bromo-5-chloro-phenyl]-3-[[2-[[5-[(5-hydroxy-1,4,5,6-tetrahydropyrimidin-2-yl)amino]pyridine-3-carbonyl]amino]acetyl] amino]acetyl] amino]propanoate from step 1 above (0.164 mmol) in a mixture of a 1:1 mixture of acetonitrile/water (6 mL) was added lithium hydroxide monohydrate (35.0 mg, 0.834 mmol) and the reaction mixture was stirred at room temperature for 2 h. The reaction mixture was neutralized with TFA (250 µL in 5 mL $CH_3CN$) and the mixture was evaporated in-vacuo to give a colorless crystalline solid. The crude product was purified by reverse-phase HPLC with a gradient 10-50% $CH_3CN$ in water containing 0.05% TFA to give the desired product, after lyophilization, as a colorless lyophilized solid (Example 8) (55.0 mg, yield 61%). LC/MS analysis of the product shows the desired product's mass: m/z 553 ($^{35Cl,79Br}$M+H), m/z 555 ($^{35Cl,81Br,37Cl,79Br}$M+H), and m/z 557 ($^{37Cl,81Br}$M+H); Calculated for $C_{21}H_{22}BrClN_6O_5$: 553.79. $^1$H NMR (400 Mhz, DMSO-$D_6$): δ 2.75 (d, J=7.34 Hz, 2H, —$CH_2$—COOH), 3.17 (d, J=12.23 Hz, 2H), 3.36 (d, J=11.00 Hz, 2H), 3.94 (d, J=5.62 Hz, 2H), 4.11 (t, J=3.20 Hz, 1H), 5.16 (q, J=7.42 Hz, 1H, —NH—CH—$CH_2$—COOH), 7.44 (t, J=1.47 Hz, 1H), 7.53 (apt, 1H), 7.60 (t, J=1.83 Hz, 1H), 8.03 (t, J=2.08 Hz, 1H), 8.42 (brs, 2H), 8.59 (d, J=7.82 Hz, 1H), 8.90 (brs, 1H), 9.03 (t, J=5.87 Hz, 1H), 9.90 (s, 1H), 12.42 (brs, 1H, —COOH). $^1$H NMR spectrum of the product was consistent with the proposed structure for Example 8.

Example 9

Preparation of (3S)-3-[3-bromo-5-(trifluoromethyl) phenyl]-3-[[2-[[5-[(5-hydroxy-1,4,5,6-tetrahydropyrimidin-2-yl)amino]pyridine-3-carbonyl]amino] acetyl]amino]propanoic acid

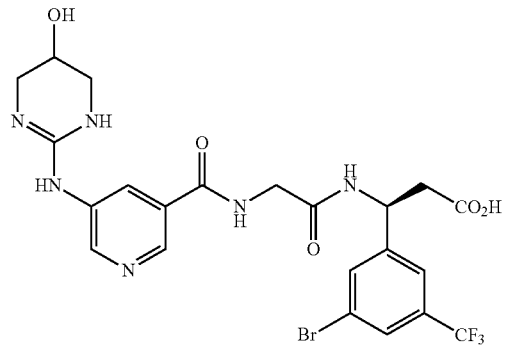 [SMILES: O=C(O)C[C@H](NC(=O)CNC(=O)c1cncc(NC2=NCC(O)CN2)c1)c1cc(Br)cc(C(F)(F)F)c1]

Step 1

Preparation of ethyl (3S)-3-[3-bromo-5-(trifluoromethyl)pheny]-3-[[2-[[5-[(5-hydroxy-1,4,5,6-tetrahydropyrimidin-2-yl)amino]pyridine-3-carbonyl] amino]acetyl]amino]propanoate

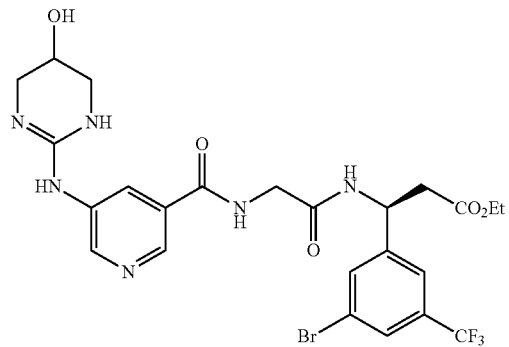 [SMILES: CCOC(=O)C[C@H](NC(=O)CNC(=O)c1cncc(NC2=NCC(O)CN2)c1)c1cc(Br)cc(C(F)(F)F)c1]

A mixture of 2-[[5-[(5-hydroxy-1,4,5,6-tetrahydropyrimidin-2-yl)amino]pyridine-3-carbonyl]amino]acetic acid (Example D) (64.0 mg, 0.131 mmol), ethyl (3S)-3-amino-3-(3-bromo-5-(trifluoromethyl)phenyl)propanoate hydrochloride (Example F) (49.31 mg, 0.131 mmol) and 1-hydroxybenzotriazole hydrate (5.0 mg, 0.033 mmol) was dissolved in DMF (3 mL) and dichloromethane (3 mL) and stirred at room temperature under nitrogen atmosphere for 10 min to give a cream suspension. N,N'-diisopropylcarbodiimide (30.0 µL, 0.194 mmol) was added and the reaction mixture was stirred at room temperature under nitrogen atmosphere overnight. The solvent was evaporated in-vacuo to give a colorless gummy solid of the intermediate product: ethyl (3S)-3-[3-bromo-5-(trifluoromethyl)phenyl]-3-[[2-[[5-[(5-hydroxy-1,4,5,6-tetrahydropyrimidin-2-yl)amino]pyridine-3-carbonyl]amino]acetyl]amino]propanoate. LC-MS analysis of the crude residue shows the desired product's mass: m/z 615 ($^{79Br}$M+H), m/z 617 ($^{81Br}$M+H) m/z 637 ($^{79Br}$M+Na) and m/z 639 ($^{81Br}$M+Na); Calculated for $C_{24}H_{26}BrF_3N_6O_5$: 615.40. The crude residue was used as such for the saponification reaction in Step 2.

Step 2

Preparation of (3S)-3-[3-bromo-5-(trifluoromethyl)pheny]-3-[[2-[[5-[(5-hydroxy-1,4,5,6-tetrahydropyrimidin-2-yl)amino]pyridine-3-carbonyl]amino]acetyl]amino]propanoic acid

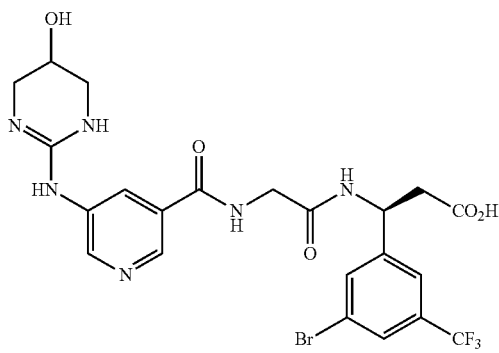

To a suspension of ethyl (3S)-3-[3-bromo-5-(trifluoromethyl)phenyl]-3-[[2-[[5-[(5-hydroxy-1,4,5,6-tetrahydropyrimidin-2-yl)amino]pyridine-3-carbonyl]amino]acetyl]amino]propanoate from step 1 above (0.131 mmol) in a mixture of a 1:1 mixture of acetonitrile/water (6 mL) was added lithium hydroxide monohydrate (30.0 mg, 0.715 mmol) and the reaction mixture was stirred at room temperature for 1 h. The reaction mixture was neutralized with TFA (250 µL in 5 mL CH$_3$CN) and the mixture was evaporated in-vacuo to give a colorless crystalline solid. The crude product was purified by reverse-phase HPLC with a gradient 10-60% CH$_3$CN in water containing 0.05% TFA to give the desired product, after lyophilization, as a colorless lyophilized solid (Example 9) (69.6 mg, yield 90%). LC/MS analysis of the product shows the desired product's mass: m/z 587 ($^{79Br}$M+H) m/z 609 ($^{79Br}$M+Na), and m/z 611 ($^{81Br}$M+Na); Calculated for $C_{22}H_{22}BrF_3N_6O_5$: 587.35. $^1$H NMR (400 MHz, DMSO-d$_6$): δ 2.79 (d, J=7.34 Hz, 2H, —CH$_2$—COOH), 3.17 (d, J=12.47 Hz, 2H), 3.36 (d, J=11.74 Hz, 2H), 3.94 (d, J=5.87 Hz, 2H), 4.11 (brt, 1H), 5.24 (q, J=7.25 Hz, 1H, —NH—CH—CH$_2$—COOH), 7.73 (s, 1H), 7.85 (s, 1H), 8.02 (t, J=2.08 Hz, 1H), 8.43 (brs, 2H), 8.59 (d, J=1.96 Hz, 1H), 8.66 (d, J=8.07 Hz, 1H), 8.90 (s, 1H), 9.05 (t, J=5.75 Hz, 1H), 9.92 (s, 1H), 12.43 (brs, 1H, —COOH). $^1$H NMR spectrum of the product was consistent with the proposed structure for Example 9. $^{19}$F NMR (376 MHz, DMSO-d$_6$): δ −61.10 (s), and −74.47 (s).

Example 10

Preparation of (3S)-3-[3,5-bis(trifluoromethyl)phenyl)-3-(2-(3-hydroxy-5-((5-hydroxy-1,4,5,6-tetrahydropyrimidin-2-yl)amino)benzamido)acetamido]propanoic acid

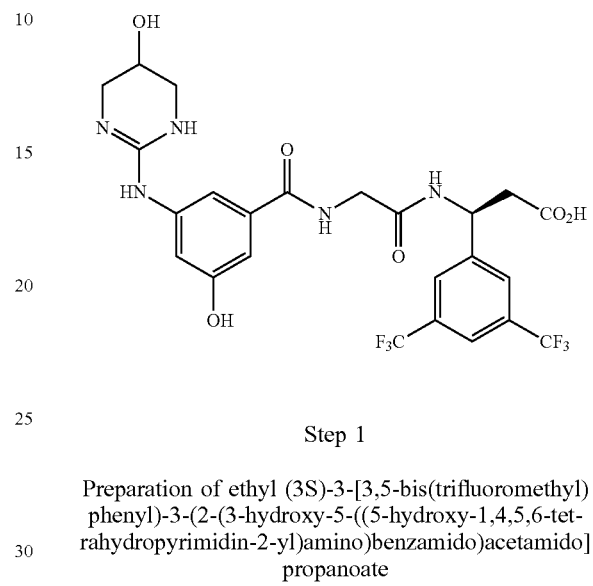

Step 1

Preparation of ethyl (3S)-3-[3,5-bis(trifluoromethyl)phenyl)-3-(2-(3-hydroxy-5-((5-hydroxy-1,4,5,6-tetrahydropyrimidin-2-yl)amino)benzamido)acetamido]propanoate

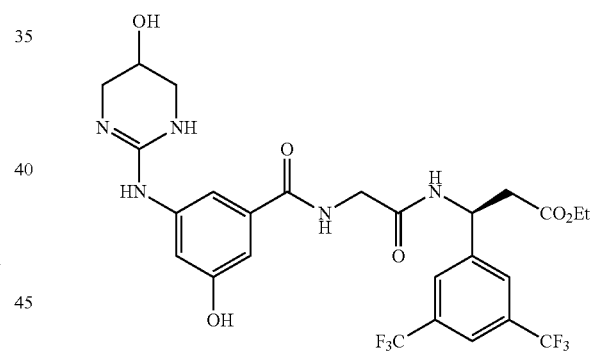

A mixture of 2-(3-hydroxy-5-((5-hydroxy-1,4,5,6-tetrahydropyrimidin-2-yl)amino)benzamido)acetic acid (Example B) (65.50 mg; 0.212 mmol), ethyl (3S)-3-amino-3-(3,5-bis(1-(trifluoromethyl)phenyl)propanoate hydrochloride (synthesized as in the methods described above starting from 3,5-bis trifluoromethyl benzaldehyde) (77.70 mg, 0.212 mmol) was dissolved in DMF (2 mL) and dichloromethane (2 mL) to give a colorless suspension. Solid 1-hydroxybenzotriazole hydrate (7.0 mg, 0.046 mmol) was added to above reaction mixture and the reaction mixture was stirred under nitrogen atmosphere for 10 min. N,N'-diisopropylcarbodiimide (45.0 µL 0.291 mmol) was added and the reaction mixture was stirred at room temperature under nitrogen atmosphere overnight. The solvent was evaporated in-vacuo to give a colorless gummy residue of the product: ethyl (3S)-3-(3,5-bis(trifluoromethyl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 620 (M+H), and m/z 642 (M+Na); Calculated for $C_{26}H_{27}F_6N_5O_6$: 619.51. The crude residue was used as such for the saponification reaction in Step 2.

Step 2

Preparation of (3S)-3-[3,5-bis(trifluoromethyl)phenyl)-3-(2-(3-hydroxy-5-((5-hydroxy-1,4,5,6-tetrahydropyrimidin-2-yl)amino)benzamido)acetamido]propanoic acid

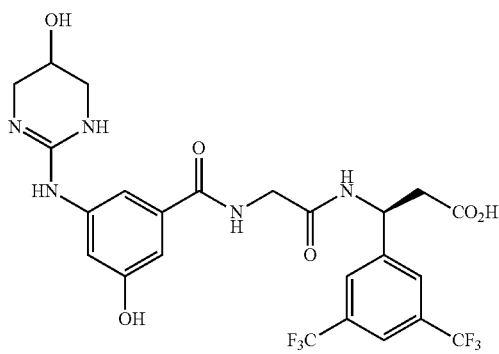

To a suspension of crude ethyl (3S)-3-(3,5-bis(trifluoromethyl)phenyl)-3-(2-(3-hydroxy-5-((5-hydroxy-1,4,5,6-tetrahydropyrimidin-2-yl)amino)benzamido)acetamido)propanoate from step 1 above (0.212 mmol) in a mixture of a 1:1 mixture of acetonitrile/water (6 mL) was added lithium hydroxide monohydrate (45.0 mg, 1.072 mmol) at room temperature and the reaction mixture was stirred at room temperature for 1 h. The mixture was neutralized with TFA (250 μL in 5.0 mL $CH_3CN$) and the mixture was evaporated in-vacuo to give a colorless gummy residue. The above crude product was purified by reverse-phase HPLC with a gradient 10-60% $CH_3CN$ in water containing 0.05% TFA to give the desired product, after lyophilization, as a colorless lyophilized solid (Example 10) (69.2 mg, yield 55%). LC/MS analysis of the product shows the desired product's mass: m/z 592 (M+H) and m/z 614 (M+Na), Calculated for $C_{24}H_{23}F_6N_5O_6$: 591.46. $^1$H NMR (400 MHz, DMSO-$d_6$): δ 2.83 (d, J=7.34 Hz, 2H, —$CH_2$—COOH), 3.15 (d, J=12.23 Hz, 2H), 3.33 (brd, J=10.67 Hz, 2H), 3.87 (d, J=5.62 Hz, 2H), 4.08 (d, J=3.18 Hz, 1H), 5.33 (q, J=7.09 Hz, 1H, —NH—CH—$CH_2$—COOH), 6.74 (t, J=2.08 Hz, 1H), 7.10 (appt, 1H), 7.13 (appt, 1H), 7.85-8.22 (m, 4H), 8.48-8.93 (m, 2H), 9.64 (s, 1H), 10.02 (brs, 1H), 12.45 (brs, 1H, —COOH). $^1$H NMR spectrum of the product was consistent with the proposed structure for Example 10. $^{19}$F NMR (376 MHz, DMSO-$d_6$): δ −61.14 (s), and −73.73 (s).

Example 11

Preparation of (3S)-3-[3-bromo-5-methyl-phenyl)-3-(2-(3-hydroxy-5-((5-hydroxy-1,4,5,6-tetrahydropyrimidin-2-yl)amino)benzamido)acetamido)propanoic acid

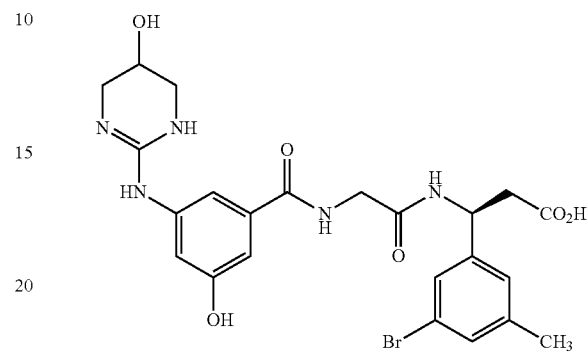

Step 1

Preparation of methyl (3S) 3-[3-bromo-5-methyl-phenyl)-3-(2-(3-hydroxy-5-((5-hydroxy-1,4,5,6-tetrahydropyrimidin-2-yl)amino)benzamido)acetamido]propanoate

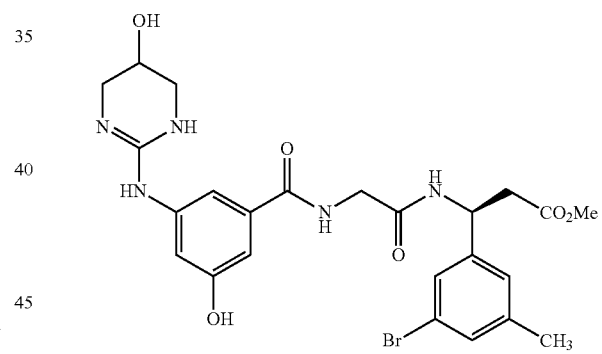

A mixture of 2-(3-hydroxy-5-((5-hydroxy-1,4,5,6-tetrahydropyrimidin-2-yl)amino)benzamido)acetic acid (Example B) (94.70 mg, 0.307 mmol), methyl (3S)-3-amino-3-(3-bromo-5-methyl-phenyl)propanoate hydrochloride (synthesized as in the methods described above starting from 3-bromo-5-methyl benzaldehyde) (94.80 mg, 0.307 mmol) was dissolved in DMF (2 mL) and dichloromethane (2 mL) to give a cream suspension. Solid 1-hydroxybenzotriazole hydrate (10.20 mg, 0.067 mmol) was added to above reaction mixture and the reaction mixture was stirred under nitrogen atmosphere for 10 min. N,N'-diisopropylcarbodiimide (70 μL, 0.452 mmol) was added and the reaction mixture was stirred at room temperature under nitrogen atmosphere overnight. The solvent was evaporated in-vacuo to give a colorless gummy residue of the product: methyl (3S)-3-[3-bromo-5-methyl-phenyl]-3-[[2-[[3-hydroxy-5-

[(5-hydroxy-1,4,5,6-tetrahydropyrimidin-2-yl)amino]benzoyl]amino]acetyl]amino]propanoate. LC-MS analysis of the crude residue shows the desired product's mass: m/z 562 ($^{79Br}$M+H), m/z 564 ($^{81Br}$M+H), m/z 584 ($^{79Br}$M+Na), and m/z 586 ($^{81Br}$M+Na), Calculated for $C_{24}H_{28}BrN_5O_6$: 562.41. The crude residue was used as such for the saponification reaction in Step 2.

Step 2

Preparation of (3S)-3-[3-bromo-5-methyl-phenyl)-3-(2-(3-hydroxy-5-((5-hydroxy-1,4,5,6-tetrahydropyrimidin-2-yl)amino)benzamido)acetamido)propanoic acid

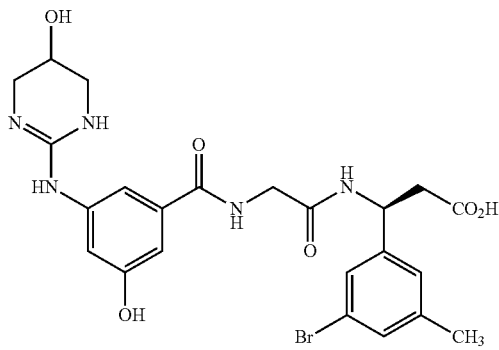 [SMILES: Cc1cc(Br)cc([C@H](CC(=O)O)NC(=O)CNC(=O)c2cc(O)cc(NC3=NCC(O)CN3)c2)c1]

To a solution of crude methyl (3S)-3-[3-bromo-5-methyl-phenyl]-3-[[2-[[3-hydroxy-5-[(5-hydroxy-1,4,5,6-tetrahydropyrimidin-2-yl)amino]benzoyl]amino]acetyl]amino]propanoate from step 1 above (0.307 mmol) in a mixture of a 1:1 mixture of acetonitrile/water (6 mL) was added lithium hydroxide monohydrate (65 mg, 1.55 mmol) at room temperature and the reaction mixture was stirred at room temperature for 1 h. The mixture was neutralized with TFA (500 µL in 5.0 mL $CH_3CN$) and the mixture was evaporated in-vacuo to give a colorless gummy residue. The above crude product was purified by reverse-phase HPLC with a gradient 10-50% $CH_3CN$ in water containing 0.05% TFA to give the desired product, after lyophilization, as a colorless lyophilized solid (Example 11) (105.3 mg, yield 62%). LC/MS analysis of the product shows the desired product's mass: m/z 548 ($^{79Br}$M+H), and m/z 550 ($^{81Br}$M+H); Calculated for $C_{23}H_{26}BrN_5O_6$: 548.39. $^1$H NMR (400 MHz, DMSO-$d_6$): δ 2.28 (s, 3H, $CH_3$—), 2.70 (d, J=7.34 Hz, 2H, —$CH_2$—COOH), 3.16 (d, J=12.23 Hz, 2H), 3.34 (d, J=11.98 Hz, 2H), 3.86 (d, J=5.87 Hz, 2H), 4.09 (t, J=2.90 Hz, 1H), 5.13 (q, J=7.50 Hz, 1H, —NH—CH—$CH_2$—COOH), 6.74 (t, J=1.96 Hz, 1H), 7.11 (s, 1H), 7.14 (appt, 1H), 7.28 (apt, 1H), 7.31 (apt, 1H), 8.13 (brs, 1H), 8.48 (d, J=8.31 Hz, 1H), 8.61 (t, J=5.87 Hz, 1H), 9.64 (s, 1H), 10.02 (brs, 1H), 12.37 (brs, 1H, —COOH). $^1$H NMR spectrum of the product was consistent with the proposed structure for Example 11.

Example 12

Preparation of (3S)-3-[3-chloro-5-methyl-phenyl)-3-(2-(3-hydroxy-5-((5-hydroxy-1,4,5,6-tetrahydropyrimidin-2-yl)amino)benzamido)acetamido)propanoic acid

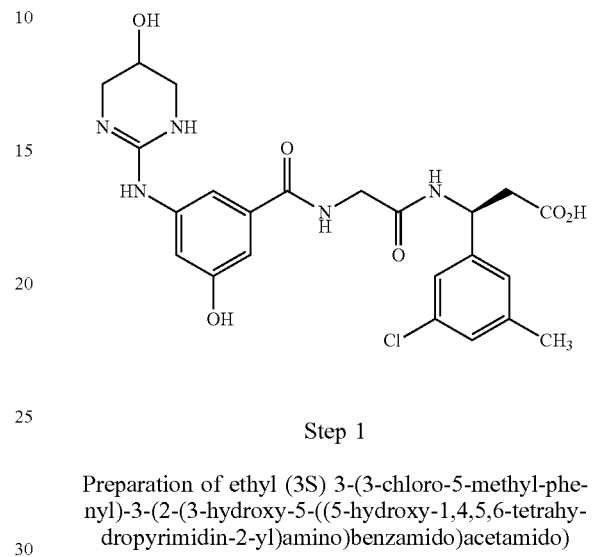

Step 1

Preparation of ethyl (3S) 3-(3-chloro-5-methyl-phenyl)-3-(2-(3-hydroxy-5-((5-hydroxy-1,4,5,6-tetrahydropyrimidin-2-yl)amino)benzamido)acetamido)propanoate

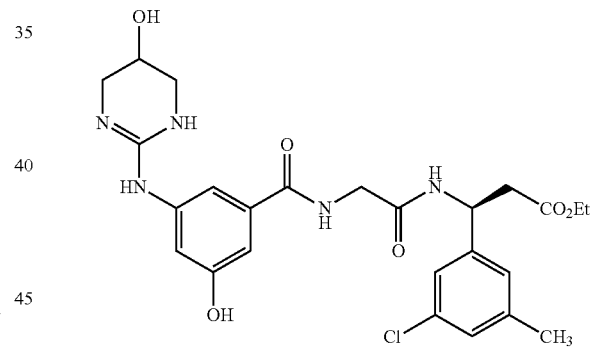

A mixture of 2-(3-hydroxy-5-((5-hydroxy-1,4,5,6-tetrahydropyrimidin-2-yl)amino)benzamido)acetic acid (Example B) (81.80 mg, 0.265 mmol), (S)-ethyl 3-amino-3-(3-chloro-5-methyl-phenyl)propanoate hydrochloride (synthesized as in the methods described above starting from 3-chloro-5-methyl benzaldehyde) (73.81 mg, 0.265 mmol) was dissolved in DMF (2 mL) and dichloromethane (2 mL) to give a cream suspension. Solid 1-hydroxybenzotriazole hydrate (8.4 mg, 0.055 mmol) was added to above reaction mixture and the reaction mixture was stirred under nitrogen atmosphere for 10 min. N,N'-diisopropylcarbodiimide (60 µL, 0.390 mmol) was added and the reaction mixture was stirred at room temperature under nitrogen atmosphere overnight. The solvent was evaporated in-vacuo to give a colorless gummy residue of the product: ethyl (3S)-3-[3-chloro-5-methyl-phenyl]-3-[[2-[[3-hydroxy-5-[(5-hydroxy-1,4,5,6- tetrahydropyrimidin-2-yl)amino]benzoyl]amino]acetyl]amino]propanoate. LC-MS analysis of the crude residue shows the desired product's mass: m/z 532 ($^{35Cl}$M+H), m/z 534 ($^{37Cl}$M+H), m/z 554 ($^{35Cl}$M+Na), and m/z 556 ($^{37Cl}$M+Na), Calculated for $C_{25}H_{30}ClN_5O_6$: 531.99. The crude residue was used as such for the saponification reaction in Step 2.

Step 2

Preparation of (3S)-3-[3-chloro-5-methyl-phenyl]-3-(2-(3-hydroxy-5-((5-hydroxy-1,4,5,6-tetrahydropyrimidin-2-yl)amino)benzamido)acetamido)propanoic acid

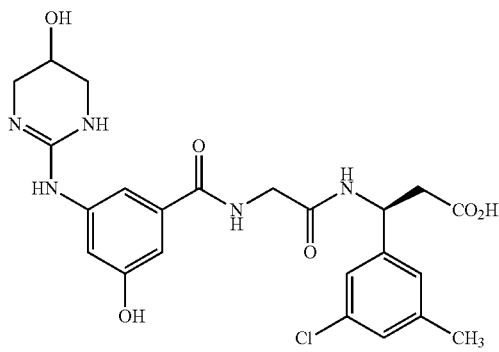

To a solution of crude ethyl (3S)-3-[3-chloro-5-methyl-phenyl]-3-[[2-[[3-hydroxy-5-[(5-hydroxy-1,4,5,6-tetrahydropyrimidin-2-yl)amino]benzoyl]amino]acetyl]amino]propanoate from step 1 above (0.265 mmol) in a mixture of a 1:1 mixture of acetonitrile/water (6 mL) was added lithium hydroxide monohydrate (56 mg, 1.334 mmol) at room temperature and the reaction mixture was stirred at room temperature for 1 h. The mixture was neutralized with TFA (500 µL in 5.0 mL CH$_3$CN) and the mixture was evaporated in-vacuo to give a colorless viscous residue. The above crude product was purified by reverse-phase HPLC with a gradient 10-50% CH$_3$CN in water containing 0.05% TFA to give the desired product, after lyophilization, as a colorless lyophilized solid (Example 12) (89.4 mg, yield 67%). LC/MS analysis of the product shows the desired product's mass: m/z 504 ($^{35Cl}$M+H), m/z 506 ($^{37Cl}$M+H), m/z 526 ($^{35Cl}$M+Na), and m/z 528 ($^{37Cl}$M+H); Calculated for $C_{23}H_{26}ClN_5O_6$: 503.94. $^1$H NMR (400 MHz, DMSO-d$_6$): δ 2.29 (s, 3H, CH$_3$—), 2.70 (d, J=7.34 Hz, 2H, —CH$_2$—COOH), 3.16 (d, J=11.98 Hz, 2H), 3.34 (d, J=11.00 Hz, 2H), 3.86 (d, J=5.87 Hz, 2H), 4.09 (appt/m, 1H), 5.14 (q, J=7.25 Hz, 1H, —NH—CH—CH$_2$—COOH), 6.74 (t, J=1.96 Hz, 1H), 7.11 (d, J=1.47 Hz, 2H), 7.14 (appt, 2H), 7.18 (s, 1H), 8.14 (br s, 2H), 8.48 (d, J=8.31 Hz, 1H), 8.61 (t, J=5.99 Hz, 1H), 9.67 (s, 1H), 10.03 (brs, 1H), 12.32 (brs, 1H, —COOH). $^1$H NMR spectrum of the product was consistent with the proposed structure for Example 12.

Example 13

Preparation of (3S)-3-[3-bromo-5-fluoro-phenyl]-3-(2-(3-hydroxy-5-((5-hydroxy-1,4,5,6-tetrahydropyrimidin-2-yl)amino)benzamido)acetamido)propanoic acid

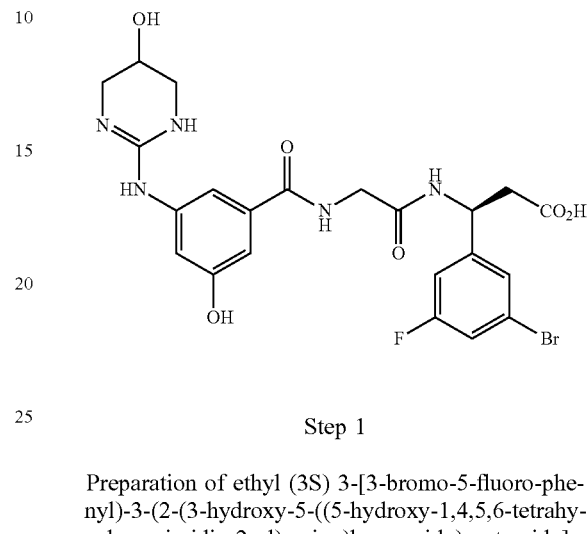

Step 1

Preparation of ethyl (3S) 3-[3-bromo-5-fluoro-phenyl]-3-(2-(3-hydroxy-5-((5-hydroxy-1,4,5,6-tetrahydropyrimidin-2-yl)amino)benzamido)acetamido]propanoate

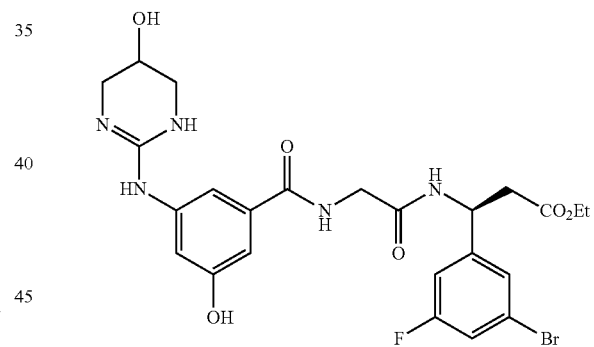

A mixture of 2-(3-hydroxy-5-((5-hydroxy-1,4,5,6-tetrahydropyrimidin-2-yl)amino)benzamido)acetic acid (Example B) (79.50 mg, 0.258 mmol), ethyl (3S)-3-amino-3-(3-bromo-5-fluoro-phenyl)propanoate hydrochloride (synthesized as in the methods described above starting from 3-bromo-5-fluoro benzaldehyde) (84.22 mg, 0.258 mmol) was dissolved in DMF (2 mL) and dichloromethane (2 mL) to give a cream suspension. Solid 1-hydroxybenzotriazole hydrate (8.0 mg, 0.052 mmol) was added to above reaction mixture and the reaction mixture was stirred under nitrogen atmosphere for 10 min. N,N'-diisopropylcarbodiimide (60 µL, 0.387 mmol) was added and the reaction mixture was stirred at room temperature under nitrogen atmosphere overnight. The solvent was evaporated in-vacuo to give a colorless gummy residue of the product: ethyl (3S)-3-[3-bromo-5-fluoro-phenyl]-3-[[2-[[3-hydroxy-5-[(5-hydroxy- 1,4,5,6-tetrahydropyrimidin-2-yl)amino]benzoyl]amino]acetyl]amino]propanoate. LC-MS analysis of the crude residue shows the desired product's mass: m/z 580 ($^{79Br}$M+H), m/z 582 ($^{81Br}$M+H), m/z 602 ($^{79Br}$M+Na), and m/z 604 ($^{81Br}$M+Na), Calculated for $C_{24}H_{27}BrFN_5O_6$: 580.40. The crude residue was used as such for the saponification reaction in Step 2.

Step 2

Preparation of (3S)-3-[3-bromo-5-fluoro-phenyl]-3-(2-(3-hydroxy-5-((5-hydroxy-1,4,5,6-tetrahydropyrimidin-2-yl)amino)benzamido)acetamido)propanoic acid

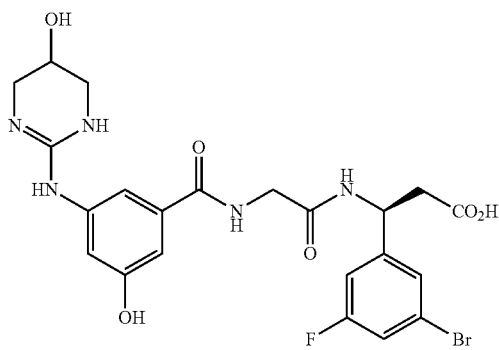

To a solution of crude ethyl (3S)-3-[3-bromo-5-fluoro-phenyl]-3-[[2-[[3-hydroxy-5-[(5-hydroxy-1,4,5,6-tetrahydropyrimidin-2-yl)amino]benzoyl]amino]acetyl]amino]propanoate from step 1 above (0.258 mmol) in a mixture of a 1:1 mixture of acetonitrile/water (6 mL) was added lithium hydroxide monohydrate (55 mg, 1.32 mmol) at room temperature and the reaction mixture was stirred at room temperature overnight. The mixture was neutralized with TFA (250 µL in 5.0 mL CH$_3$CN) and the mixture was evaporated in-vacuo to give a colorless gummy residue. The above crude product was purified by reverse-phase HPLC with a gradient 10-50% CH$_3$CN in water containing 0.05% TFA to give the desired product, after lyophilization, as a colorless lyophilized solid (Example 13) (110.3 mg, yield 77%). LC/MS analysis of the product shows the desired product's mass: m/z 552 ($^{79Br}$M+H), and m/z 554 ($^{81Br}$M+H); Calculated for $C_{22}H_{23}BrFN_5O_6$: 552.35. $^1$H NMR (400 MHz, DMSO-d$_6$): δ 2.74 (d, J=7.58 Hz, 2H, —CH$_2$—COOH), 3.16 (d, J=12.23 Hz, 2H), 3.34 (d, J=10.80 Hz, 2H), 3.87 (d, J=5.87 Hz, 2H), 4.08 (t, J=3.18 Hz, 1H), 5.17 (q, J=7.34 Hz, 1H, —NH—CH—CH$_2$—COOH), 6.75 (t, J=1.96 Hz, 1H), 7.11 (t, J=1.47 Hz, 1H), 7.14 (appt, 1H), 7.21 (t, J=1.71 Hz, 1H), 7.24 (appt, 1H), 7.41 (m, 2H), 8.13 (brs, 1H), 8.53 (d, J=8.07 Hz, 1H), 8.64 (t, J=5.75 Hz, 1H), 9.66 (brs, 1H), 10.03 (brs, 1H), 12.40 (brs, 1H, —COOH). $^1$H NMR spectrum of the product was consistent with the proposed structure for Example 13. $^{19}$F NMR (376 MHz, DMSO-d$_6$): δ −74.07 (s), and −110.57 (t, J=8.85 Hz).

Example 14

Preparation of (3S)-3-(3,5-dibromophenyl)-3-[[2-[[5-[(5-hydroxy-1,4,5,6-tetrahydropyrimidin-2-yl)amino]pyridine-3-carbonyl]amino]acetyl]amino]propanoic acid

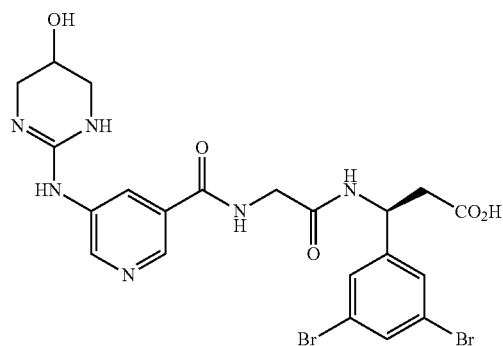

Step 1

Preparation of ethyl (3S)-3-(3,5-dibromophenyl)-3-[[2-[[5[(5-hydroxy-1,4,5,6-tetrahydropyrimidin-2-yl)amino]pyridine-3-carbonyl]amino]acetyl]amino]propanoate

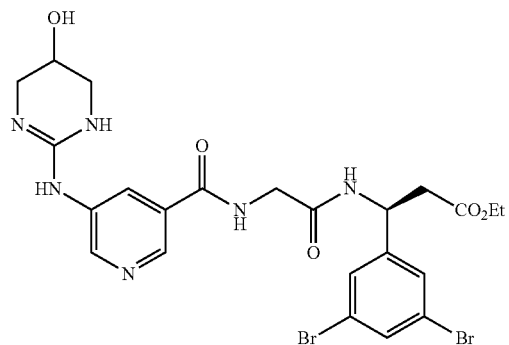 [SMILES: CCOC(=O)C[C@H](NC(=O)CNC(=O)c1cncc(NC2=NCC(O)CN2)c1)c1cc(Br)cc(Br)c1]

A mixture of 2-[[5-[(5-hydroxy-1,4,5,6-tetrahydropyrimidin-2-yl)amino]pyridine-3-carbonyl]amino]acetic acid (Example D) (78.0 mg, 0.266 mmol), ethyl (3S)-3-amino-3-(3,5-dibromophenyl)propanoate hydrochloride (the (S) ester of Example J formed via the enzymatic lipase cleavage method) (103.06 mg, 0.266 mmol) and 1-hydroxybenzotriazole hydrate (8.15 mg, 0.053 mmol) was dissolved in DMF (2 mL) and dichloromethane (2 mL) and stirred at room temperature under nitrogen atmosphere for 10 min to give a cream suspension. N,N'-diisopropylcarbodiimide (60.0 µL, 0.387 mmol) was added and the reaction mixture was stirred at room temperature under nitrogen atmosphere overnight. The solvent was evaporated in-vacuo to give a colorless crystalline solid of the intermediate product: ethyl (3S)-3-[3,5-dibromophenyl]-3-[[2-[[5-[(5-hydroxy-1,4,5,6-tetrahydropyrimi din-2-yl)amino]pyridine-3-carbonyl]amino]

acetyl]amino]propanoate. LC-MS analysis of the crude residue shows the desired product's mass: m/z 625 ($^{79Br,79Br}$M+H), m/z 627 ($^{79Br,81Br}$M+H), m/z 629 ($^{81Br,81Br}$M+$_H$) m/z 647 ($^{79Br,79Br}$M+Na), 649 ($^{79Br,81Br}$M+Na), and m/z 651 ($^{81Br,81Br}$M+Na); Calculated for $C_{23}H_{26}Br_2N_6O_5$: 626.30. The crude residue was used as such for the saponification reaction in Step 2.

Step 2

Preparation of (3S)-3-(3,5-dibromophenyl)-3-[[2-[[5-[(5-hydroxy-1,4,5,6-tetrahydropyrimidin-2-yl)amino]pyridine-3-carbonyl]amino]acetyl]amino]propanoic acid

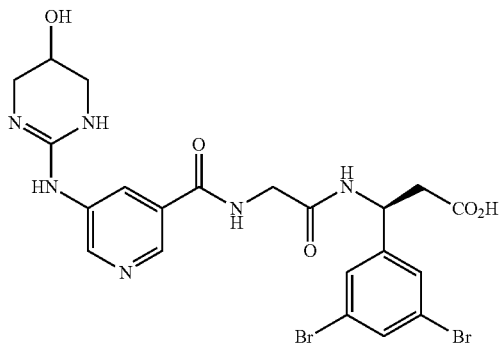

To a suspension of ethyl (3S)-3-[3,5-dibromophenyl]-3-[[2-[[5-[(5-hydroxy-1,4,5,6-tetrahydropyrimidin-2-yl)amino]pyridine-3-carbonyl]amino]acetyl]amino]propanoate from step 1 above (0.266 mmol) in a mixture of a 1:1 mixture of acetonitrile/water (6 mL) was added lithium hydroxide monohydrate (56.0 mg, 0.1.334 mmol) and the reaction mixture was stirred at room temperature for 1 h. The reaction mixture was neutralized with TFA (250 µL in 5 mL $CH_3CN$) and the mixture was evaporated in-vacuo to give a colorless crystalline/gummy solid. The crude product was purified by reverse-phase HPLC with a gradient 10-50% $CH_3CN$ in water containing 0.05% TFA to give the desired product, after lyophilization, as a colorless lyophilized solid (Example 14) (82.5 mg, yield 52%). LC/MS analysis of the product shows the desired product's mass: m/z 597 ($^{79Br,79Br}$M+H), m/z 599 ($^{79Br,81Br}$M+H), and m/z 601 ($^{81Br,81Br}$M+H); Calculated for $C_{21}H_{22}Br_2N_6O_5$: $^1$H NMR (400 MHz, DMSO-$d_6$): δ 2.74 (d, J=7.34 Hz, 2H, —$CH_2$—COOH), 3.17 (d, J=12.23 Hz, 2H), 3.36 (d, J=11.0 Hz, 2H), 3.93 (d, J=5.62 Hz, 2H), 4.11 (t, J=3.06 Hz, 1H), 5.15 (q, J=7.42 Hz, 1H, —NH—CH—$CH_2$—COOH), 7.57 (d, J=1.71 Hz, 1H), 7.72 (s, 1H), 8.03 (t, J=2.20 Hz, 1H), 8.42 (brs, 1H), 8.59 (m, 2H), 8.90 (d, J=1.71 Hz, 1H), 9.03 (t, J=5.75 Hz, 1H), 9.88 (s, 1H), 12.42 (brs, 1H, —COOH). $^1$H NMR spectrum of the product was consistent with the proposed structure for Example 14.

Example 15

Preparation of (3S)-3-[3,5-dichloro-phenyl]-3-(2-(3-hydroxy-5-((5-hydroxy-1,4,5,6-tetrahydropyrimidin-2-yl)amino)benzamido)acetamido)propanoic acid

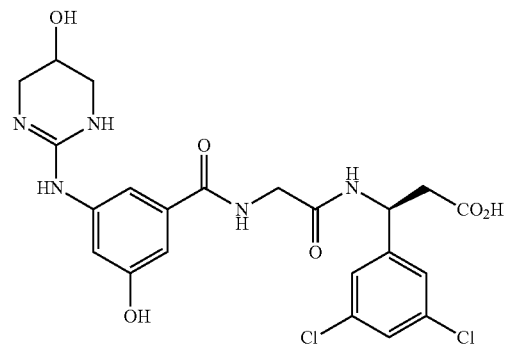 [SMILES: O=C(O)C[C@H](NC(=O)CNC(=O)c1cc(O)cc(NC2=NCC(O)CN2)c1)c1cc(Cl)cc(Cl)c1]

Step 1

Preparation of ethyl (3S) 3-(3,5-dichlorophenyl)-3-(2-(3-hydroxy-5-((5-hydroxy-1,4,5,6-tetrahydropyrimidin-2-yl)amino)benzamido)acetamido)propanoate

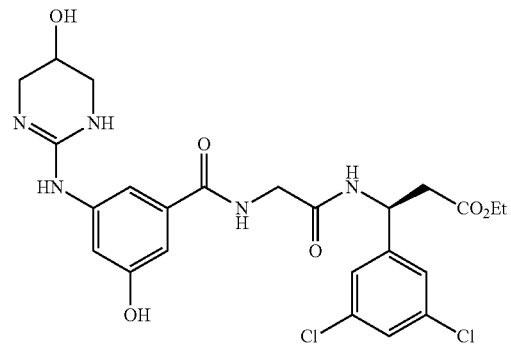

A mixture of 2-(3-hydroxy-5-((5-hydroxy-1,4,5,6-tetrahydropyrimi din-2-yl)amino)benzamido)acetic acid (Example B) (87.0 mg, 0.282 mmol), ethyl (3S)-3-amino-3-(3,5-dichlorophenyl)propanoate hydrochloride (Example I) (84.26 mg, 0.282 mmol) was dissolved in DMF (2 mL) and dichloromethane (2 mL) to give a cream suspension. Solid 1-hydroxybenzotriazole hydrate (9.0 mg, 0.059 mmol) was added to above reaction mixture and the reaction mixture was stirred under nitrogen atmosphere for 10 min. N,N'-diisopropylcarbodiimide (65 µL, 0.420 mmol) was added and the reaction mixture was stirred at room temperature under nitrogen atmosphere overnight. The solvent was evaporated in-vacuo to give a colorless gummy residue of the product: ethyl (3S)-3-[3,5-dichlorophenyl]-3-[[2-[[3-hydroxy-5-[(5-hydroxy-1,4,5,6-tetrahydropyrimidin-2-yl)amino]benzoyl]amino]acetyl]amino]propanoate. LC-MS analysis of the crude residue shows the desired product's mass: m/z 552 ($^{35Cl}$M+H), m/z 554 ($^{37Cl}$M+H), m/z 574 ($^{35Cl}$M+Na), and m/z 576 ($^{37Cl}$M+Na), Calculated for $C_{24}H_{27}Cl_2N_5O_6$: 552.41 The crude residue was used as such for the saponification reaction in Step 2.

Step 2

Preparation of (3S)-3-[3,5-dichloro-phenyl)-3-(2-(3-hydroxy-5-((5-hydroxy-1,4,5,6-tetrahydropyrimidin-2-yl)amino)benzamido)acetamido)propanoic acid

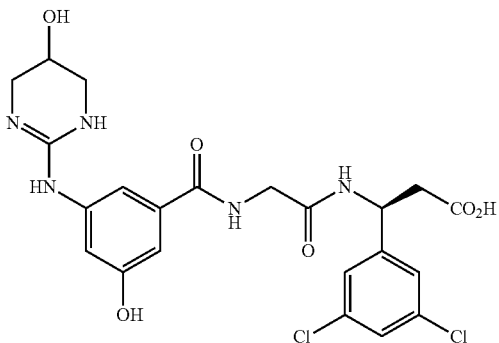 [SMILES: O=C(O)C[C@H](NC(=O)CNC(=O)c1cc(O)cc(NC2=NCC(O)CN2)c1)c1cc(Cl)cc(Cl)c1]

To a solution of crude ethyl (3S)-3-[3,5-chlorophenyl]-3-[[2-[[3-hydroxy-5-[(5-hydroxy-1,4,5,6-tetrahydropyrimidin-2-yl)amino]benzoyl]amino]acetyl]amino]propanoate from step 1 above (0.282 mmol) in a mixture of a 1:1 mixture of acetonitrile/water (6 mL) was added lithium hydroxide monohydrate (60 mg, 1.43 mmol) at room temperature and the reaction mixture was stirred at room temperature for 2 h. The mixture was neutralized with TFA (100 µL in 5.0 mL CH$_3$CN) and the mixture was evaporated in-vacuo to give a colorless viscous residue. The above crude product was purified by reverse-phase HPLC with a gradient 10-50% CH$_3$CN in water containing 0.05% TFA to give the desired product, after lyophilization, as a colorless lyophilized solid (Example 15) (101.2 mg, yield 68%). LC/MS analysis of the product shows the desired product's mass: m/z 524 ($^{35Cl}$M+H), and m/z 526 ($^{37Cl}$M+H); Calculated for $C_{22}H_{23}Cl_2N_5O_6$ 524.35. $^1$H NMR (400 MHz, DMSO-d$_6$): δ 2.75 (d, J=7.34 Hz, 2H, —CH$_2$—COOH), 3.16 (brd, J=11.98 Hz, 2H), 3.33 (brd, J=12.23 Hz, 2H), 3.87 (d, J=5.87 Hz, 2H), 4.08 (brs, 1H), 5.15 (q, J=7.17 Hz, 1H, —NH—CH—CH$_2$—COOH), 6.75 (t, J=2.08 Hz, 1H), 7.11 (appt, 1H), 7.14 (appt, 1H), 7.40 (d, J=1.96 Hz, 1H), 7.49 (appt, 1H), 8.12 (s, 2H), 8.54 (d, J=8.07 Hz, 1H), 8.64 (t, J=5.87 Hz, 1H), 9.64 (s, 1H), 10.02 (brs, 1H), 12.40 (brs, 1H, —COOH). $^1$H NMR spectrum of the product was consistent with the proposed structure for Example 15.

Example 16

Preparation of (3S)-3-[3-chloro-5-(trifluoromethoxy)phenyl)-3-(2-(3-hydroxy-5-((5-hydroxy-1,4,5,6-tetrahydropyrimidin-2-yl)amino)benzamido)acetamido)propanoic acid

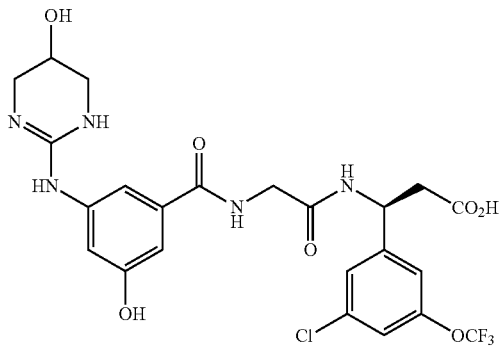 [SMILES: O=C(O)C[C@H](NC(=O)CNC(=O)c1cc(O)cc(NC2=NCC(O)CN2)c1)c1cc(Cl)cc(OC(F)(F)F)c1]

Step 1

Preparation of ethyl (3S) 3-(3-chloro-5-(trifluoromethoxy)phenyl)-3-(2-(3-hydroxy-5-((5-hydroxy-1,4,5,6-tetrahydropyrimidin-2-yl)amino)benzamido)acetamido)propanoate

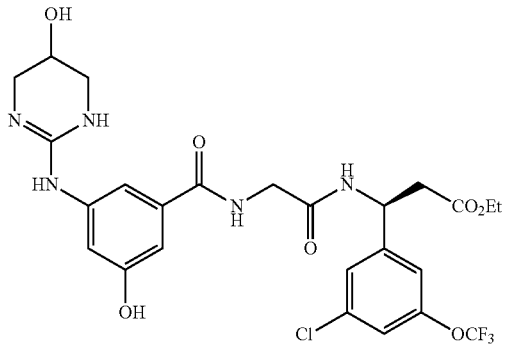 [SMILES: CCOC(=O)C[C@H](NC(=O)CNC(=O)c1cc(O)cc(NC2=NCC(O)CN2)c1)c1cc(Cl)cc(OC(F)(F)F)c1]

A mixture of 2-(3-hydroxy-5-((5-hydroxy-1,4,5,6-tetrahydropyrimidin-2-yl)amino)benzamido)acetic acid (Example B) (61.0 mg, 0.198 mmol), ethyl (3S)-3-amino-3-(3-chloro-5-(trifluoromethoxy)phenyl)propanoate hydrochloride (Example G) (68.89 mg, 0.198 mmol) was dissolved in DMF (2 mL) and dichloromethane (2 mL) to give a cream suspension. Solid 1-hydroxybenzotriazole hydrate (6.1 mg, 0.040 mmol) was added to above reaction mixture and the reaction mixture was stirred under nitrogen atmosphere for 10 min. N,N'-diisopropylcarbodiimide (46 µL, 0.297 mmol) was added and the reaction mixture was stirred at room temperature under nitrogen atmosphere overnight. The solvent was evaporated in-vacuo to give a cream gummy residue of the product: ethyl (3S)-3-[3-chloro-5-(trifluoromethoxy)phenyl]-3-[[2-[[3-hydroxy-5-[(5-hydroxy-1,4,5,6-tetrahydropyrimidin-2-yl)amino]benzoyl]

amino]acetyl]amino]propanoate. LC-MS analysis of the crude residue shows the desired product's mass: m/z 602 ($^{35Cl}$M+H), m/z 604 ($^{37Cl}$M+H), m/z 624 ($^{35Cl}$M+Na), and m/z 626 ($^{37Cl}$M+Na), Calculated for $C_{25}H_{27}ClF_3N_5O_7$: 601.96. The crude residue was used as such for the saponification reaction in Step 2.

Step 2

Preparation of (3S)-3-[3-chloro-5-(trifluoromethoxy)phenyl]-3-(2-(3-hydroxy-5-((5-hydroxy-1,4,5,6-tetrahydropyrimidin-2-yl)amino)benzamido)acetamido)propanoic acid

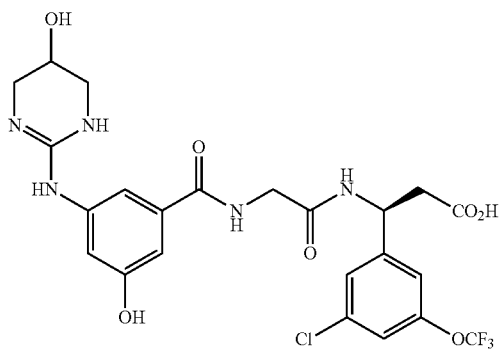

To a solution of crude ethyl (3S)-3-[3-chloro-5-(trifluoromethoxy)phenyl]-3-[[2-[[3-hydroxy-5-[(5-hydroxy-1,4,5,6-tetrahydropyrimidin-2-yl)amino]benzoyl]amino]acetyl]amino]propanoate from step 1 above (0.198 mmol) in a mixture of a 1:1 mixture of acetonitrile/water (6 mL) was added lithium hydroxide monohydrate (42 mg, 1.10 mmol) at room temperature and the reaction mixture was stirred at room temperature for 1 h. The mixture was neutralized with TFA (100 µL in 5.0 mL CH$_3$CN) and the mixture was evaporated in-vacuo to give a colorless viscous residue. The above crude product was purified by reverse-phase HPLC with a gradient 10-70% CH$_3$CN in water containing 0.05% TFA to give the desired product, after lyophilization, as a colorless lyophilized solid (Example 16) (69.50 mg, yield 61%). LC/MS analysis of the product shows the desired product's mass: m/z 574 ($^{35Cl}$M+H) m/z 576 ($^{37Cl}$M+H), m/z 596 ($^{35Cl}$M+Na), and m/z 598 ($^{37Cl}$M+Na), Calculated for $C_{23}H_{23}ClF_3N_5O_7$: 573.91. $^1$H NMR (400 MHz, DMSO-d$_6$): δ 2.76 (d, J=7.34 Hz, 2H, —CH$_2$—COOH), 3.17 (d, J=12.47 Hz, 2H), 3.34 (d, J=12.72 Hz, 2H), 3.88 (d, J=5.87 Hz, 2H), 4.09 (t, J=3.20 Hz, 1H), 5.21 (q, J=7.17 Hz, 1H, —NH—CH—CH$_2$—COOH), 6.76 (t, J=2.08 Hz, 1H), 7.12 (t, J=1.59 Hz, 1H), 7.14 (t, J=1.00 Hz, 1H), 7.35 (s, 1H), 7.45 (d, J=0.73 Hz, 1H), 7.49 (t, J=1.47 Hz, 1H), 8.13 (brs, 1H), 8.58 (d, J=7.82 Hz, 1H), 8.65 (t, J=5.87 Hz, 1H), 9.64 (s, 1H), 10.03 (brs, 1H), 12.44 (brs, 1H, —COOH). $^1$H NMR spectrum of the product was consistent with the proposed structure for Example 16. $^{19}$F NMR (376 MHz, DMSO-d$_6$): δ −56.83 (s), and −73.70 (s).

Example 17

Preparation of (3S)-3-(3-bromo-5-(trifluoromethoxy)phenyl)-3-(2-(3-hydroxy-5-((5-hydroxy-1,4,5,6-tetrahydropyrimidin-2-yl)amino)benzamido)acetamido)propanoic acid

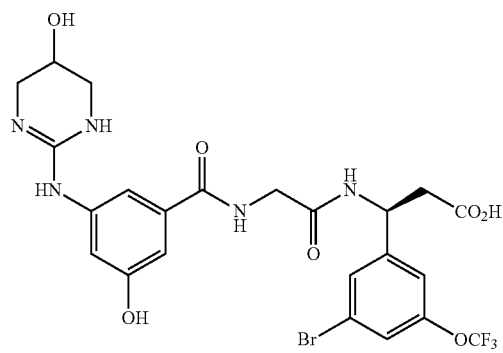 [SMILES: O=C(O)C[C@H](NC(=O)CNC(=O)c1cc(O)cc(NC2=NCC(O)CN2)c1)c1cc(Br)cc(OC(F)(F)F)c1]

Step 1

Preparation of ethyl (3S) 3-(3-bromo-5-(trifluoromethoxy)phenyl)-3-(2-(3-hydroxy-5-((5-hydroxy-1,4,5,6-tetrahydropyrimidin-2-yl)amino)benzamido)acetamido)propanoate

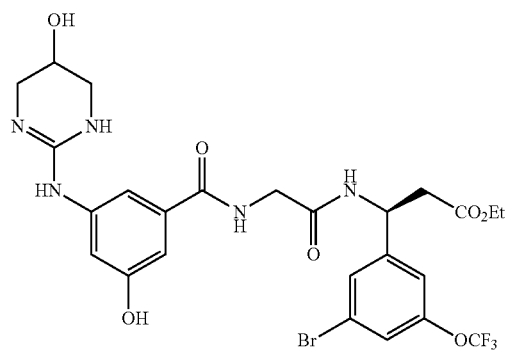

A mixture of 2-(3-hydroxy-5-((5-hydroxy-1,4,5,6-tetrahydropyrimidin-2-yl)amino)benzamido)acetic acid (Example B) (65.0 mg, 0.211 mmol), (S)-ethyl 3-amino-3-(3-bromo-5-(trifluoromethoxy)phenyl)propanoate hydrochloride (Example H) (82.75 mg, 0.211 mmol) was dissolved in DMF (2 mL) and dichloromethane (2 mL) to give a colorless suspension. Solid 1-hydroxybenzotriazole hydrate (7.0 mg, 0.046 mmol) was added to above reaction mixture and the reaction mixture was stirred under nitrogen atmosphere for 10 min. N,N'-diisopropylcarbodiimide (50 µL, 0.323 mmol) was added and the reaction mixture was stirred at room temperature under nitrogen atmosphere overnight. The solvent was evaporated in-vacuo to give a cream gummy residue of the product: ethyl (3S)-3-[3-bromo-5-(trifluoromethoxy)phenyl]-3-[[2-[[3-hydroxy-5-[(5-hydroxy-1,4,5,6-tetrahydropyrimidin-2-yl)amino]benzoyl]

amino]acetyl]amino]propanoate. LC-MS analysis of the crude residue shows the desired product's mass: m/z 646 ($^{79Br}$M+H), m/z 648 ($^{81Br}$M+H), m/z 668 ($^{79Br}$M+Na), and m/z 670 ($^{81Br}$M+Na), Calculated for $C_{25}H_{27}BrF_3N_5O_7$: 646.41. The crude residue was used as such for the saponification reaction in Step 2.

Step 2

Preparation of (3S)-3-(3-bromo-5-(trifluoromethoxy)phenyl)-3-(2-(3-hydroxy-5-((5-hydroxy-1,4,5,6-tetrahydropyrimidin-2-yl)amino)benzamido)acetamido)propanoic acid

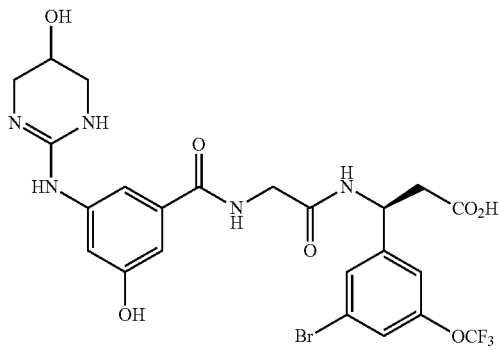 [SMILES: O=C(O)C[C@H](NC(=O)CNC(=O)c1cc(O)cc(NC2=NCC(O)CN2)c1)c1cc(Br)cc(OC(F)(F)F)c1]

To a solution of the crude product (0.211 mmol) from step 1 above in a mixture of a 1:1 mixture of acetonitrile/water (6 mL) was added lithium hydroxide monohydrate (48 mg, 1.144 mmol) at room temperature and the reaction mixture was stirred at room temperature for 1 h. The mixture was neutralized with TFA (0.1 mL in 5.0 mL $CH_3CN$) and the mixture was evaporated in-vacuo to give a colorless viscous residue. The above crude product was purified by reverse-phase HPLC with a gradient 10-70% $CH_3CN$ in water containing 0.05% TFA to give the desired product, after lyophilization, as a colorless lyophilized solid (Example 17) (83.2 mg, yield 64%). LC/MS analysis of the product shows the desired product's mass: m/z 618 ($^{79Br}$M+H), m/z 620 ($^{81Br}$M+H) m/z 640 ($^{79Br}$M+Na), and m/z 642 ($^{81Br}$M+Na), Calculated for $C_{23}H_{23}BrF_3N_5O_7$: 618.36. $^1$H NMR (400 MHz, DMSO-$d_6$): δ 2.75 (d, J=7.09 Hz, 2H, —$CH_2$—COOH), 3.16 (d, J=12.23 Hz, 2H), 3.33 (d, J=11.25 Hz, 2H), 3.87 (d, J=5.87 Hz, 2H), 4.08 (t, J=3.20 Hz, 1H), 5.19 (q, J=7.42 Hz, 1H, —NH—CH—$CH_2$—COOH), 6.75 (t, J=1.96 Hz, 1H), 7.11 (appt, 1H), 7.14 (t, J=1.70 Hz, 1H), 7.38 (s, 1H), 7.55 (s, 1H), 7.61 (s, 1H), 8.12 (brs, 1H), 8.58 (d, J=7.82 Hz, 1H), 8.64 (t, J=5.87 Hz, 1H), 9.63 (brs, 1H), 10.02 (brs, 1H), 12.42 (brs, 1H, —COOH). $^1$H NMR spectrum of the product was consistent with the proposed structure for Example 17. $^{19}$F NMR (376 MHz, DMSO-$d_6$): δ 56.81 (s), and −73.81 (s).

C. Biological Assay Results

The activities of the compounds of the present disclosure and comparison compounds were tested in the following assays and experimental studies. The results are presented in Tables 2, 3, and 4, and the FIGURE.

1. Solid Phase Receptor Assay (SPRA) for α5β1 Function

Purified human fibronectin (R&D Systems, 1918-FN) diluted to 2 µg/mL in TBS+ buffer (25 mM Tris pH 7.4, 137 mM NaCl, 2.7 mM KCl, 1 mM $CaCl_2$, 1 mM $MgCl_2$, 1 mM $MnCl_2$) was added to wells (50 µL/well) of a 96-well half-well transparent microtiter plate (Greiner 675061) and incubated overnight at 4° C. Wells were washed 3 times with 150 µL TBS+ and 150 µL of blocking buffer (TBS+ with 1% bovine serum albumin, Sigma A7906) were added. The plate was incubated for 1 hr at 37° C. and then washed 3× with TBS+ buffer. Recombinant human integrin α5β1 (R&D Systems, 3230-A5) was diluted to 0.1 µg/mL in TBS+/0.1% bovine serum albumin. Compounds were diluted 1:100 into the integrin solution and then 50 µL added to empty wells of the washed fibronectin-coated plate according to a standard template with each sample repeated in triplicate. After incubation for two hours at room temperature, the plate was washed 3× with 150 µL of TBS+ buffer. To each well, 50 µl of biotinylated anti-α5 antibody (R&D Systems, BAF1864) at 0.5 µg/mL in TBS+/0.1% BSA were added and the plate covered and incubated for 1 hr at room temperature. After washing the plate 3× with 150 µL of TBS+ buffer, 50 µL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 µL of room temperature TMB substrate (Sigma, T444) added to each well and the plate incubated for 20 min at room temperature. Plates were read by colorimetric detection at 650 nm wavelength using a Tecan Safire II plate reader. Concentration-response curves were constructed by non-linear regression (best fit) analysis, and $IC_{50}$ values were calculated for each compound.

2. Solid Phase Receptor Assay (SPRA) for αvβ1 Function

Purified human fibronectin (R&D Systems, 1918-FN) diluted to 5 µg/mL in TBS+ buffer (25 mM Tris pH 7.4, 137 mM NaCl, 2.7 mM KCl, 1 mM $CaCl_2$, 1 mM $MgCl_2$, 1 mM $MnCl_2$) was added to wells (50 µL/well) of a 96-well half-well transparent microtiter plate (Greiner 675061) and incubated overnight at 4° C. Wells were washed 3 times with 150 µL TBS+ and 150 µL of blocking buffer (TBS+ with 1% bovine serum albumin, Sigma A7906) were added. The plate was incubated for 1 hr at 37° C. and then washed 3× with TBS+ buffer. Recombinant human integrin αvβ1 (R&D Systems. 6579-AV) was diluted to 2.0 µg/mL in TBS+/0.1% bovine serum albumin. Compounds were diluted 1:100 into the integrin solution and 50 µL added to empty wells of the washed fibronectin-coated plate according to a standard template with each sample repeated in triplicate. After incubation for two hours at room temperature, the plate was washed 3× with 150 µL of TBS+ buffer. To each well, 50 µL of biotinylated anti-αv antibody (R&D Systems, BAF1219) at 1 µg/mL in TBS+/0.1% BSA were added and the plate covered and incubated for 1 hr at room temperature. After washing the plate 3× with 150 µL of TBS+ buffer, 50 µL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 µL of TMB substrate (Sigma, T4444) added to each well and the plate incubated for 20 min at room temperature. Plates were read by colorimetric detection at 650 nm wavelength using a Tecan Safire II plate reader. Concentration-response curves were constructed by non-linear regression (best fit) analysis, and $IC_{50}$ values were calculated for each compound.

3. Solid Phase Receptor Assay (SPRA) for αvβ3 Function

Recombinant human vitronectin (R& D Systems, 2308-VN) diluted to 1 µg/mL in TBS+ buffer (25 mM Tris pH 7.4, 137 mM NaCl, 2.7 mM KCl, 1 mM $CaCl_2$, 1 mM $MgCl_2$, 1 mM $MnCl_2$) was added to wells (50 µL/well) of a 96-well half-well transparent microtiter plate (Greiner 675061) and incubated overnight at 4° C. Wells were washed 3 times with 150 µL TBS+ and 150 µL of blocking buffer (TBS+ with 1% bovine serum albumin, Sigma A7906) were added. The plate was incubated for 1 hr at 37° C. and then washed 3× with TBS+ buffer. Recombinant human integrin αvβ3 (R&D Systems, 3050-AV) was diluted to 1 µg/mL in TBS+/0.1% bovine serum albumin. Compounds were diluted 1:100 into the integrin solution and then 50 µL added to empty wells of the washed vitronectin-coated plate according to a standard template with each sample repeated in triplicate. After incubation for two hours at room temperature, the plate was washed 3× with 150 µL of TBS+ buffer. To each well, 50 µL of biotinylated anti-αv antibody (R&D Systems, BAF1219) at 0.5 µg/mL in TBS+/0.1% BSA were added and the plate covered and incubated for 1 hr at room temperature. After washing the plate 3× with 150 µL of TBS+ buffer, 50 µL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 µL of TMB substrate (Sigma, T4444) added to each well and the plate was incubated for 20 min at room temperature. Plates were read by colorimetric detection at 650 nm wavelength using a Tecan Safire II plate reader. Concentration-response curves were constructed by non-linear regression (best fit) analysis, and $IC_{50}$ values were calculated for each compound.

4. Solid Phase Receptor Assay (SPRA) for αvβ5 Function

Recombinant human vitronectin (R&D Systems, 2308-VN) at 0.25 µg/mL in TBS+ buffer (25 mM Tris pH 7.4, 137 mM NaCl, 2.7 mM KCl, 1 mM $CaCl_2$, 1 mM $MgCl_2$, 1 mM $MnCl_2$) was added to wells (50 µL/well) of a 96-well half-well transparent microtiter plate (Greiner 675061) and incubated overnight at 4° C. Wells were washed 3 times with 150 µL TBS+ and 150 µL of blocking buffer (TBS+ with 1% bovine serum albumin, Sigma A7906) were added. The plate was incubated for 1 hr at 37° C. and then washed 3× with TBS+ buffer. Recombinant human integrin αvβ5 (R&D Systems, 2528-AV) was diluted to 0.1 µg/mL in TBS+/0.1% bovine serum albumin. Compounds were diluted 1:100 into the integrin solution and then 50 µL added to empty wells of the washed vitronectin-coated plate according to a standard template with each sample repeated in triplicate. After incubation for two hours at room temperature, the plate was washed 3× with 150 µL of TBS+ buffer. To each well, 50 µl of biotinylated anti-αv antibody (R&D Systems, BAF1219) at 0.5 µg/mL in TBS+/0.1% BSA at 0.5 µg/mL were added and the plate covered and incubated for 1 hr at room temperature. After washing the plate 3× with 150 µL of TBS+ buffer, 50 µL of streptavidin-conjugated horseradish peroxidase (R&D Systems DY998) diluted in TBS+ blocking buffer were added to the wells and the plate incubated for 20 min at room temperature. The plate was washed 3× with TBS+ buffer followed by 50 µL of TMB substrate (Sigma T4444) added to each well and the plate incubated for 20 min at room temperature. Plates were read by colorimetric detection at 650 nm wavelength using a Tecan Safire II plate reader. Concentration-response curves were constructed by non-linear regression (best fit) analysis, and $IC_{50}$ values were calculated for each compound.

5. Solid Phase Receptor Assay (SPRA) for αvβ6 Function

Recombinant human LAP (R&D Systems, 246-LP) diluted to 0.25 µg/mL in TBS+ buffer (25 mM Tris pH 7.4, 137 mM NaCl, 2.7 mM KCl, 1 mM $CaCl_2$, 1 mM $MgCl_2$, 1 mM $MnCl_2$) was added to wells (50 µL/well) of a 96-well half-well transparent microtiter plate (Greiner 675061) and incubated overnight at 4° C. Wells were washed 3 times with 150 µL TBS+, and 150 µL of blocking buffer (TBS+ with 1% bovine serum albumin, Sigma A7906) were added. The plate was incubated for 1 hr at 37° C., and then washed 3× with TBS+ buffer. Recombinant human integrin αvβ6 (R&D Systems, 3817-AV) was diluted to 0.1 µg/mL in TBS+/0.1% bovine serum albumin. Compounds were diluted 1:100 into the integrin solution and then 50 µL added to empty wells of the washed LAP-coated plate according to a standard template with each sample repeated in triplicate. After incubation for two hours at room temperature, the plate was washed 3× with 150 µL of TBS+ buffer. To each well, 50 µL of biotinylated anti-αv antibody (R&D Systems, BAF1219) at 0.5 µg/mL in TBS+/0.1% BSA were added and the plate was covered and incubated for 1 hr at room temperature. After washing the plate 3× with 150 µL of TBS+ buffer, 50 µL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 µL of TMB substrate (Sigma T4444) added to each well and the plate incubated for 20 min at room temperature. Plates were read by colorimetric detection at 650 nm wavelength using a Tecan Safire II plate reader. Concentration-response curves were constructed by non-linear regression (best fit) analysis, and $IC_{50}$ values were calculated for each compound.

6. Solid Phase Receptor Assay (SPRA) for αvβ8 Function

Recombinant human LAP protein (R&D Systems, Inc, 246-LP) diluted to 0.5 µg/mL in TBS+ buffer (25 mM Tris pH 7.4, 137 mM NaCl, 2.7 mM KCl, 1 mM $CaCl_2$, 1 mM $MgCl_2$, 1 mM $MnCl_2$) was added to wells (50 µl/well) of a 96-well half-well transparent microtiter plate (Greiner 675061), and incubated overnight at 4° C. Wells were washed 3 times with 150 µL TBS+ and 150 µL of blocking buffer (TBS+ with 1% bovine serum albumin, Sigma A7906) were added. The plate was incubated for 1 hr at 37° C. and then washed 3× with TBS+. Recombinant human integrin αvβ8 (R&D Systems, 4135-AV) was diluted to 0.1 µg/mL in TBS+/0.1% bovine serum albumin. Compounds were diluted 1:100 into the integrin solution and 50 µL added to empty wells of the washed LAP-coated plate according to a standard template with each sample repeated in triplicate. After incubation for two hours at room temperature, the plate was washed 3× with 150 µL of TBS+. To each well, 50 µL of biotinylated anti-αv antibody (R&D Systems, BAF1219) at 1 µg/mL in TBS+/0.1% BSA were added and the plate was covered and incubated for 1 hr at room temperature. After washing the plate 3× with 150 µL of TBS+ buffer, 50 µL of streptavidin-conjugated horseradish peroxidase (R&D Systems, DY998) diluted in TBS+ blocking buffer were added to the wells and the plate incubated for 20 min at room temperature. The plate was washed 3× with TBS+ followed by 50 µL of TMB substrate (Sigma T4444) added to each well and the plate incubated for 20 min at room temperature. Plates were read by colorimetric detection at 650 nm wavelength using a Tecan Safire II plate reader. Concentration-response curves were constructed by non-linear regression (best fit) analysis, and $IC_{50}$ values were calculated for each compound.

7. Solid Phase Receptor Assay (SPRA) for α8β1 Function

Recombinant mouse nephronectin protein (R&D Systems, Inc, 4298-NP) diluted to 1 µg/mL in TBS+ buffer (25 mM Tris pH 7.4, 137 mM NaCl, 2.7 mM KCl, 1 mM $CaCl_2$, 1 mM $MgCl_2$, 1 mM $MnCl_2$) was added to wells (50 µl/well) of a 96-well half-well transparent microtiter plate (Greiner 675061), and incubated overnight at 4° C. Wells were washed 3 times with 150 μL TBS+ and 150 μL of blocking buffer (TBS+ with 1% bovine serum albumin, Sigma A7906) were added. The plate was incubated for 1 hr at 37° C. and then washed 3× with TBS+. Recombinant human integrin α8β1 (R&D Systems, pre-launch) was diluted to 0.25 μg/mL in TBS+/0.1% bovine serum albumin. Compounds were diluted 1:100 into the integrin solution and 50 μL added to empty wells of the washed nephronectin-coated plate according to a standard template with each sample repeated in triplicate. After incubation for two hours at room temperature, the plate was washed 3× with 150 μL of TBS+. To each well, 50 μL of biotinylated anti-β antibody (R&D Systems, BAF1778) at 0.5 μg/mL in TBS+/0.1% BSA were added and the plate was covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ followed by 50 μL of TMB substrate (Sigma T4444) added to each well and the plate incubated for 20 min at room temperature. Plates were read by colorimetric detection at 650 nm wavelength using a Tecan Safire II plate reader. Concentration-response curves were constructed by non-linear regression (best fit) analysis, and $IC_{50}$ values were calculated for each compound.

D. Pharmacokinetic Analysis

1. Materials

A minimally sufficient volume of dimethylsulfoxide (DMSO) was added to each test compound to achieve solubilization. For intravenous (IV) delivery, compounds were then formulated as solutions in glycerol formal: saline (either 20:80 or 40:60 v/v) (Sigma Chemicals, St. Louis). For oral (PO) administration, compounds were formulated with 0.5% methylcellulose. Five to six compound solutions were combined into a singled mixed solution for IV and PO cassette administration with final DMSO concentrations <0.6% or <1.2%, for the IV and PO cassettes, respectively. Analytes were detected in test samples using an LC/MS/MS (liquid chromatography/mass spectrometry) system consisting of an LC-20AD pump (Shimadzu, Kyoto, Japan), an HTC PAL autosampler (Leap technologies, Carrboro, N.C.), and a Sciex API-4000 mass spectrometer in ESI mode (AB Sciex, Foster City, Calif.). An Amour $C_{18}$ reverse phase column (Analytical Sales and Services, Pompton Plains, N.J.) was used for chromatographic separation.

2. Experimental Protocols

Pharmacokinetic (PK) studies conducted at Saint Louis University used male Sprague-Dawley rats with an initial body weight of 200 to 220 g. IV PK studies were performed with the following compounds: Examples 1-3 and 5-17 and comparison compounds C12-C18, C29, and C30. Animals were allowed free access to food and water. Rats were individually housed and connected to jugular vein catheters. Each cassette formulation was administered intravenously to two rats (1 mL/kg body weight). Each cassette formulation contained 5-6 compounds at 1 mg/kg in either 20:80 or 40/60 glycerol formal/saline (v/v). Blood was collected manually via the catheter into lithium-heparin tubes at 0.017, 0.083, 0.5, 1, 2, 4, 6 and 24 hours post-dose. Animals were euthanized with $CO_2$ at the end of the experiment.

Oral PK studies were conducted with the following compounds: Examples 1-3 and 5-17 and comparison compounds C12, C14-16 and C29-30. The PO cassette formulations were administered via oral gavage to two rats (10 mL/kg body weight) containing 5-6 compounds per cassette. The oral dose was administered at 2 mg/kg/compound in 0.5% methylcellulose. Blood collection time points were 0.25, 0.5, 1, 2, 4, 6 and 24 hours post-dose into lithium-heparin tubes. Animals were euthanized with $CO_2$ at the end of the experiment.

Internal standard was added to all samples at 200 ng/mL (final), as well as 150 μL of acetonitrile. Plasma samples (50 μL total volume) were diluted with control nave rat plasma as appropriate to bring the sample measurement into the linear dynamic range of the standard curve. The samples were capped and mixed on a multi-plate vortexer for 5 minutes and centrifuged for 5 minutes at 3200 rmp. The supernant was transferred to 96-well sample plate and capped for LC/MS/MS analysis. Compounds were optimized and monitored for their respective MRM transitions. The mobile phases consisted of 0.1% formic acid (aqueous) and 100% acetonitrile (organic) with an Amour $C_{18}$ reverse phase column (2.1×30 mm, 5 micron) at a flow rate of 0.35 mL/min. The starting phase was 10% acetonitrile for the 0.9 minutes then increased to 90% acetonitrile over 0.4 minutes, and was maintained for an additional 0.2 minutes before returning to 10% acetonitrile over 0.4 minutes. The 10% acetonitrile was held for an additional 1.6 minutes. Peak areas were integrated using Analyst 1.5.1 (AB Sciex, Foster City, Calif.).

Similar rat PK studies were conducted by PRESCOS, LLC (San Diego, Calif.) for comparison compounds C19-C28. Female Sprague-Dawley rats with an initial body weight of 195 to 220 g were used. Cassette formulations with 1 mg/kg/compound in 40/60 glycerol formal/saline were administered intravenously to three rats. The dosing volume for each animal was 5 mL/kg body weight. Blood samples were collected via a jugular vein catheter at 0.017, 0.25, 0.5, 1, 2, 4 and 8 hours post-dose into K2EDTA tubes. Animals were euthanized with $CO_2$ at the end of the experiment. Sample processing and compound measurement by LC/MS/MS was performed by HT Laboratories (San Diego, Calif.).

TABLE 3A

Integrin Assay Results for Comparison Compounds

| Comparison Compounds | α5β1 SPRA $IC_{50}$ (nM) | α8β1 SPRA $IC_{50}$ (nM) | αvβ1 SPRA $IC_{50}$ (nM) | αvβ3 SPRA $IC_{50}$ (nM) | αvβ5 SPRA $IC_{50}$ (nM) | αvβ6 SPRA $IC_{50}$ (nM) | αvβ8 SPRA $IC_{50}$ (nM) |
|---|---|---|---|---|---|---|---|
| C1 | 16 ± 9 | 8 ± 2 | 17 ± 2 | 5 ± 2 | 3 ± 1 | 2 ± 1 | 3 ± 2 |
| C2 | 8 | 3 ± 0 | 5 | 3 | 0.4 | >1000 | 5 |
| C3 | 40 | 14 | 7 | 2 | 2 | 1 | 2 |
| C4 | 7 | 63 | 10 | 4 | 2 | 2 | 6 |
| C5 | 24 | 383 | 17 ± 5 | 4 | 1 | 17 ± 2 | 66 |
| C6 | 7 ± 4 | 17 | 8 ± 6 | 6 | 1 | 1 | 9 ± 6 |

TABLE 3A-continued

Integrin Assay Results for Comparison Compounds

| Comparison Compounds | α5β1 SPRA IC$_{50}$ (nM) | α8β1 SPRA IC$_{50}$ (nM) | αvβ1 SPRA IC$_{50}$ (nM) | αvβ3 SPRA IC$_{50}$ (nM) | αvβ5 SPRA IC$_{50}$ (nM) | αvβ6 SPRA IC$_{50}$ (nM) | αvβ8 SPRA IC$_{50}$ (nM) |
|---|---|---|---|---|---|---|---|
| C7  | 59     | 26  | 101    | 11    | 25  | 12 | 7     |
| C8  | 38     | 594 | 13     | 5     | 5   | 2  | 18    |
| C9  | 8 ± 3  | 40  | 5 ± 2  | 4 ± 1 | 0.4 | 1  | 6 ± 3 |
| C10 | 18     | 10  | 14 ± 8 | 6     | 2   | 3  | 5     |
| C11 | 33     | 17  | 16 ± 4 | 9     | 2   | 4  | 11    |

TABLE 3B

Integrin Assay Results for Examples

| Examples | α5β1 SPRA IC$_{50}$ (nM) | α8β1 SPRA IC$_{50}$ (nM) | αvβ1 SPRA IC$_{50}$ (nM) | αvβ3 SPRA IC$_{50}$ (nM) | αvβ5 SPRA IC$_{50}$ (nM) | αvβ6 SPRA IC$_{50}$ (nM) | αvβ8 SPRA IC$_{50}$ (nM) |
|---|---|---|---|---|---|---|---|
| 1  | 1 ± 0.5 | 1.3 | 2 ± 2 | 2.3 ± 0.1 | 0.2       | 0.4       | 0.3 ± 0.1 |
| 2  | 0.8     | 1.5 | 2     | 2.7 ± 0.4 | 0.4       | 0.3       | 0.5 ± 0.0 |
| 3  | 0.5     | 0.9 | 2     | 1         | 0.2       | 0.4       | 0.3       |
| 4  | 0.7     | 0.6 | 2     | 3         | 0.4       | 0.4       | 0.4       |
| 5  | 0.8     | 0.9 | 2     | 3         | 0.5       | 0.5       | 0.6       |
| 6  | 0.6     | 0.5 | 3     | 1         | 0.2       | 0.4       | 0.5       |
| 7  | 0.7     | 0.6 | 1     | 3         | 0.2 ± 0.0 | 0.3       | 0.4       |
| 8  | 0.6     | 0.6 | 1     | 4         | 0.1       | 0.4       | 0.4       |
| 9  | 0.3     | 0.5 | 1     | 3         | 0.3       | 0.3       | 0.3       |
| 10 | 1 ± 0.4 | 1.1 | 2 ± 1 | 4         | 1         | 0.3 ± 0.1 | 0.3 ± 0.1 |
| 11 | 0.5     | 0.7 | 0.4   | 2         | 0.3       | 0.5       | 0.6       |
| 12 | 2       | 0.8 | 4 ± 2 | 4         | 0.4       | 0.6       | 0.7 ± 0.1 |
| 13 | 0.6     | 0.6 | 1     | 1.7 ± 0.0 | 0.1       | 0.4       | 1.0 ± 0.3 |
| 14 | 0.6     | 0.4 | 0.7   | 0.3       | 0.1       | 0.2       | 0.2       |
| 15 | 1 ± 0.3 | 1.2 | 4 ± 1 | 4         | 0.3       | 0.6       | 1.1 ± 0.3 |
| 16 | 1 ± 0.4 | 0.5 | 3 ± 2 | 3 ± 0.3   | 0.6       | 0.5       | 0.3 ± 0.1 |
| 17 | 1 ± 0.1 | 0.7 | 4 ± 2 | 2.8 ± 1.1 | 0.6       | 0.7       | 0.3 ± 0.1 |

TABLE 4A

Plasma Half Life of Examples

| Examples | plasma t½ after 1 mg/kg IV bolus dose in rat |
|---|---|
| 1  | 20.2 hrs    |
| 2  | 9.1 hrs     |
| 3  | 6.1 hrs     |
| 4  | Not Tested  |
| 5  | 6.6 hrs     |
| 6  | 16.7 hrs    |
| 7  | 4.6 hrs     |
| 8  | 23.9 hrs    |
| 9  | 5.6 hrs     |
| 10 | 3.9 hrs     |
| 11 | 24.0 hrs    |
| 12 | 13.7 hrs    |
| 13 | 11.0 hrs    |
| 14 | 34.2 hrs    |
| 15 | 23.8 hrs    |
| 16 | 3.2 hrs     |
| 17 | 4.1 hrs     |

TABLE 4B

Plasma Half Life of Comparison Compounds

| Comparison Compounds | plasma t½ after 1 mg/kg iv bolus dose in rat |
|---|---|
| C12 | 0.5 hrs   |
| C13 | 1.1 hrs   |
| C14 | 1.0 hrs   |
| C15 | 0.6 hrs   |
| C16 | 1.6 hrs   |
| C17 | 0.8 hrs   |
| C18 | 1.2 hrs   |
| C19 | 0.43 hrs  |
| C20 | 0.38 hrs  |
| C21 | 1.5 hrs   |
| C22 | 0.30 hrs  |
| C23 | 0.21 hrs  |
| C24 | 0.28 hrs  |
| C25 | 0.23 hrs  |
| C26 | 0.25 hrs  |
| C27 | 0.21 hrs  |
| C28 | 0.3 hrs   |
| C29 | <.08 hrs  |
| C30 | 1.6 hrs   |

TABLE 5A

AUC Plasma Exposure of Compounds

| Example | AUC (0-inf) (ng × hr/mL) after a 2 mg/kg PO dose in rat |
|---|---|
| 1 | 25048 |
| 2 | 19257 |
| 3 | 4870 |
| 4 | Not Tested |
| 5 | 11402 |
| 6 | 34386 |
| 7 | 3887 |
| 8 | 4468 |
| 9 | 4121 |
| 10 | 12969 |
| 11 | 9136 |
| 12 | 9107 |
| 13 | 13929 |
| 14 | 6502 |
| 15 | 15610 |
| 16 | 6808 |
| 17 | 13128 |

TABLE 5B

AUC Plasma Exposure of Comparison Compounds

| Comparison Compound | AUC (0-inf) (ng × hr/mL) after a 2 mg/kg PO dose in rat |
|---|---|
| C12 | 205 |
| C14 | 224 |
| C15 | 87 |
| C16 | 62 |
| C29 | <1 |
| C30 | <1 |

The AUC of the examples described herein and select comparison compounds was determined after a single 2 mg/kg oral (PO) dose in rat, demonstrating improved plasma exposure of the examples of the present disclosure.

All of the compounds, compositions, and methods disclosed and claimed herein can be made and executed without undue experimentation in light of the present disclosure. While the compounds, compositions, and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references to the extent that they provide exemplary procedural or other details supplementary to those set forth herein, are specifically incorporated herein by reference.

U.S. Pat. No. 6,013,651
U.S. Pat. No. 6,028,223
Adachi et al., *Clin. Cancer Res.*, 6(1):96-101, 2000.
Asano et al., *J. Immunol.*, 175(11):7708-7718, 2005
Avraamides et al., *Nat. Rev. Cancer,* 8(8):604-617, 2008.
Bax et al., *J. Biol. Chem.*, 278(36):34605-34616, 2003.
Becker et al., *Tetrahedron,* 39:4189-4192, 1983.
Bhaskar et al., *J. Transl. Med.*, 5:61, 2007.
Blase et al., *Int. J. Cancer,* 60(6):860-866, 1995.
Bouzeghrane, et al., *J. Mol. Cell. Cardiology,* 36:343-353, 2004.
Clark, et al., *Organic Process Research & Development,* 8:51-61, 2004.
Clark, et al., *Organic Process Research & Development,* 8:571-575, 2004.
Collo, *J. Cell Sci.,* 112(Pt 4):569-578, 1999.
Danen et al., *Histopathology,* 24(3):249-256, 1994.
Edward, *Curr. Opin. Oncol.,* 7(2):185-191, 1995.
Engleman et al., *J. Clin. Invest.,* 99(9):2284-2292, 1997.
Faulconbridge et al., *Tetrahedron Lett.,* 41:2679-2681, 2000.
Ferrari et al., *Proc. Natl. Acad. Sci. USA,* 103(46):17260-17265, 2006.
Gao and Brigstock, *Gut,* 55:856-862, 2006.
Girsch et al., *J. Med. Chem.,* 50:1658-1667, 2007.
Girsch et al., *J. Med. Chem.,* 51:6752-6760, 2008.
Greene & Wuts, *Protective Groups in Organic Synthesis,* $3^{rd}$ Ed., John Wiley, 1999.
*Handbook of Pharmaceutical Salts: Properties, and Use,* Stahl and Wermuth (Eds.), Verlag Helvetica Chimica Acta, 2002.
Henderson, et al., *Nat. Med.,* 19:1617-1624, 2013.
Herlt, et al., *Austr. J. Chem.,* 34(6):1319-1324, 1981.
Horan et al., *Am. J. Respir. Crit. Care Med.,* 177(1):56-65, 2008.
Jorgensen, et al., *J. Am. Chem. Soc.,* 124(42):12557-12565, 2002.
Kim et al., *Am. J. Pathol.,* 156(4):1345-1362, 2000.
Landis et al., *Organic Process Research & Development,* 6:539-546, 2002.
Levine, et al., *Am. J. Pathol.,* 156:1927-1935, 2000.
Li et al., *Invest. Ophthalmol. Vis. Sci.,* 50(12):5988-5996, 2009.
Livant et al., *J. Clin. Invest.,* 105(11):1537-1545, 2000.
Lobert et al., *Dev. Cell,* 19(1):148-159, 2010.
Lu, et al., *J. Cell Sci.,* 115:4641-4648, 2002.
*March's Advanced Organic Chemistry: Reactions, Mechanisms, and Structure,* 2007.
Melton et al., *J. Clin. Invest.,* 120(12):4436-4444, 2010.
Millard et al., *Theranostics,* 1:154-88, 2011.
Mu et al., *Cell Biol.,* 157(3):493-507, 2002.
Munger et al., *Cell.,* 96(3):319-328, 1999.
Munger et al., *Mol. Biol. Cell,* 9:2627-2638, 1998.
Nishimura, *Am. J. Pathol.,* 175(4):1362-1370, 2009.
Perdih, *Curr. Med. Chem.,* 17(22):2371-2392, 2010.
Popov et al., *J. Hepatol.,* 48(3):453-464, 2008.
Reagan-Shaw et al., *FASEB J.,* 22(3):659-661, 2008
Scotton et al., *J. Clin. Invest.,* 119(9):2550-2563, 2009.
Suehiro et al., *J. Biochem.,* 128(4):705-710, 2000.
Sun, et al., *Am. J. Therapeutics,* 2014.
Wipff et al., *J. Cell Biol.,* 179(6):1311-1323, 2007.
Yang et al., *Development,* 119(4):1093-1105, 1993.
Yoshimura, *Curr. Top. Microbiol. Immunol.,* 350:127-147, 2011.
Zahn et al., *Arch. Ophthalmol.,* 127(10):1329-1335, 2009.
Zahn et al., *Invest. Ophthalmol. Vis. Sci.,* 51(2):1028-1035, 2010

What is claimed is:

1. A compound of the formula:

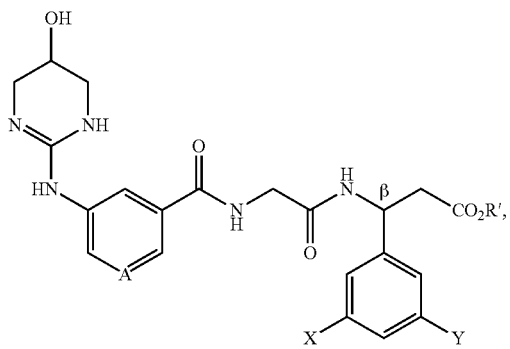

wherein:
A is CH, COH, or N;
R' is hydrogen, alkyl$_{(C\leq8)}$, substituted alkyl$_{(C\leq8)}$; and
X and Y are each independently cyano, halo, fluoroalkoxy$_{(C1-2)}$, alkyl$_{(C1-2)}$, or fluoroalkyl$_{(C1-2)}$, with the proviso that X and Y are not both cyano or alkyl$_{(C1-2)}$;
or a pharmaceutically acceptable salt or tautomer of the above formula.

2. The compound of claim 1, wherein the carbon atom labeled β is in the S configuration.

3. The compound of claim 2 further defined as:

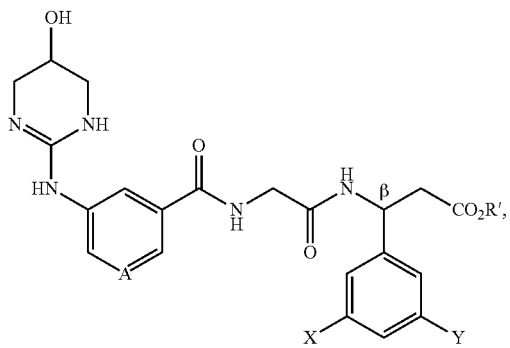

wherein:
A is C—OH or N;
R' is hydrogen, alkyl$_{(C\leq8)}$, substituted alkyl$_{(C\leq8)}$; and
X and Y are each independently cyano, halo, fluoroalkoxy$_{(C1-2)}$, alkyl$_{(C1-2)}$, or fluoroalkyl$_{(C1-2)}$, with the proviso that X and Y are not both cyano or alkyl$_{(C1-2)}$;
or a pharmaceutically acceptable salt or tautomer of the above formula.

4. The compound of claim 2, wherein A is N.
5. The compound of claim 2, wherein A is C—OH.
6. The compound of claim 2, wherein R' is hydrogen.
7. The compound of claim 2, wherein X is halo.
8. The compound of claim 7, wherein X is —F, —Cl, or —Br.
9. The compound of claim 8, wherein X is —Br or —Cl.
10. The compound claim 2, wherein Y is fluoroalkoxy$_{(C1-2)}$.
11. The compound of claim 10, wherein Y is —OCF$_3$.
12. The compound of claim 2, wherein Y is fluoroalkyl$_{(C1-2)}$.
13. The compound of claim 9, wherein Y is —CHF$_2$ or —CF$_3$.
14. The compound of claim 9, wherein Y is fluoroalkoxy$_{(C1-2)}$.
15. The compound of claim 14, wherein Y is —OCF$_3$.
16. The compound of claim 2, wherein Y is alkyl$_{(C1-2)}$.
17. The compound of claim 16, wherein Y is —CH$_3$.
18. The compound of claim 1, further defined as:

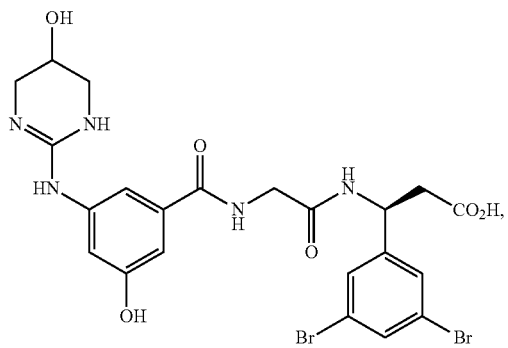

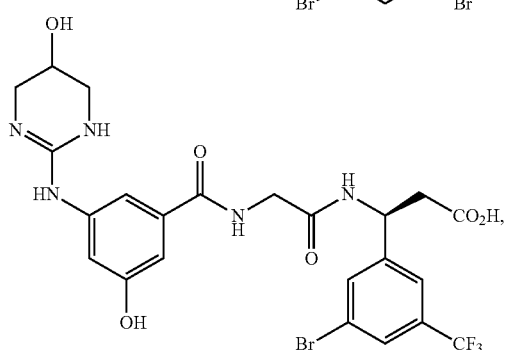

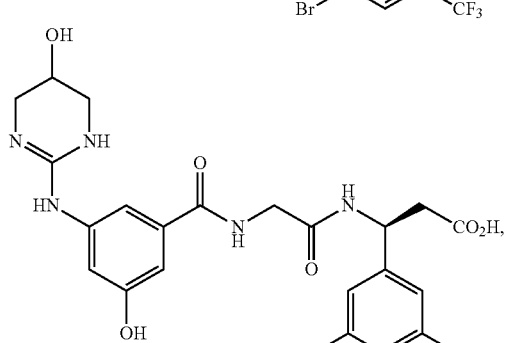

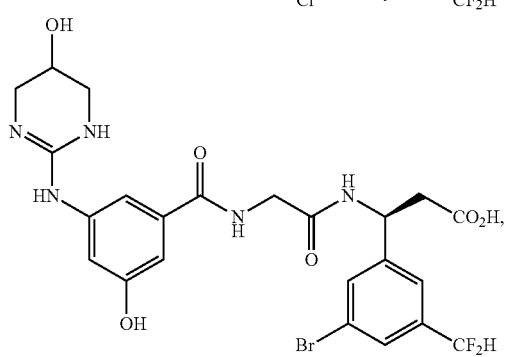

-continued
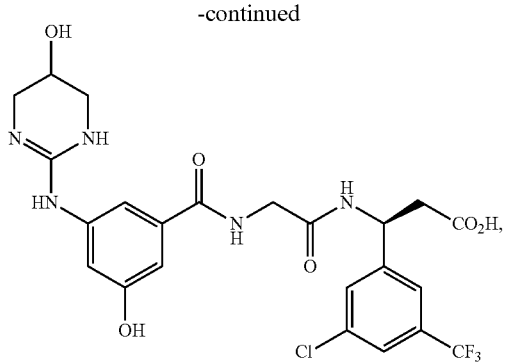
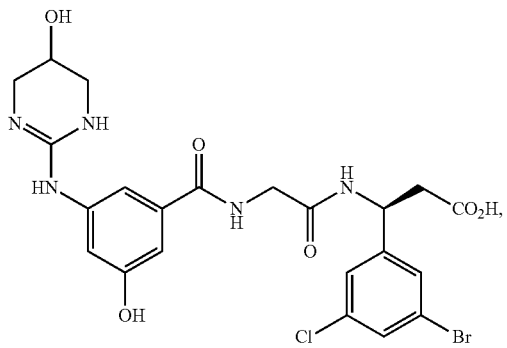
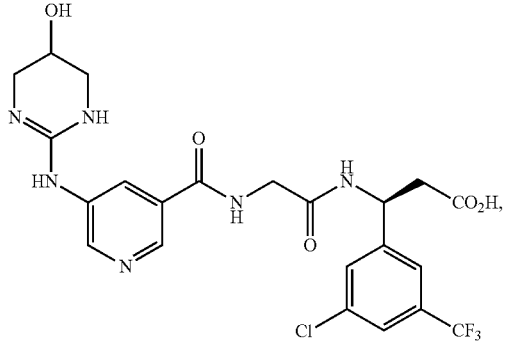
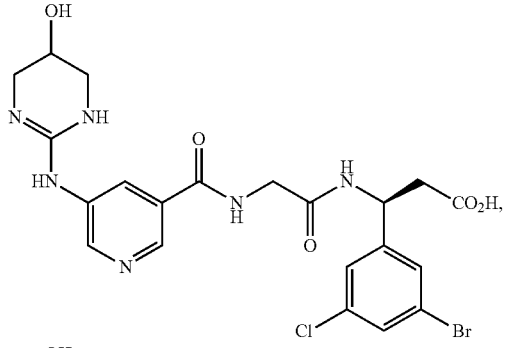
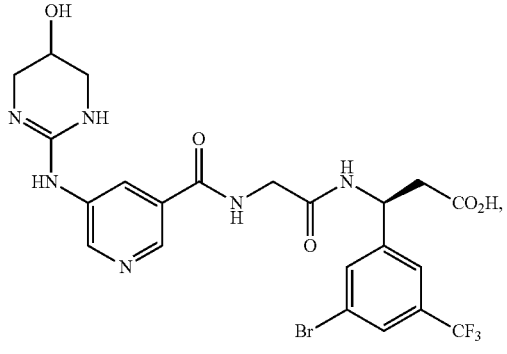
-continued
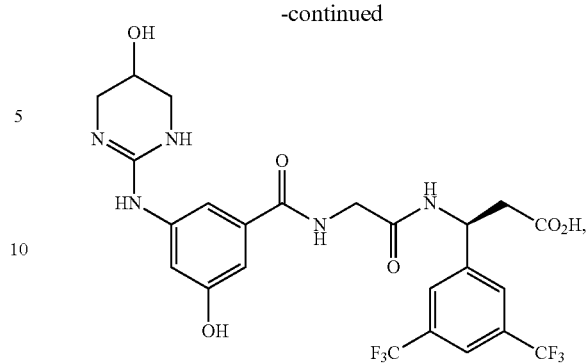
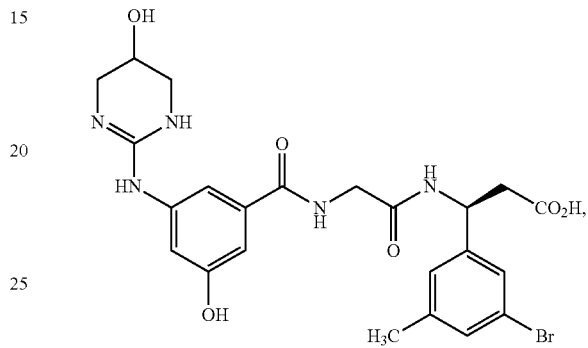
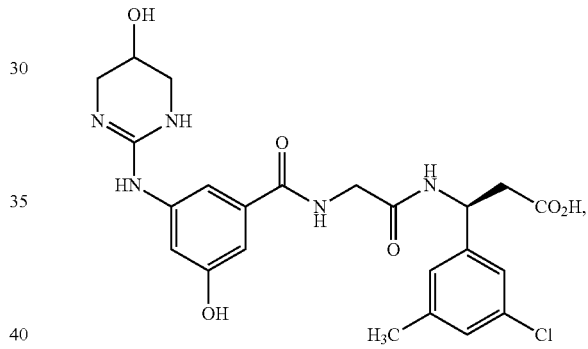
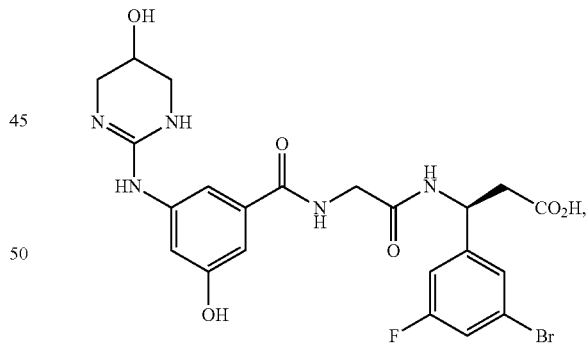
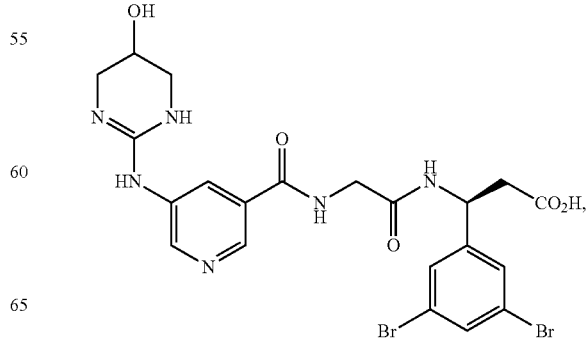

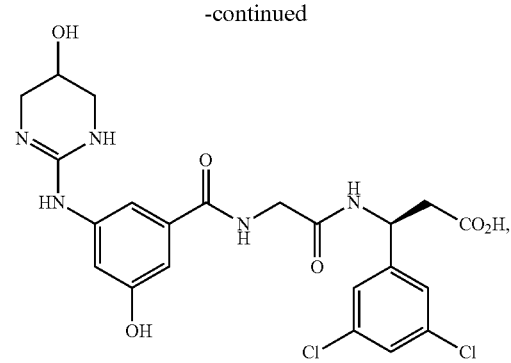

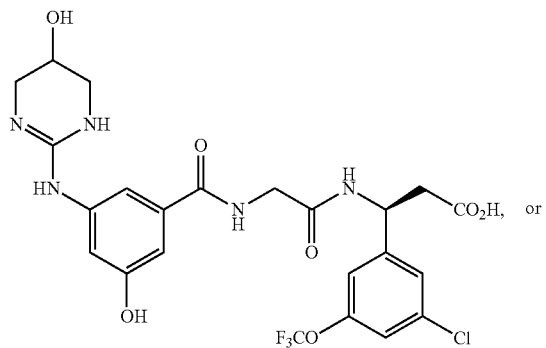

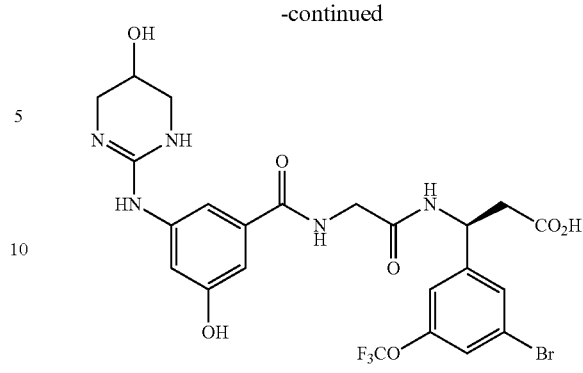

or a pharmaceutically acceptable salt or tautomer of any of the above formulas.

19. A pharmaceutical composition comprising:
   a) the compound of claim 1; and
   b) an excipient.

20. A method of treating and/or preventing a disease or a disorder in a patient in need thereof, comprising administering to the patient a compound of claim 1 in an amount sufficient to treat and/or prevent the disease or disorder, wherein the disease or disorder is associated with angiogenesis or fibrosis.

* * * * *

UNITED STATES PATENT AND TRADEMARK OFFICE
CERTIFICATE OF CORRECTION

| | | |
|---|---|---|
| PATENT NO. | : 10,035,778 B2 | Page 1 of 4 |
| APPLICATION NO. | : 15/812986 | |
| DATED | : July 31, 2018 | |
| INVENTOR(S) | : Peter G. Ruminski et al. | |

It is certified that error appears in the above-identified patent and that said Letters Patent is hereby corrected as shown below:

On the Title Page

On Page 2, Item (56), Column 1, Line 48, under Other Publications, change "$\alpha_v\alpha_3$" to --$\alpha_v\beta_3$--

On Page 3, Item (56), Column 2, Line 59, under Other Publications, change "51(2)1028-1035," to --51(2):1028-1035,--

In the Specification

In Column 16, Line 44, change "(S) beta" to --(S)-beta--

In Column 23, Line 5, change "hplc" to --HPLC--

In Column 45, Line 51, change "TH17" to --Th17--

In Column 47, Line 15, change "α5b1," to --$\alpha 5\beta 1$,--

In Column 47, Lines 15-16, change "avb6, and avb8" to --$\alpha v\beta 6$, and $\alpha v\beta 8$--

In Column 47, Line 67, change "α5b1," to --$\alpha 5\beta 1$,--

In Column 48, Line 1, change "avb6, and avb8" to --$\alpha v\beta 6$, and $\alpha v\beta 8$--

In Column 52, Line 32, change "may taken" to --may be taken--

In Column 53, Line 10, change ""=="" to --"="--

In Column 56, Line 58, change "symptomotology" to --symptomatology--

Signed and Sealed this
Eighteenth Day of June, 2019

Andrei Iancu
*Director of the United States Patent and Trademark Office*

CERTIFICATE OF CORRECTION (continued)
U.S. Pat. No. 10,035,778 B2

In Column 56, Line 60, change "symptomotology" to --symptomatology--

In Column 56, Line 63, change "symptomotology" to --symptomatology--

In Column 57, Line 41, change "that that" to --that--

In Column 58, Line 40, change "symptomotology" to --symptomatology--

In Column 58, Line 41, change "symptomotology)," to --symptomatology),--

In Column 58, Line 43, change "symptomotology" to --symptomatology--

In Column 58, Lines 44-45, change "symptomotology)," to --symptomatology),--

In Column 58, Line 47, change "symptomotology" to --symptomatology--

In Column 61, Line 5, change "2.5N" to --2.5 N--

In Column 62, Line 45 (Approx.), change "pH=2-3." to --pH=2-3.--

In Column 64, Line 25, change "(2M+H" to --(2M+H);--

In Column 64, Line 38 (Approx.), change "2.5N" to --2.5 N--

In Column 67, Lines 11-12, after "Na);" delete "Calculated for m/z 314 ($^{81Br}$M+H), m/z 334 ($^{79Br}$M+Na), and m/z 336 ($^{81Br}$M+Na);"

In Column 71, Line 9 (Approx.), change "($^{81Br}$M+H)" to --($^{81Br}$M+H),--

In Column 71, Line 29, after "($^{81Br}$M+H)," insert --m/z--

In Column 73, Line 1, change "($^{79Br}$M+H)" to --($^{79Br}$M+H),--

In Column 73, Line 2, change "($^{81Br}$M+H)" to --($^{81Br}$M+H),--

In Column 73, Line 3, change "($^{81Br}$M+Na)," to --($^{81Br}$M+Na);--

In Column 73, Line 64, change "($^{37Cl}$M+H)" to --($^{37Cl}$M+H),--

In Column 79, Line 55 (Approx.), change "($^{79Br,79Br}$M+H)" to --($^{79Br,79Br}$M+H),--

In Column 83, Line 15, change "-2-amino)" to -- -2-yl)amino)--

In Column 85, Line 15, change "-2-amino)" to -- -2-yl)amino)--

In Column 87, Line 3, change "($^{37Cl}$M+H)" to --($^{37Cl}$M+H),--

CERTIFICATE OF CORRECTION (continued)
U.S. Pat. No. 10,035,778 B2

In Column 89, Line 1, change ")benzamido)" to --)amino)benzamido)--

In Column 89, Line 7, change "($^{37Cl,81Br}$M+Na)," to --($^{37Cl,81Br}$M+Na);--

In Column 91, Line 12 (Approx.), change "pheny]-" to --phenyl]- --

In Column 92, Line 29, change "[[5[(5" to --[[5-[(5--

In Column 93, Line 56, change "Mhz," to --MHz,--

In Column 94, Line 29 (Approx.), change "pheny]-" to --phenyl]- --

In Column 95, Line 2-3, change "($^{81Br}$M+H) m/z 637 ($^{79Br}$M+Na)" to --($^{81Br}$M+H), m/z 637 ($^{79Br}$M+Na),--

In Column 95, Line 12 (Approx.), change "pheny]-" to --phenyl]- --

In Column 95, Line 54 (Approx.), change "($^{79Br}$M+H)" to --($^{79Br}$M+H), m/z 589 ($^{81Br}$M+H),--

In Column 96, Line 62, change "μL" to --μL,--

In Column 97, Line 1-2, change "-tetrahydropyrimi din-" to -- -tetrahydropyrimidin- --

In Column 104, Line 29, change "[[5[(5" to --[[5-[(5--

In Column 104, Line 66-67, change "-tetrahydropyrimi din-" to -- -tetrahydropyrimidin- --

In Column 105, Line 4, change "($^{81Br,81Br}$M+H)" to --($^{81Br,81Br}$M+H),--

In Column 105, Line 56 (Approx.), change "$C_{21}H_{22}Br_2N_6O_5$:" to --$C_{21}H_{22}Br_2N_6O_5$: 598.24.--

In Column 106, Line 48-49, change "-tetrahydropyrimi din-" to -- -tetrahydropyrimidin- --

In Column 109, Line 51, change "($^{35Cl}$M+H)" to --($^{35Cl}$M+H),--

In Column 111, Line 46, change "($^{81Br}$M+H)" to --($^{81Br}$M+H),--

In Column 115, Line 12 (Approx.), change "anti-β" to --anti-β1--

In Column 116, Line 27 (Approx.), change "supernant" to --supernatant--

In Column 119, Line 63, change "6,013,651" to --6,013,651.--

In Column 119, Line 64, change "6,028,223" to --6,028,223.--

In Column 119, Line 66, change "2005" to --2005.--

In Column 120, Line 67, change "2010" to --2010.--

In the Claims

In Column 121, Line 21 (Approx.), Claim 1, change "CH, COH," to --C—H, C—OH,--

In Column 121, Line 65, Claim 10, change "compound" to --compound of--